United States Patent
Carbo, Jr. et al.

(10) Patent No.: US 12,220,227 B2
(45) Date of Patent: Feb. 11, 2025

(54) DEVICES, SYSTEMS, AND METHODS TO MONITOR AND CHARACTERIZE THE MOTIONS OF A USER VIA FLEXIBLE CIRCUITS

(71) Applicant: Liquid Wire LLC, Portland, OR (US)

(72) Inventors: Jorge E. Carbo, Jr., Portland, OR (US); Katherine M. Nelson, Portland, OR (US); Michael Jasper Wallans, Portland, OR (US); Michael Adventure Hopkins, Portland, OR (US); Mark William Ronay, Portland, OR (US); Casey Culbertson, West Linn, OR (US)

(73) Assignee: Liquid Wire LLC, Portland, OR (US)

( * ) Notice: Subject to any disclaimer, the term of this patent is extended or adjusted under 35 U.S.C. 154(b) by 0 days.

(21) Appl. No.: 18/549,438

(22) PCT Filed: Mar. 7, 2022

(86) PCT No.: PCT/US2022/071012
§ 371 (c)(1),
(2) Date: Sep. 7, 2023

(87) PCT Pub. No.: WO2022/192859
PCT Pub. Date: Sep. 15, 2022

(65) Prior Publication Data
US 2024/0172963 A1    May 30, 2024

Related U.S. Application Data

(60) Provisional application No. 63/241,806, filed on Sep. 8, 2021, provisional application No. 63/235,937, filed
(Continued)

(51) Int. Cl.
*A61B 5/00*     (2006.01)
*A61B 5/01*     (2006.01)
*A61B 5/11*     (2006.01)

(52) U.S. Cl.
CPC .............. *A61B 5/11* (2013.01); *A61B 5/0002* (2013.01); *A61B 5/01* (2013.01); *A61B 5/6812* (2013.01);
(Continued)

(58) Field of Classification Search
CPC   A61B 5/11; A61B 5/0002; A61B 5/01; A61B 5/6812; A61B 5/742;
(Continued)

(56) References Cited

U.S. PATENT DOCUMENTS 10,194,837 B2 * 2/2019 Kanchan ............... A61B 5/6806
10,527,507 B2   1/2020 Wood et al.
(Continued)

FOREIGN PATENT DOCUMENTS

WO   2018222963 A1   12/2018
WO   2022192859 A1   9/2022

OTHER PUBLICATIONS

International Search Report and Written Opinion for corresponding International PCT Application No. PCT/US2022/071012, dated Jul. 5, 2022.
(Continued)

*Primary Examiner* — May A Abouelela
(74) *Attorney, Agent, or Firm* — Quinn IP Law

(57) ABSTRACT

A system configured to monitor and characterize motions of a user is disclosed herein. The system can include a wearable article including a tubular body comprising a resilient material, a flexible circuit including a fluid-phase conductor configured to generate a first signal, and an inertial measurement unit ("IMU") coupled to the resilient material,
(Continued)

wherein the IMU is configured to generate a second signal. The system can further include a processor communicably coupled to the flexible circuit and the IMU.

9 Claims, 25 Drawing Sheets

Related U.S. Application Data on Aug. 23, 2021, provisional application No. 63/157,812, filed on Mar. 7, 2021.

(52) U.S. Cl.
CPC ...... *A61B 5/742* (2013.01); *A61B 2562/0219* (2013.01); *A61B 2562/0247* (2013.01); *A61B 2562/164* (2013.01)

(58) Field of Classification Search
CPC .... A61B 2562/0219; A61B 2562/0247; A61B 2562/164; A61B 5/4519; A61B 5/4528; A61B 5/224; A61B 5/6804; A61B 5/7246; A61B 2560/0238; A61B 5/1107; A61B 5/1122; A61B 5/1124; A61B 5/256; A61B 5/265; A61B 5/268; A61B 5/274; A61B 5/294; A61B 5/1121; A61B 5/1116; A61B 5/6802; A61B 2562/0271
See application file for complete search history.

(56) References Cited

U.S. PATENT DOCUMENTS

| | | | | |
|---|---|---|---|---|
| 10,842,407 | B2* | 11/2020 | Berenzweig | G06F 3/015 |
| 10,912,512 | B2* | 2/2021 | Moradi | A61F 2/7812 |
| 10,993,639 | B2* | 5/2021 | Herr | A61B 5/4585 |
| 2008/0312756 | A1 | 12/2008 | Grichnik et al. | |
| 2013/0027341 | A1 | 1/2013 | Mastandrea | |
| 2013/0217998 | A1 | 8/2013 | Mahfouz et al. | |
| 2016/0262687 | A1 | 9/2016 | Vaidyanathan et al. | |
| 2018/0303383 | A1* | 10/2018 | Connor | G06F 3/014 |
| 2018/0325766 | A1* | 11/2018 | Arzanpour | A61H 1/0237 |
| 2019/0117156 | A1 | 4/2019 | Howard et al. | |
| 2019/0223748 | A1* | 7/2019 | Al-natsheh | A61B 5/6824 |
| 2020/0073483 | A1* | 3/2020 | Berenzweig | G06N 5/04 |
| 2020/0145797 | A1* | 5/2020 | Craig | A61B 5/4585 |
| 2021/0068713 | A1* | 3/2021 | Dervisoglu | A61B 5/0205 |
| 2021/0128972 | A1* | 5/2021 | Lee | B25J 9/0006 |
| 2022/0148723 | A1* | 5/2022 | Ramachandran | G16H 50/20 |
| 2022/0160240 | A1* | 5/2022 | D'Estais | G01K 7/427 |
| 2023/0061808 | A1* | 3/2023 | Gillian | G06F 9/44505 |

OTHER PUBLICATIONS

Ozutemiz Kadri Bugra et al: "EGain-Metal Interfacing for Liquid Metal Circuitry and Microelectronics Integration", Advanced Materials Interfaces, vol. 5, No. 10, Mar. 15, 2018 (Mar. 15, 2018), XP093227907, DE ISSN: 2196-7350, DOI: 10.1002/admi.201701596 Retrieved from the Internet: URL:https://onlinelibrary.wiley.com/doi/fu ll-xml/10.1002/admi.201701596>* p. 1-p. 13; figures 1-7 *.

Yirmibesoglu Osman Dogan et al: "Hybrid soft sensor with embedded IMUs to measure motion", 2016 IEEE International Conference on Automation Science and Engineering (CASE), IEEE, Aug. 21, 2016 (Aug. 21, 2016), pp. 798-804, XP033005456, DOI: 10.1109/COASE.2016.7743483.

Yong-Lae Park et al: "Hyperelastic pressure sensing with a liquid-embedded elastomer;Hyperelastic pressure sensing", Journal of Micromechanics and Microengineering, Institute of Physics Publishing, Bristol, GB, vol. 20, No. 12, Nov. 29, 2010 (Nov. 29, 2010), p. 125029, XP020201652, ISSN: 0960-1317, DOI: 10.1088/0960-1317/20/12/125029 * p. 1-p. 5; figures 1-6 *.

* cited by examiner

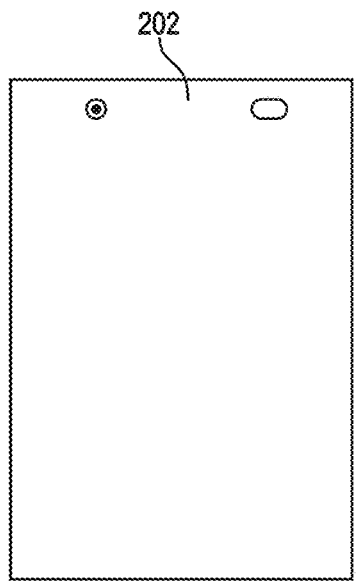 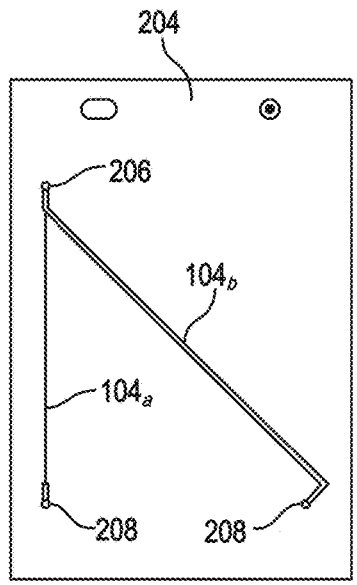 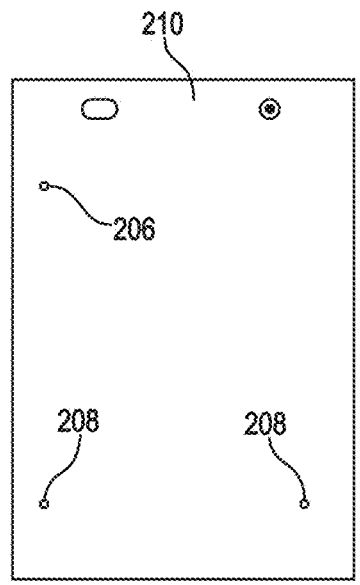
FIG. 2A  FIG. 2B  FIG. 2C
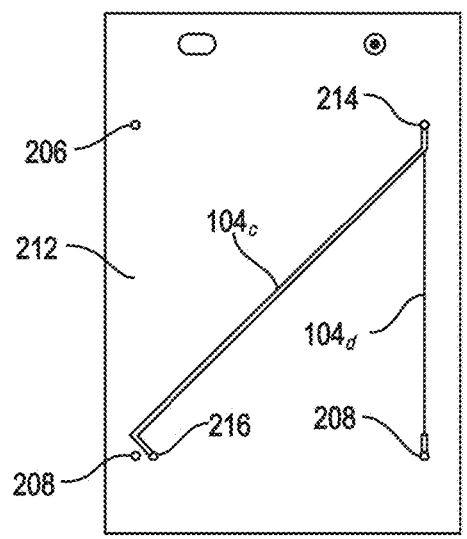 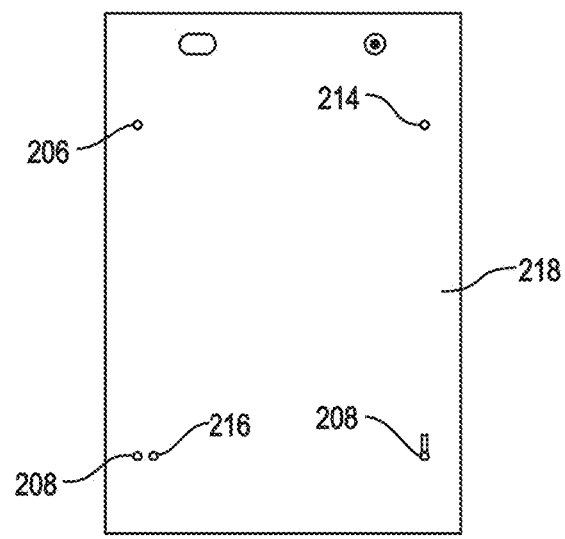
FIG. 2D  FIG. 2E

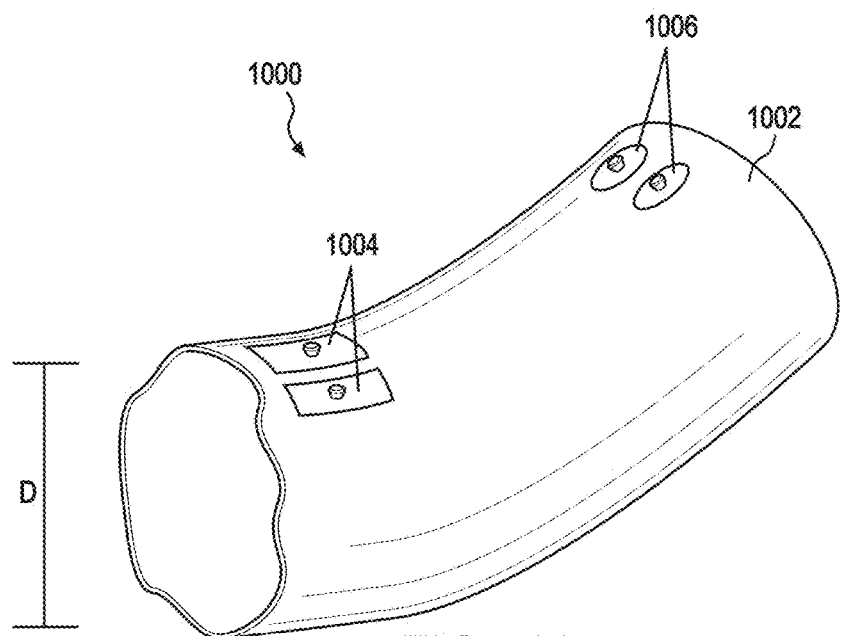
FIG. 10
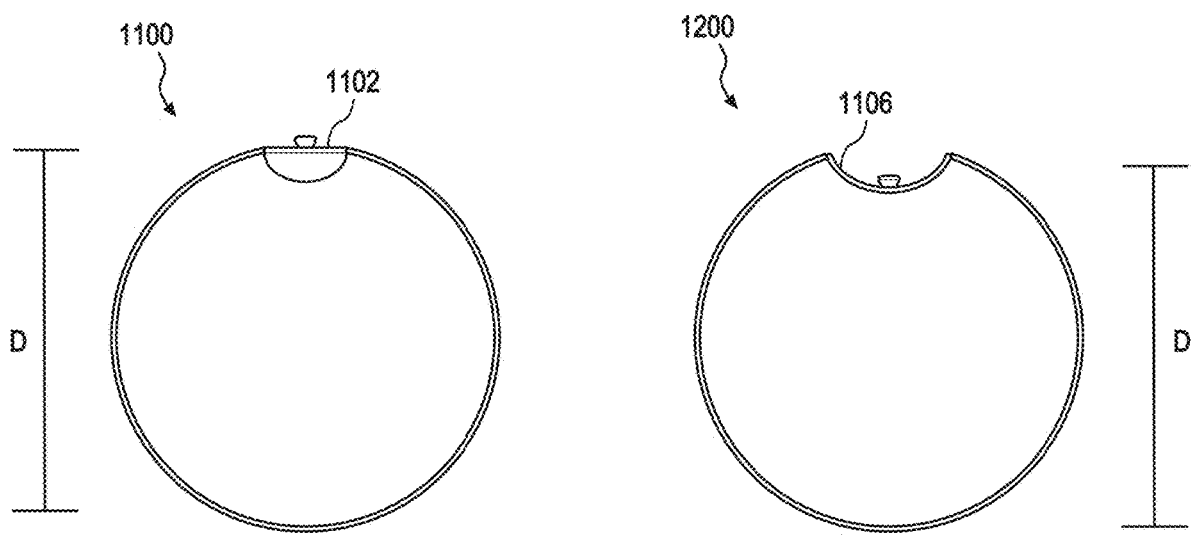
FIG. 11
FIG. 12

DEVICES, SYSTEMS, AND METHODS TO MONITOR AND CHARACTERIZE THE MOTIONS OF A USER VIA FLEXIBLE CIRCUITS

CROSS-REFERENCE TO RELATED APPLICATIONS

This application is a U.S. National Stage Entry under 35 U.S.C. § 371 of International Patent Application No. PCT/US2022/071012, entitled DEVICES, SYSTEMS, AND METHODS TO MONITOR AND CHARACTERIZE THE MOTIONS OF A USER VIA FLEXIBLE CIRCUITS, filed Mar. 7, 2022, which claims benefit under 35 U.S.C. § 119 (e) to U.S. Provisional Patent Application No. 63/157,812, titled JOINT MONITORING SLEEVE, filed Mar. 7, 2021, U.S. Provisional Patent Application No. 63/235,937, titled BIASING ELECTRODES SLEEVES, filed Aug. 23, 2021, and U.S. Provisional Patent Application No. 63/241,806, titled BRACE WITH INERTIAL MEASUREMENT UNITS, filed Sep. 8, 2021, the disclosures of which are hereby incorporated by reference in their entirety.

FIELD

The present disclosure is generally related to flexible circuits and, more particularly, is directed to flexible circuits that can be either integrated into wearable articles for the purposes of generating simulated motions in a virtual environment that correspond to physical motions in a real environment.

SUMMARY

The following summary is provided to facilitate an understanding of some of the innovative features unique to the aspects disclosed herein and is not intended to be a full description. A full appreciation of the various aspects can be gained by taking the entire specification, claims, and abstract as a whole.

In various aspects, a system configured to monitor and characterize motions of a user is disclosed. The system can include a wearable article including a tubular body including a resilient material; a flexible circuit including a fluid-phase conductor configured to generate a first signal; and an inertial measurement unit ("IMU") coupled to the resilient material, wherein the IMU is configured to generate a second signal; and a processor communicably coupled to the flexible circuit and the IMU.

In various aspects, a wearable article configured to monitor motions of a user is disclosed. The wearable article can include a tubular body including a resilient material; a flexible circuit including a fluid-phase conductor configured to generate a first signal; and an inertial measurement unit ("IMU") coupled to the resilient material, wherein the IMU is configured to generate a second signal; and wherein the flexible circuit and the IMU are communicably coupled to a processor via a plurality of conductive traces including the fluid-phase conductor.

In various aspects, a method of generating a virtual representation of a physical motion performed by a user of a wearable article including a plurality of flexible circuits is disclosed. The method can include: performing a first motion while wearing the wearable article; generating, via a first flexible circuit of the plurality of flexible circuits, a first electrical parameter associated with the first motion; generating via a camera, motion capture data associated with the performance of the first motion; correlating, via a processor communicably coupled to the wearable article, the generated motion capture data to the generated first electrical parameter; storing, via a memory communicably coupled to the processor, the correlation; repeating the first motion while wearing the wearable article; and generating, via the processor, a virtual replication of the first motion based on exclusively on the stored correlation of the generated motion capture data to the generated first electrical parameter.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Various features of the aspects described herein are set forth with particularity in the appended claims. The various aspects, however, both as to organization and methods of operation, together with advantages thereof, may be understood in accordance with the following description taken in conjunction with the accompanying drawings as follows:

FIGS. 2A-E illustrate individual layers of a medium of the strain sensor system of FIG. 1, according to at least one non-limiting aspect of the present disclosure;

FIG. 10 illustrates a wearable article, in accordance with at least one non-limiting aspect of the present disclosure;

FIG. 11 illustrates another wearable article, in accordance with at least one non-limiting aspect of the present disclosure;

FIG. 12 illustrates another wearable article, in accordance with at least one non-limiting aspect of the present disclosure;

Corresponding reference characters indicate corresponding parts throughout the several views. The exemplifications set out herein illustrate various aspects of the invention, in one form, and such exemplifications are not to be construed as limiting the scope of the invention in any manner.

DETAILED DESCRIPTION

Figure 1:
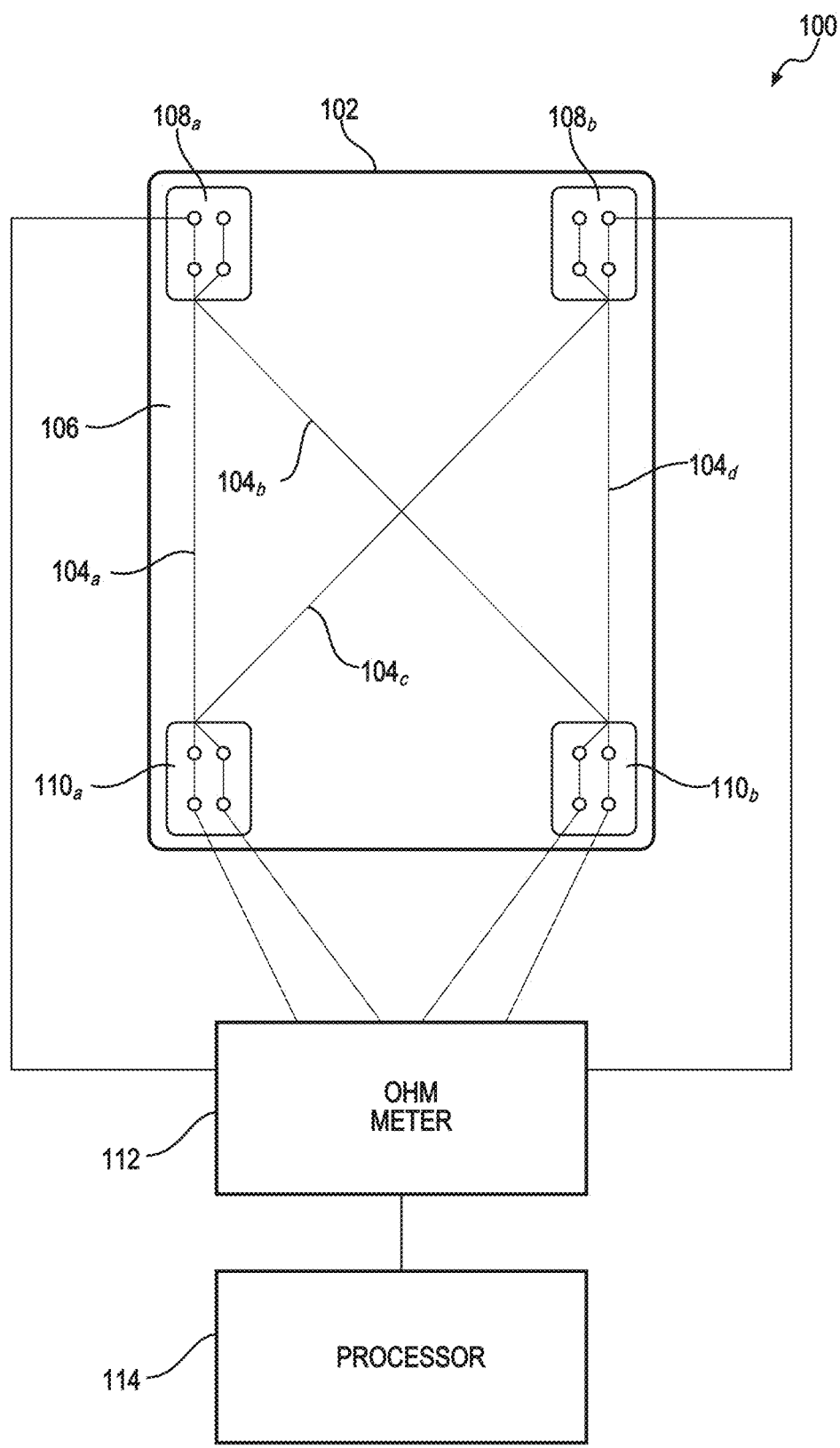
FIG. 1 illustrates a strain sensor system including a two-dimensional strain sensor, according to at least one non-limiting aspect of the present disclosure.

Numerous specific details are set forth to provide a thorough understanding of the overall structure, function, manufacture, and use of the aspects as described in the disclosure and illustrated in the accompanying drawings. Well-known operations, components, and elements have not been described in detail so as not to obscure the aspects described in the specification. The reader will understand that the aspects described and illustrated herein are non-limiting examples, and thus it can be appreciated that the specific structural and functional details disclosed herein may be representative and illustrative. Variations and changes thereto may be made without departing from the scope of the claims. Furthermore, it is to be understood that such terms as "forward", "rearward", "left", "right", "upwardly", "downwardly", and the like are words of convenience and are not to be construed as limiting terms. Furthermore, it is to be understood that such terms as "forward", "rearward", "left", "right", "upwardly", "downwardly", and the like are words of convenience and are not to be construed as limiting terms.

The present application is related to U.S. patent application Ser. No. 15/947,744, titled DEFORMABLE CONDUCTORS AND RELATED SENSORS, ANTENNAS AND MULTIPLEXED SYSTEMS, filed Apr. 6, 2018, and published as U.S. Patent Application Publication No. 2018/0247727 on Aug. 30, 2018, U.S. patent application Ser. No. 16/157,102, titled SENSORS WITH DEFORMABLE CONDUCTORS AND SELECTIVE DEFORMATION, filed Oct. 11, 2018, and published as U.S. Patent Application Publication No. 2019/0056277 on Feb. 21, 2019, U.S. patent application Ser. No. 16/885,854, titled CONTINUOUS INTERCONNECTS BETWEEN HETEROGENEOUS MATERIALS, filed May 28, 2020, and published as U.S. Patent Application Publication No. 2020/0381349 on Dec. 3, 2020, U.S. patent application Ser. No. 16/893,427, titled DEFORMABLE SENSORS WITH SELECTIVE RESTRAINT, filed Jun. 4, 2020, and published as U.S. Patent Application Publication No. 2020/0386630 on Dec. 3, 2020, U.S. patent application Ser. No. 17/192,725, titled DEFORMABLE INDUCTORS, filed Mar. 4, 2021, and published as U.S. Patent Application Publication No. 2021/0280482 on Sep. 9, 2021, and U.S. Provisional Patent Application No. 63/263,112, titled TWO DIMENSIONAL MOTION CAPTURE STRAIN GAUGE SENSOR, filed Oct. 10, 2021, the disclosures of which are hereby incorporated by reference in their entirety.

In the following description, like reference characters designate like or corresponding parts throughout the several views of the drawings. Also in the following description, it is to be understood that such terms as "forward", "rearward", "left", "right", "upwardly", "downwardly", and the like are words of convenience and are not to be construed as limiting terms.

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves any and all copyrights disclosed herein.

There is a growing need for the accurate integration of physical and virtual environments. Indeed, augmented and virtual realities—including the metaverse—are becoming increasingly prevalent and promise to reinvent the way people work, play, relax, and rehabilitate. Conventional "smart" apparel (e.g., sleeves, braces, gloves, tight-fitting clothing, etc.), however, generally utilize sensors, such as inertial measurement units ("IMUs"), that can be expensive and experience "drift" over time, resulting in an insufficient value proposition. As such, conventional devices can lack the accuracy required for certain applications where precision is important. For example, range of motion during joint (e.g., knee, elbow, etc.) flexion can be a key indicator of knee joint health. It would be beneficial for a doctor to simulate, with a high-degree of accuracy, the full range of motion of a patient's body part (e.g., leg, arm, shoulder, neck, back, hand, wrist, finger, ankle, foot, toe, etc.), such that rehabilitation can be tracked and remotely reviewed. If the user's motion is tracked with sufficient accuracy, the doctor can benefit from an increased amount of oversight and the patient could benefit from the convenience of virtual appointments and consultations.

According to another example, the metaverse promises to provide a gamut of virtual products and services to consumers. As previously mentioned, conventional devices can lack the accuracy necessary to enable this unprecedented market. For example, many conventional devices rely on relative point-to-point data for a limited approximation of the user's motions (e.g., position of a user's knee relative their hip). However, if the user wanted to play a virtual game of soccer in the metaverse with their friends, more accurate representations of the user's motions would enhance the experience. Accordingly, there is a need for devices, systems, and methods, to accurately simulate a user's motions in a virtual environment. According to some non-limiting aspects, such devices, systems, and methods may utilize flexible circuits and, particularly, a deformable conductor that can promote stretchability as well as flexibility while preserving electrical conductivity. As such, electrical parameters measured across those circuits can be correlated to a user's physical motions and can inform accurate simulations.

While certain electronic components typically have some inherent flexibility, that flexibility is typically constrained both in the amount the components can flex, their resilience in flexing, and the number of times the electronic components can flex before the electronic components deteriorate or break. Moreover, electronics that have the ability to stretch, such as those comprising silver or other conductive inks, have insufficient durability and typically do not recover fully when subjected to elongation, resulting in ever-changing electrical characteristics until they fail completely. Consequently, the utility of such electronic components in various environments may be limited, either by reliability or longevity or by the ability to function at all.

The use of conductive gel for traces in the circuit, however, provides for electronic components that are flexible, extensible and deformable while maintaining resiliency. Moreover, the operational flexing, stretching, deforming, or other physical manipulation of a conductive trace formed from conductive gel may produce predictable, measurable changes in the electrical characteristics of the trace with little to no hysteresis upon returning to a relaxed state. By measuring the change in resistance or impedance of such a trace the change in length of the trace may be inferred. By combining the changes in lengths of multiple traces, the relative movement of points on a two-dimensional surface may be calculated. The relative movement of points in a three-dimensional space may be calculated and determined using two-dimensional displacement information if the points are disposed on a body that has constrained motion, for example, points located on limbs of a body that are interconnected by a joint.

According to some non-limiting aspects, a flexible circuit can be constructed as disclosed in U.S. Provisional Patent Application No. 63/154,665, titled HIGHLY SUSTAINABLE CIRCUITS AND METHODS FOR MAKING THEM, filed Feb. 26, 2021, and/or International Patent Application No. PCT/US2019/047731 titled STRUCTURES WITH DEFORMABLE CONDUCTORS, filed Aug. 22, 2019, the disclosures of which are hereby incorporated by reference in their entirety.

Additionally, the traces of a flexible circuit can be constructed from a fluid-phase conductor. As used herein, the term "fluid-phase conductor" shall include any of the flexible, deformable conductors described herein and/or any of the flexible, deformable conductors described in any document incorporated by reference. Specifically, "fluid-phase conductors" are described in International Patent Application No. PCT/US2017/019762 titled LIQUID WIRE, which was filed on Feb. 27, 2017 and published on Sep. 8, 2017 as International Patent Publication No. WO2017/151523A1, and/or International Patent Application No. PCT/US2019/047731 titled STRUCTURES WITH DEFORMABLE CONDUCTORS, filed Aug. 22, 2019, the disclosures of which are hereby incorporated by reference in their entirety.

For example, according to some non-limiting aspects, each trace can include a variety of forms, such as a liquid, a paste, a gel, and/or a powder, amongst others that would enable the traces to have a deformable (e.g., soft, flexible, stretchable, bendable, elastic, flowable viscoelastic, Newtonian, non-Newtonian, etc.) quality. According to some non-limiting aspects, the deformable, conductive materials can include an electroactive material, such as deformable conductors produced from a conductive gel (e.g., a gallium indium alloy). The conductive gel can have a shear thinning composition and, according to some non-limiting aspects, can include a mixture of materials in a desired ratio. For example, according to one preferable non-limiting aspect, the conductive gel can include a weight percentage of a eutectic gallium alloy between 59.9% and 99.9% and a weight percentage of a gallium oxide between 0.1% and about 2.0%. Of course, the present disclosure contemplates other non-limiting aspects, featuring traces of varying forms and/or compositions to achieve the benefits disclosed herein.

The electrically conductive compositions can be characterized as conducting shear thinning gel compositions. The electrically conductive compositions described herein can also be characterized as compositions having the properties of a Bingham plastic. For example, the electrically conductive compositions can be viscoplastics, such that they are rigid and capable of forming and maintaining three-dimensional features characterized by height and width at low stresses but flow as viscous fluids at high stress. According to other non-limiting aspects, the low-shear viscosity of useful metal gel can be $10^6$ to $4 \times 10^7$ Pa*s (1,000,000-40,000,000 Pascal seconds), wherein "low-shear" viscosity refers to a viscosity at rest (or sedimentation) conditions. The micro/nanostructure comprises oxide sheets that form a cross-linked structure, which may be achieved e.g. by mixing in a way that entrains air into the mixture, or by sonication that induces cavitation at the surface drawing in air to the mixture such that oxide formation in the cross-linked structures can be achieved.

It shall be appreciated that, by using flexible circuits and deformable conductors, various sensors can be constructed that, when integrated into a wearable article (e.g., sleeves, braces, etc.) worn by a user, can generate varying electrical parameters (e.g., an inductance, a resistance, a voltage drop, a capacitance, and an electromagnetic field, etc.) that can be correlated to physical parameters (e.g., a strain, a stress, a pressure, a dimension, etc.) and thus, used to generate highly accurate simulations of the user's motions while wearing the article. For example, a wearable article (e.g., a knee brace, an elbow sleeve, etc.) can utilize flexible circuits and deformable conductors configured to function as sensors (e.g., a strain sensor, etc.). Enabled by the deformable conductor, which is configured to move with the joint, a wearable article can actively and accurately monitor joint flexibility without substantial electrical or physical degradation over thousands of strain cycles. Accordingly, continuous calibration is unnecessary and conversely, the flexible circuits can be used to calibrate conventional sensors (e.g., IMUs, etc.). In addition, parts of the circuit can be specifically configured and positioned to measure strain and thus, swelling in a particular location of the patient's appendage (e.g., shin, etc.).

For example, the aforementioned circuits can be implemented to form a two-dimensional strain sensor that utilizes a network of conductive gel traces, the individual electrical characteristics of which translates to a relative length or other orientation of the trace. By combining the electrical characteristics (e.g., by triangulating or other mathematical process, etc.) the relative location of various points on a two-dimensional surface may be determined. By measuring such electrical characteristics repeatedly over time, the motion of the points may be determined, providing for the capacity for real-time motion capture of the points on the strain sensor. By scaling the network of traces and/or increasing the number of strain sensors and placing the strain sensors on an object, motion capture the object may be obtained in real-time.

Referring now to FIG. 1, a strain sensor system 100 including a two-dimensional strain sensor 102 is depicted in accordance with at least one non-limiting aspect of the present disclosure. As an example, the strain sensor system 100 can be configured similar to those disclosed in U.S. Provisional Patent Application No. 63/263,112, titled TWO DIMENSIONAL MOTION CAPTURE STRAIN GAUGE SENSOR, filed Oct. 10, 2021, the disclosures of which are hereby incorporated by reference in its entirety. According to the non-limiting aspect of FIG. 1, the strain sensor 102 can include a number of traces 104a, 104b, 104c, 104d. Although FIG. 1 depicts four traces 104a, 104b, 104c, 104d, the number of traces can be specifically configured according to user preference and/or intended application. Each trace 104a-104d can be made of conductive gel, as disclosed in detail herein. The conductive gel can be positioned on and encapsulated by a medium 106. Each trace 104a, 104b, 104c, 104d can extend between and electrically couple one of two reference point 108a, 108b to an anchor point 110a, 110b. In the illustrated example, reference points 108a, 108b are not directly connected to one another and the anchor points anchor point 110a, 110b are not directly connected to one another.

The medium 106 specifically and the strain sensor 102 generally may be formed according to the techniques described herein or according to any other mechanism that exists or may be developed, including but not limited to injection molding, 3D printing, thermoforming, laser etching, die-cutting, and the like. The medium 106 may be formed of one of: a B-stage resin film, a C-stage resin film, an adhesive, a thermoset epoxy-based film, thermoplastic polyurethane (TPU), and/or silicone, among other suitable compounds or materials. In an example, the medium 106 has tensile elongation of 550%; tensile modulus of 5.0 megapascals; recovery rate of 95%; thickness of 100 micrometers; a peel strength at 90 degrees of at least 1.0 kilonewtons per meter; a dielectric constant of 2.3 at 10 gigahertz; a dielectric dissipation factor of 0.0030 at 10 gigahertz; a breakdown voltage of 7.0 kilovolts at a thickness of 80 micrometers; a heat resistance that produces no change in an environment of 260 degrees Celsius for 10 cycles in a nitrogen atmosphere; and chemical resistance producing no change to the medium 106 after 24 hours immersion in any of NaOH, Na2CO3, or copper etchant.

Details of an example medium 106 are disclosed in U.S. Patent Application Publication No. 2020/0381349, "CONTINUOUS INTERCONNECTS BETWEEN HETEROGENEOUS MATERIALS", Ronay et al., which is incorporated by reference herein in its entirety.

The strain sensor 102 is configured to identify changes in the relative positions of the reference points 108a, 108b based on a change in impedance/resistance of one or more of the traces 104a, 104b, 104c, 104d. In particular, the strain sensor 102 is configured to determine the relative position according to the Cartesian system (x, y) on a plane defined by the medium 106 of a given reference point 108a, 108b in relation to the two anchor points 110a, 110b to which the reference point 108a, 108b is coupled via an associated trace 104a, 104b, 104c, 104d. Thus, for instance, the relative position of the reference point 108a may be determined by one or, inferentially, both of: determining the length at any given time of the trace 104a and the trace 104b and/or by determining the relative position (x, y) of the anchor points 110a, 110b.

The length of the traces 104a, 104b may be determined as a function of resistance and/or impedance of the given trace 104a, 104b, 104c, 104d as measured between the reference point 108a, 108b and the anchor point 110a, 110b that is coupled by the trace 104a, 104b, 104c, 104d. In the illustrated example, the strain sensor system 100 includes an electronic parameter sensor 112 operatively coupled to a processor 114. The electronic parameter sensor 112 may be any device that is configured to detect or otherwise measure an electronic property, such as resistance, capacitance, inductance, etc. As such, in various examples, the electronic parameter sensor 112 may be an ohm meter or a resistance signal reader. Further, the electronic parameter sensor 112 and the processor 114 may be separate components or integrated together. In such an example, the processor 114 may be part of a chipset or package that incorporates resistance signal reading and recording capabilities. In still yet other examples, an analog to digital signal processor may be utilized to convert an analog resistance signal to a digital signal, which may be received by the processor 114. In examples where a remote processor is configured to receive signals from the strain sensor 102, a wireless communication component integrated to the sensor may be configured to provide signals to the processor 114.

While the strain sensor system 100 as illustrated includes the electronic parameter sensor 112 and the processor 114, it is to be recognized and understood that one or both of the electronic parameter sensor 112 and the processor 114 may be remote to the rest of the strain sensor system 100 and/or cloud computing assets, etc. Moreover, in various examples the electronic parameter sensor 112 and/or the processor 114 may be integrated into the strain sensor 102 itself or may be components to which the strain sensor 102 is operatively coupled, as illustrated. In examples where the processor 114 and/or the electronic parameter sensor 112 are remote to the strain sensor 102, a wireless communication module may be incorporated into the strain sensor 102 to provide data to the electronic parameter sensor 112 and/or processor 114.

In various examples, the processor 114 does not require a calibrated or predetermined relationship of impedance of a given trace 104a, 104b, 104c, 104d to determine the relative position of a reference point 108a, 108b and/or a relative position of an anchor point 110a, 110b. In such an example, the processor 114 may determine the relative location (x, y) on the medium 106 of the reference point 108a by determining location of the reference point 108a relative to the determined location (x, y) of each of the anchor points 110a, 110b to which the traces 104a, 104b are coupled. In such an example, the location variables x and y of the reference point 108a may be determined by the processor 114 according to the following equations:

$$x = \frac{\ell}{\partial}(x_a - x_b) \pm \frac{h}{\partial}(y_a - y_b) + x_b \quad \text{Equation 1}$$

X−Coordinate of the Reference Point $$y = \frac{\ell}{\partial}(y_a - y_b) \pm \frac{h}{\partial}(x_a - x_b) + y_b \quad \text{Equation 2}$$

Y−Coordinate of the Reference Point $$h = \sqrt{r_b^2 - \ell^2} \quad \text{Equation 3}$$

Sub−Calculation #1

$$\ell = \frac{r_b^2 - r_a^2 + \partial^2}{2\partial} \quad \text{Equation 4}$$

-continued

Sub-Calculation #2

$$\partial = \sqrt{(x_a - x_b)^2 + (y_a - y_b)^2} \quad \text{Equation 5}$$

Sub-Calculation #3

In the above equations, r is the impedance for a given trace 104a, 104b as measured by the electronic parameter sensor 112 and provided to the processor 114. By applying the same equations in the same manner for the reference point 108b, but for the traces 104c, 104d, the position of each of the reference points 108a, 108b may be determined. By performing the calculations at a relatively high frequency, e.g., at least once per second, or at least fifteen (15) times per second, or at least twenty-four times per second, etc., the strain sensor system 100 may obtain a real-time determination of the relative positions of the reference points 108a, 108b and, therefore, the amount and rate of movement of the reference points 108a, 108b.

While the strain sensor system 100 is described with respect the measurement of resistance or impedance, it is to be recognized and understood that any electrical measurement may be applied on a similar basis. Thus, for instance, the traces 104a, 104b, 104c, 104d may have or may be configured to have an inductance, a capacitance, or other measureable electronic property that may be changed based on a deformation of the trace. Consequently, while an electronic parameter sensor 112 is described and illustrated, it is to be recognized and understood that any electronic meter configured to sense and measure the relevant electronic property may be utilized in addition to or instead of the electronic parameter sensor 112 in a manner consistent with this disclosure. Parameter sensor 112 can include an analog to digital signal converter, operable for communicating with processor 114, which may process signals digitally.

FIGS. 2A-2E are depictions of individual layers of the medium 106 of the strain sensor 102, in an example aspect. In the example of FIGS. 2A-2E, the strain sensor 102 is a laminate structure in that individual layers of the medium 106 are separately formed, stacked, and unitized together to create the medium 106 as a whole. The layers may be formed according to iterative stencil-in-place processes described in in U.S. Patent Application Publication No. 2020/0066628, "STRUCTURES WITH DEFORMABLE CONDUCTORS", the disclosure of which is hereby incorporated by reference in its entirety, or according to any suitable mechanism. However, as noted above, the formation of the strain sensor 102 as a laminate structure is for example and not limitation and any suitable technique for making the strain sensor 102 may be applied instead of or in addition to the process of making the strain sensor 102 as a laminate structure. The depictions of the layers are looking along a major axis of the strain sensor 102 and are thus either a top or bottom view of the layer relative to the perspective of FIG. 1.

According to the non-limiting aspect of FIGS. 1-4, the sensors 102, 402, flexible circuits, and wearable articles disclosed herein can include one or more substrates mounted to a primary material, wherein the one or more substrates are composed of flexible and stretchable materials, such as those disclosed by U.S. patent application Ser. No. 16/548,379 titled STRUCTURES WITH DEFORMABLE CONDUCTORS, which was filed on Aug. 22, 2019 and granted as U.S. Pat. No. 11,088,063 on Aug. 10, 2021, the disclosure of which is hereby incorporated by reference in its entirety. Specifically, the one or more substrates can be fabricated from a flexible or stretchable material such as a natural rubber, a synthetic rubber, a flexible plastic, a silicone based material (e.g., polydimethylsiloxane ("PDMS"), thermoplastic polyurethane ("TPU"), ethylene propylene dieneterpolymer ("EPDM"), neoprene, polyethylene terephthalate ("PET"), a flexible composite material, and/or a naturally flexible material, such as a leather, for example. For example, the one or more substrates can be fabricated from a resilient, albeit stretchable TPU, such as Lubrizol® Estane® 58000 series (e.g., 58238), amongst others. Alternatively, the one or more substrates can be formed from a flexible, though comparatively more rigid material, such as Lubrizol® Estane® S375D, amongst others. According to other non-limiting aspects, the primary material of the wearable article, itself, can include any of the aforementioned flexible and/or stretchable materials. Although the substrates can include a multi-layer construction-including a substrate layer, a stencil-layer, and an encapsulation layer— in other non-limiting aspects, the substrates can include a two-layer construction (e.g., substrate layer, encapsulation layer, etc.) or even a single layer configured to accommodate the deformable traces.

FIG. 2A is substrate layer 202. The substrate layer 202 is formed of the material of the medium 106 and eventually has traces 104a, 104b placed thereon but is otherwise featureless and may, in various examples, provide insulation for and/or containment of the conductive gel.

FIG. 2B is a first patterned layer 204. The first patterned layer 204 is formed of the material of the medium 106 and includes the traces 104a, 104b, e.g., formed as channels that contain conductive gel formed in the medium 106. Additionally, a first reference via 206 and first anchor vias 208 are operatively coupled to the respective traces 104a, 104b and provide electrical access to the traces 104a, 104b through various layers of the strain sensor 102. The vias 206, 208 may be formed from conductive gel or any suitable conductor.

FIG. 2C is an insulation layer 210. The insulation layer 210 is formed of the material of the medium 106 and includes the first reference via 206 and the first anchor vias 208, which extend through the insulation layer 210.

FIG. 2D is a second patterned layer 212. The second patterned layer 212 is formed of the material of the medium 106 and includes the traces 104c, 104d, e.g., formed as channels that contain conductive gel formed in the medium 106. The first reference via 206 and the first anchor vias 208 extend through the second patterned layer 212, and a second reference via 214 and second anchor vias second anchor via 216 are operatively coupled to traces 104c, 104d.

FIG. 2E is an encapsulation layer 218. The encapsulation layer 218 is formed of the material of the medium 106 and includes the first reference via 206, the first anchor vias 208, the second reference via 214, and the second anchor vias 216, all of which are exposed beyond the medium 106 to enable the strain sensor 102 to be operatively coupled to the electronic parameter sensor 112, as shown in FIG. 1.

The various layers are presented for illustration and not limitation and it is to be recognized and understood that any of a variety of additional or alternative layers may be incorporated into the laminate structure as desired. The laminate structure may incorporate at least one substrate layer onto which conductive gel is positioned, at least one patterned layer that forms at least one trace, and at least one encapsulation layer that seals the trace or other component of the laminate structure. The laminate structure may further include: a stencil layer, e.g., for when a stencil-in-place manufacturing process is utilized; a conductive layer for, e.g., a relatively high-powered bus, sensor, ground plane, shielding, etc.; an insulation layer, e.g., between a substrate layer, a conductive layer, a stencil layer, and/or an encapsulation layer, that primarily insulates traces or conductive layers from one another; an electronic component not necessarily formed according to the processes disclosed herein, e.g., a surface mount capacitor, resistor, processor, etc.; vias for connectivity between layers; and contact pads.

The collection of layers of the laminate structure may be referred to as a "stack". A final or intermediate structure may include at least one stack (or multiple stacks, e.g., using modular construction techniques) that has been unitized. Additionally or alternatively, the structure could comprise one or more unitized stacks with at least one electronic component. A laminate assembly may comprise multiple laminate structures, e.g., in a modular construction. The assembly may utilize island architecture including a first laminate structure (the "island"), which may typically but not exclusively be itself a laminate structure populated with electric components, or a laminate structure that is, e.g., a discrete sensor, with the first laminate structure adhered to a second laminate structure including, e.g., traces and vias configured like a traditional printed circuit board ("PCB"), e.g., acting as the pathways for signals, currents or potentials to travel between the island(s) and other auxiliary structures, e.g., sensors.

Figure 3A:
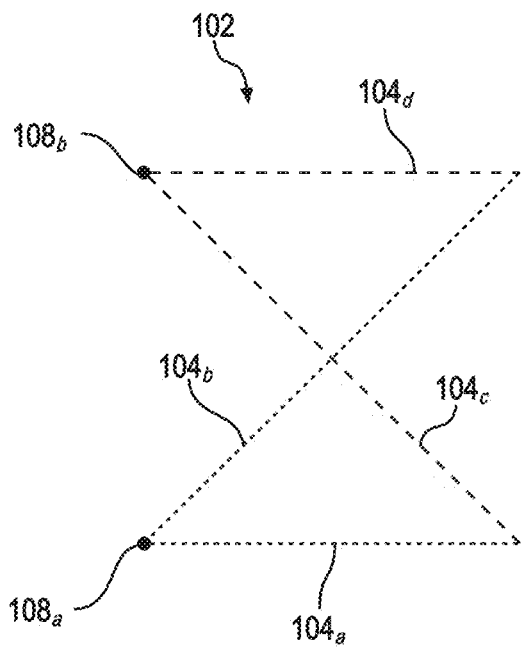
FIGS. 3A and 3B illustrate traces of a strain sensor system in a relaxed condition and a deformed condition, according to at least one non-limiting aspect of the present disclosure.
Figure 3B:
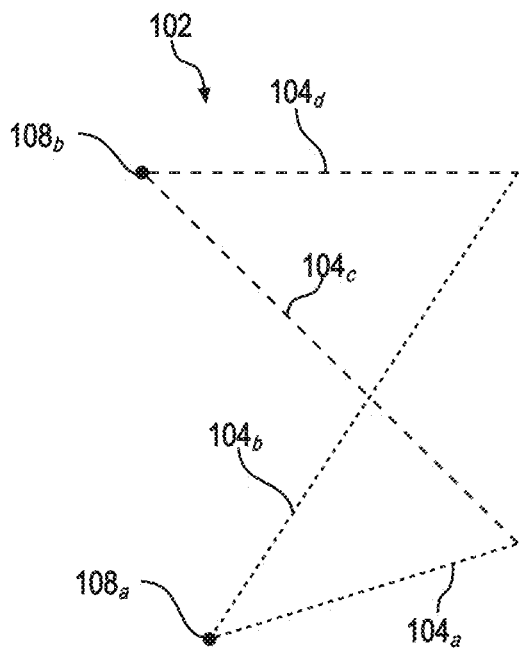

FIGS. 3A and 3B are abstract depictions of the traces of the strain sensor 102 in a relaxed and deformed configuration, respectively. The strain sensor 102 is considered to be in the relaxed configuration when an outside force is not acting on the strain sensor 102 such that the strain sensor 102 deforms through stretching, flexing, etc. The strain sensor 102 is considered to be in the deformed configuration when an outside for is acting on the strain sensor 102 such that the strain sensor 102 deforms through stretching, flexing, etc., and, as a result, one or more of the traces 104a, 104b, 104c, 104d lengthen or contract relative to their length in the relaxed configuration. It is noted that FIGS. 3A and 3B are described in a two-dimensional plane, but it is to be recognized and understood that the principles described with respect to two dimensions apply as well to three dimensional strain placed on the strain sensor 102.

In the illustrated example, in the relaxed configuration the traces 104a, 104d are of substantially equal length, e.g., within five (5) percent, and, as a result, of approximately equal resistance or impedance. Similarly, the traces 104b, 104c are similarly of substantially equal length and, as a result, of approximately equal distance. In such a circumstance, the processor 114 would determine that the relative (x, y) location of the reference points 108a, 108b are in their relaxed state.

In the deformed configuration, an outside force causes the reference point 108a to move relative to the reference point 108b. In the illustrated example, the length, and consequently, resistance of the traces 104c, 104d have not substantially changed, resulting in the processor 114 being configured to determine that, at least on a relative basis, strain has not been placed on the strain sensor 102 proximate the reference point 108b. However, the length, and consequently, the resistance of the traces 104a, 104b have changed, in the case of trace 104a to shorten and in the case of trace 104b to lengthen relative to the length of those traces 104a, 104b in the relaxed state. Consequently, the processor 114 would be configured to determine that a strain has been placed on the strain sensor 102 proximate the reference point 108a.

Strain placed on the strain sensor 102 at different locations would result in different deformation of the strain sensor 102 and, consequently, different lengthening or shortening of the traces 104a, 104b, 104c, 104d than illustrated here. Moreover, while the length of two traces is shown as being constant, any or all of the traces 104a, 104b, 104c, 104d may change length and, consequently, measured resistance. Moreover, the strain sensor 102 may be sensitive to multiple forces placed on the strain sensor 102 to the extent that those different forces manifest at different locations on the strain sensor 102.

Figure 4:
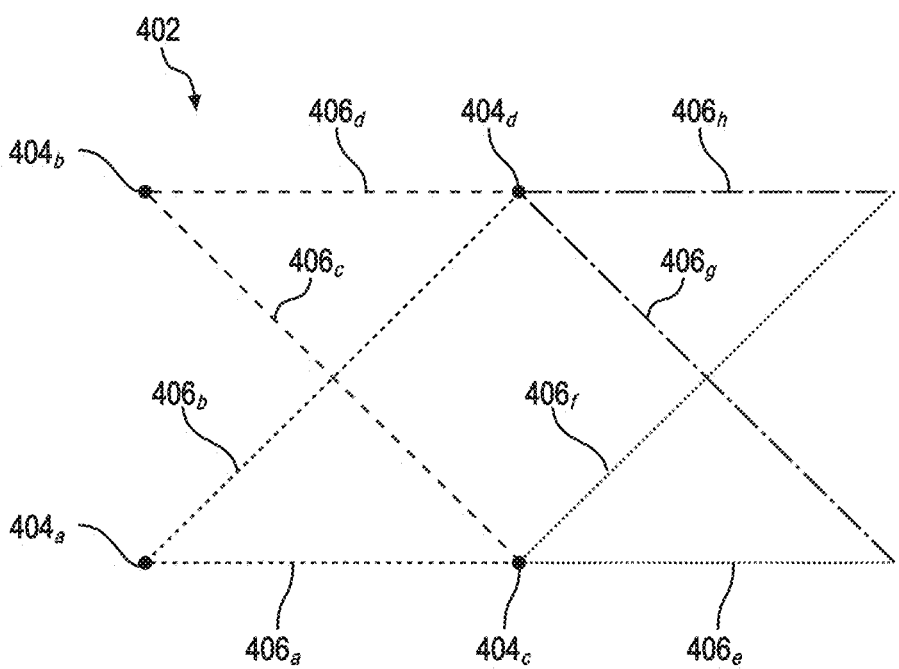
FIG. 4 illustrates another strain sensor, according to at least one non-limiting aspect of the present disclosure.

FIG. 4 is an abstract depiction of a strain sensor 402, in an example aspect. In contrast to the strain sensor 102, the strain sensor 402 includes four reference points 404a, 404b, 404c, 404d. In such an example, the reference points 404c, 404d may function as de facto anchor points in relation to the reference points 404a, 404b. Consequently, the resistance over the trace 406a may be measured from reference point 404a to reference point 404c, and so forth.

The relative position of each reference point 404a, 404b, 404c, 404d are each determined by two of the traces 406. For the sake of clarity, the traces 406 associated with each reference point 404a, 404b, 404c, 404d are denoted by a particular dashed line. Thus, the relative position (x, y) of the reference point 404a is determined based on the resistance of the traces 406a, 406b, the relative position of the reference point 404c is based on the resistance of the traces 406e, 406f, and so forth. The principles disclosed herein are readily expandable to any number of reference points over any given area. The number of inputs on the electronic parameter sensor 112 or ohm meters may be expanded proportionally along with the processing resources of the processor 114.

Moreover, it is to be recognized and understood that number of traces associated with a given reference point may expand based on the available traces. In various examples, the relative position of a reference point may be determined based on three or more traces rather than only two, with the equations described above expanded to incorporate the additional traces. However, in further examples the additional traces beyond two for each reference point 404 may be treated as redundant traces. Thus, the processor 114 may only utilize two traces to determine the relative position of a given reference point, but if a trace to a reference point 404 breaks then the processor 114 may utilize a different, unbroken trace to determine the relative position of the reference point 404.

The inclusion of multiple reference points 404 in a strain sensor and/or multiple strain sensor may provide for the creation of a real-time three dimensional model of a larger object. Thus, for instance, a wearable article may have traces extending throughout the wearable article, with the traces coupled to many reference points distributed throughout the wearable article. By regularly determining the relative position of each reference point, the processor 114 may readily create a three-dimensional model of the wearable article based on the change in relative position of each reference point to neighboring reference points. According to some non-limiting aspects, two-dimensional movement can be monitored via the strain sensor system 100 and correlated to a three-dimensional representation. This is done by correlating a constrained motion system to known two-dimensional displacement data, and by calculating three-dimensional displacements from the two-dimensional outputs of the strain sensor system 100.

Adaptation of the strain sensors disclosed herein to various use cases may result in the length of traces being optimized for the conditions of the wearable article or other article to which the strain sensor is attached. Thus, for instance, some traces may be relatively longer and the reference points spaced apart in certain locations that would not be expected to have strain placed thereon (e.g., along a forearm portion of a sleeve, across a thigh portion of a knee brace, etc.) while other traces may be relatively shorter and reference points spaced closer together in locations that may be expected to have strain placed thereon (e.g., at an elbow of a sleeve, a knee joint of a knee brace, etc.).

Although the sensors of FIGS. 1-4 are described as "strain" sensors, it shall be appreciated that, according to some non-limiting aspects of the present disclosure, those sensors can be used to generate electrical parameters (e.g., an inductance, a resistance, a voltage drop, a capacitance, and an electromagnetic field, etc.) that can be correlated to other physical parameters (e.g., a stress, a pressure, a dimension, etc.) aside from strain. Therefore, it shall be appreciated that, by integrating the aforementioned flexible circuits and deformable conductors into wearable articles (e.g., sleeves, braces, etc.) worn by a user, can generate varying electrical parameters (e.g., an inductance, a resistance, a voltage drop, a capacitance, and an electromagnetic field, etc.) that can be correlated to physical parameters (e.g., a strain, a stress, a pressure, a dimension, etc.) and thus, used to generate highly accurate simulations of the user's motions while wearing the article. Although the sensors of FIG. 1-4 can be implemented in wearable articles, alternate components (e.g., flexible circuits, electrodes, pressure sensors, temperature sensors, etc.) can be useful for integration in a wearable article. For example, as will be illustrated below, various flexible circuits can be implemented to monitor strain along a single axis.

According to some non-limiting aspects, various sensors, including a variety of flexible circuits (e.g., sensors 102, 402 of FIGS. 1-4), can be utilized in conjunction with one or more electrodes integrated into a wearable article, such as those disclosed in U.S. Provisional Patent application Ser. No. 63/235,937, titled BIASING ELECTRODES SLEEVES, filed Aug. 23, 2021, U.S. Provisional Patent application Ser. No. 63/241,806, titled BRACE WITH INERTIAL MEASUREMENT UNITS, filed Sep. 8, 2021, and/or International Patent Application Publication NO. WO2021253050, titled MULTI-AXIS DIFFERENTIAL STRAIN SENSOR, filed Jun. 11, 2021, the disclosures of which are hereby incorporated by reference in their entirety. For example, referring now to FIG. 5, one such electrode 500 is depicted in accordance with at least one non-limiting aspect of the present disclosure. According to the non-limiting aspect of FIG. 5, the electrode 500 can be structurally configured for optimized skin contact. The electrode 500 of FIG. 5 can be electrically configured to measure muscle response and/or electrical activity in response to a nerve's stimulation of the muscle, which in conjunction with the sensors 102, 402 of FIGS. 1-4 can be one of a plurality of signals and/or contribute to an aggregate signal used by the processor 114 (FIG. 1) to characterize motions of a user while wearing the article.

Figure 5:
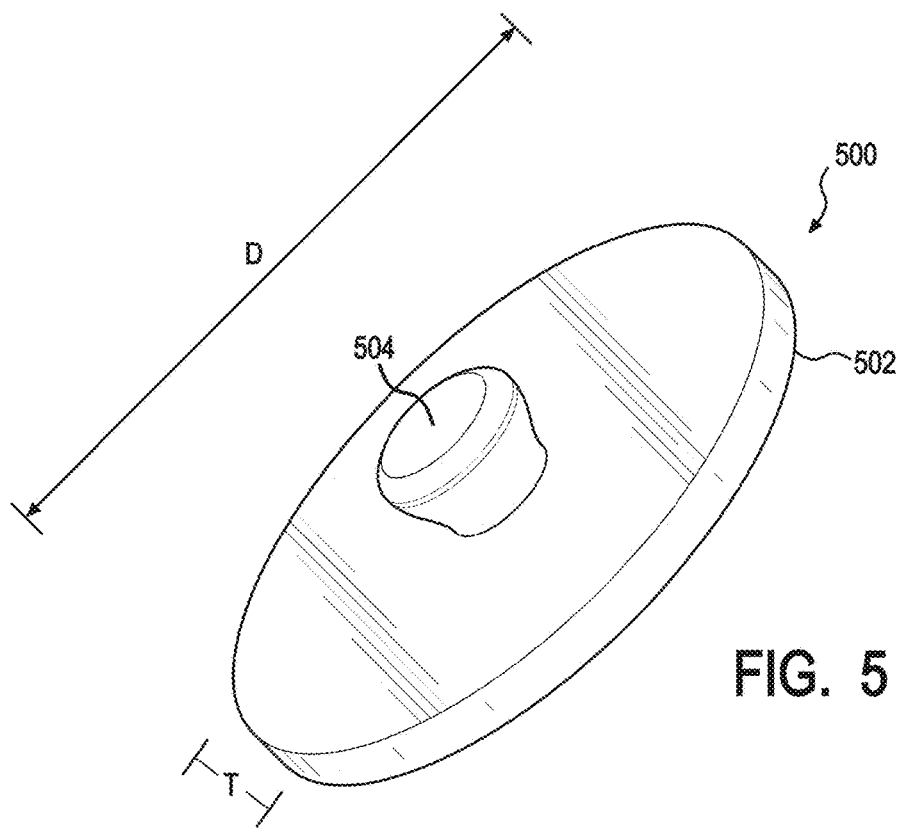
FIG. 5 illustrates an electrode, in accordance with at least one non-limiting aspect of the present disclosure.

Still referring to FIG. 5, the electrode 500 can define a specified diameter D and thickness T, such that the electrode 500 can be properly integrated into the article in a desired manner. Specifically, the diameter D can be dimensioned such that a surface 502 of the electrode 500 configured to contact the user's skin provides sufficient area for the desired sensing capabilities. The electrode 500, further, can include a contact 504 configured to electrically integrate with the sensors 102, 402 (FIGS. 1-4) of a circuit in a desired way, such that the processor 114 (FIG. 1) can receive signals from the sensors 102, 402 (FIGS. 1-4) and electrode 500. Of course, according to other non-limiting aspects, the electrode 500 can be alternately configured. For example, in reference to FIG. 6, another electrode 600 can include a rectangular configuration, with a particularly configured width W and length L that define a surface 602 of sufficient area to enable the desired sensing capabilities. Nonetheless, the electrode 600 of FIG. 6 can once again include a contact 604 configured to electrically integrate with the sensors 102, 402 (FIGS. 1-4) of a circuit in a desired way, such that the processor 114 (FIG. 1) can receive signals from the sensors 102, 402 (FIGS. 1-4) and electrode 600.

Figure 6:
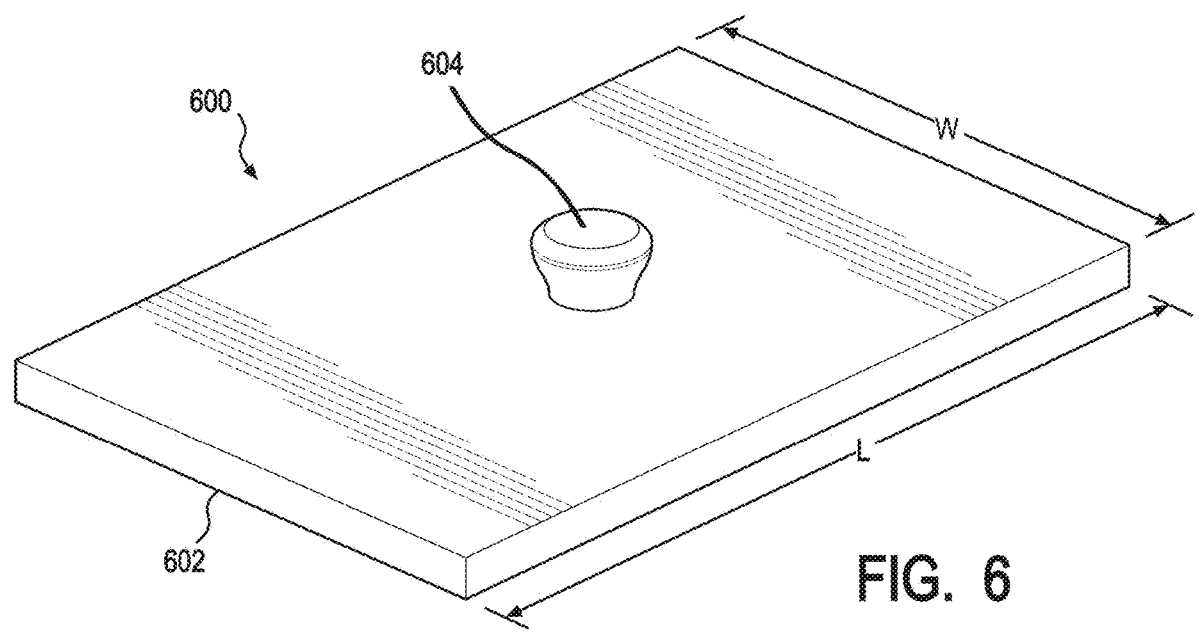
FIG. 6 illustrates another electrode, in accordance with at least one non-limiting aspect of the present disclosure.

In further reference to FIGS. 5 and 6, one challenge associated with the electrodes 500, 600 may be achieving an adequate signal from the sensor and/or electrode in some use cases and conditions. For example, due to the variety of body part sizes that may be contained within the wearable article and the challenge of providing consistent contact with the skin through a broad range of motions, varying pressures may result in variable contact quality between some wearers' skin and the electrodes 500, 600. While the aforementioned exemplary electrode 500, 600 configurations may provide acceptable data and/or signals for monitoring the intended activity in a user's muscle or muscle groups, according to some non-limiting aspects, there may be a need to improve the interface between the aforementioned electrodes 500, 600 and a user's skin.

Figure 7A:
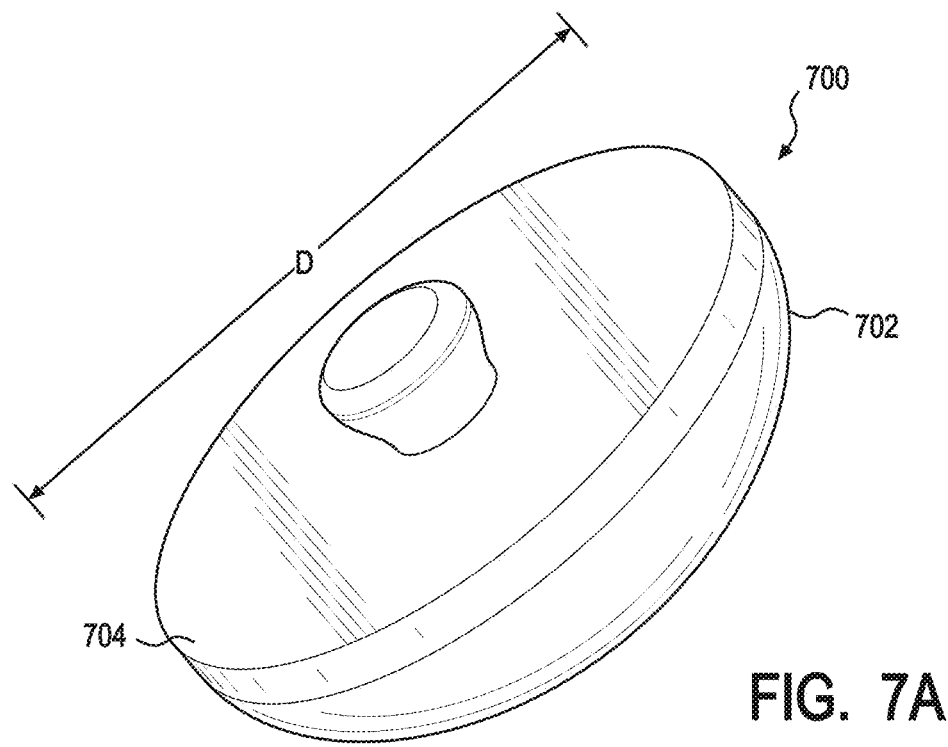
FIGS. 7A and 7B illustrate another electrode, in accordance with at least one non-limiting aspect of the present disclosure.
Figure 7B:
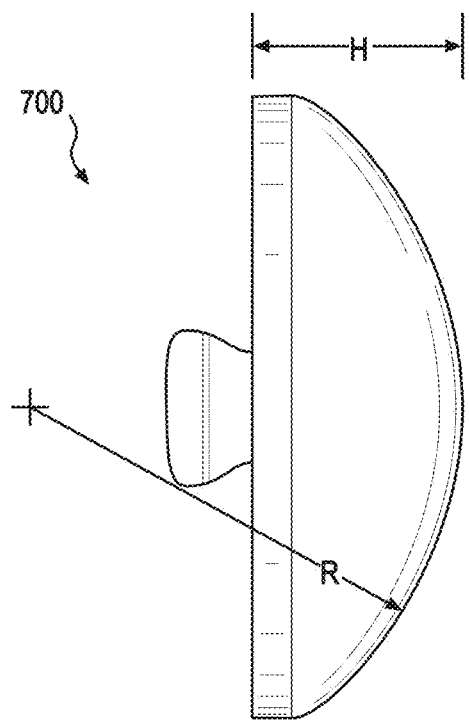

Referring now to FIGS. 7A and 7B, another electrode 700 is depicted in accordance with at least one non-limiting aspect of the present disclosure. The electrode 700 of FIGS. 7A and 7B can be configured similar to the electrode 500 of FIG. 5. However, while a surface 704 of the electrode 700 opposite the skin-contacting surface 702 is flat, according to the non-limiting aspect of FIGS. 7A and 7B, the electrode 700 can have a "pellet" geometry, meaning the skin-contacting surface 702 of the electrode 700 can be convex, as defined by specific radius R and height H. In other words, the electrode 700 of FIGS. 7A and 7B utilizes a domed, spherical, and/or otherwise convex topography to further optimize the skin-contacting area of the surface 702 when integrated into a wearable article. According to some non-limiting aspects, radius R may be dimensioned within an approximate range of 0.25 and 1.75 times—and, preferably, between 0.5 and 1.5 times—a major dimension (e.g. diameter D) of the electrode 700. For example, according to one non-limiting aspect, the electrode 700 can include a diameter D of approximately 13 millimeters, a contact surface curvature radius R of approximately 11.5 millimeters, and a spherical cap height H of approximately 2 millimeters. In other words, the electrode 700 can have a radius R that is 0.88 times the diameter D of the electrode 700, well within the preferred range of 0.50 and 1.50. According to other non-limiting aspects, a length or width of an electrode may be considered a major dimension, as will be discussed in further detail herein. In other words, the electrode 700 of FIGS. 7A and 7B facilitates a larger area for a skin-contracting surface 702.

Figure 8:
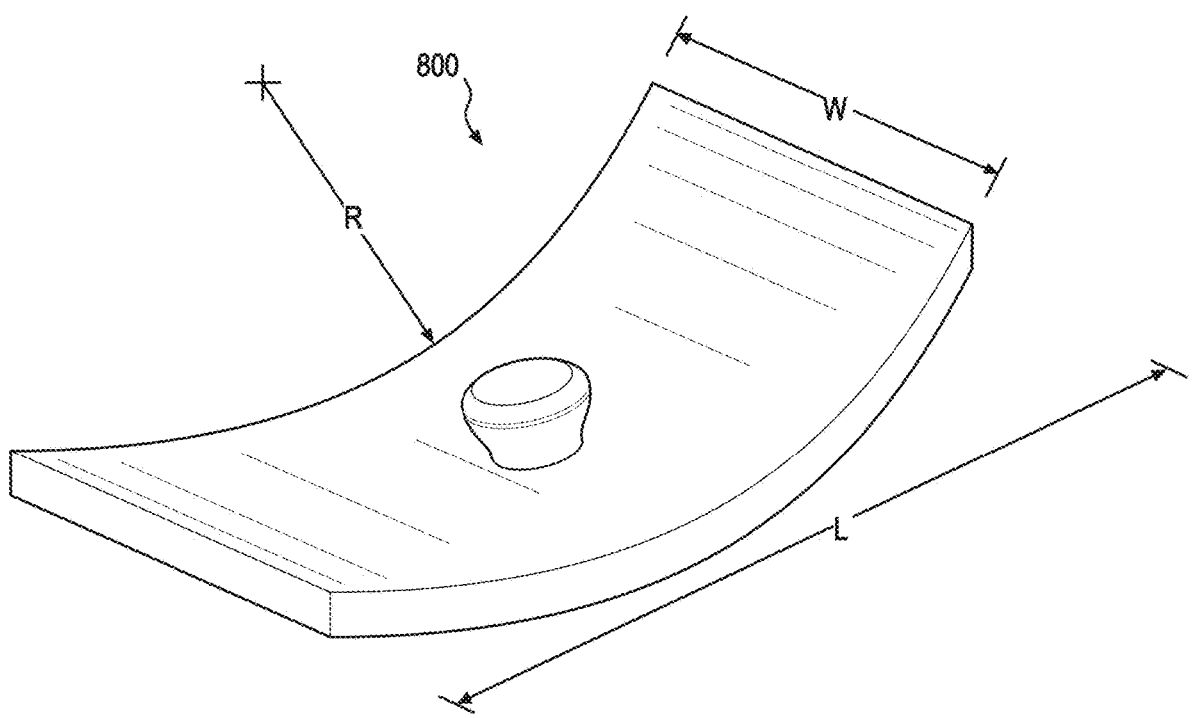
FIG. 8 illustrates another electrode, in accordance with at least one non-limiting aspect of the present disclosure.

Referring now to FIG. 8, another electrode 800 is depicted in accordance with at least one non-limiting aspect of the present disclosure. Similar to the electrode 700 of FIGS. 7A and 7B, the electrode 800 of FIG. 8 can include a "pellet"

geometry, meaning the skin-contacting surface 802 of the electrode 700 can be convex, as defined by specific radius R. However, according to the non-limiting aspect of FIG. 8, a surface 804 of the electrode 800 opposite the skin-contacting surface 802 can be concave, also defined by specific radius R, thereby defining a "leaf-spring," or "cupped" geometry across length L, with a flat geometry along its width W. The electrode 800 of FIG. 8 can be molded and/or otherwise formed to have a radius R of curvature that extends along substantially an entire length L or width W of the sheet, either of which may be considered a major dimension for purposes of determining the desired dimension of radius R. For example, according to the non-limiting aspect of FIG. 8, the major diameter may be length L, since the radial R axis extends in along the width W. However, according to other non-limiting aspects, it may be desirable to extend the radius R in the lengthwise direction, in which case the major dimension can be width W. Unlike the electrode 700 of FIGS. 7A and 7B, the curvature defined by electrode 800 is hollow and unbound on some sides and thus, the resulting structure of electrode 800 can behave much like a leaf spring when integrated into a wearable article (e.g., a brace, a sleeve, etc.), as shown in FIGS. 10-12. In other words, the structure of electrode 800 not only increases the area of a skin-contacting surface 802, but allows the electrode 800 to deform under pressure. Accordingly, the electrode 800 of FIG. 8 can be configured to provide a biasing force against the wearer's skin in response to the radial compression force, as supplied by the wearable article when stretched over a respective portion of a wearer's body. Thus, the electrode 800 can improve contact quality between the skin-contacting surface 802 and skin of a user and therefore, can produce more accurate signals and/or data.

Figure 9A:
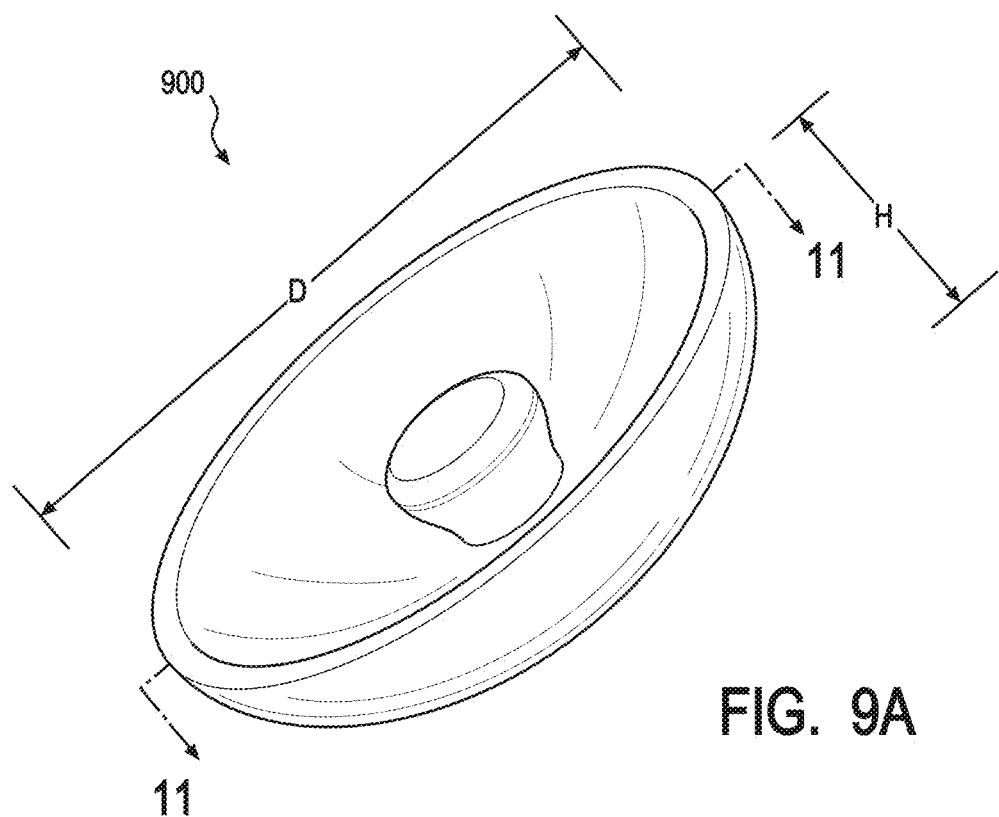
FIGS. 9A and 9B illustrate another electrode, in accordance with at least one non-limiting aspect of the present disclosure.
Figure 9B:
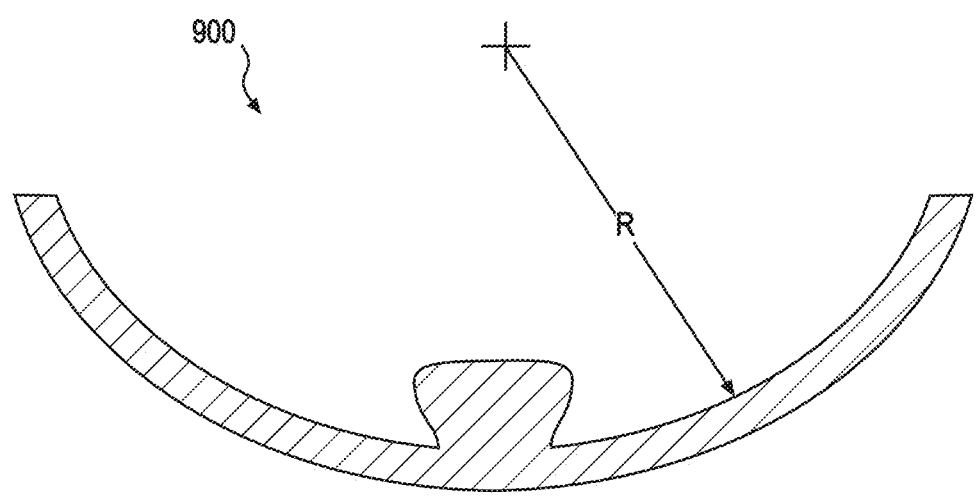

The present disclosure contemplates alternatives to the "leaf spring" electrode 800 configuration of FIG. 8. For example, the electrode 900 of FIGS. 9A and 9B can include a skin-contacting surface 902 of the that is convex, as defined by specific radius R. However, according to the non-limiting aspect of FIGS. 9A, and 9B, a surface 904 of the electrode 900 opposite the skin-contacting surface 802 can be concave in all directions (e.g., its length and width), as defined by specific radius R. In other words, the electrode 900 of FIGS. 9A and 9B can define a "dome-like" or "cupped" geometry. Although the electrode 900 of FIGS. 9A and 9B is bound on all sides by the defined dome, unlike the electrode 700 of FIGS. 7A and 7B, it is hollow and thus, can produce a "leaf-spring" biasing effect. Similar to the electrode of FIG. 8, when integrated into a brace or sleeve, the flexibility provided by the electrode 900 of FIG. 9, in combination with the domed curvature, produces a spring-like effect under pressure which can bias the electrode against the user's skin, thereby improving the performance of the electrode 900.

The circular shape of FIGS. 9A and 9B is merely illustrative and it shall be appreciated that the present disclosure contemplates other non-limiting aspects wherein any of the electrodes disclosed herein include various alternate geometries (e.g., rectangular, triangular, hexagonal, etc.) while achieving a similar biasing effect. According to the present disclosure, any shape of electrode can be configured with a protruding geometry similar to the dome of FIGS. 9A and 9B, including various spherical topographies. According to the non-limiting aspect of FIGS. 9A and 9B, the major dimension of the electrode 900 can be diameter D. However, according to other non-limiting aspects where the electrode 900 includes a square or rectangular geometry, either a length or width of the electrode can serve as the major dimension for purposes of calculating the desired radius, as previously disclosed.

The present disclosure further contemplates non-limiting aspects wherein an electrode biasing effect is provided not only by the electrode structure (e.g., structure of electrodes 800, 900), but by the wearable article itself. For example, an fluid-fillable circuit can be integrated into the wearable article and filled with varying quantities of fluid, thereby expanding a thickness of the wearable article in certain predetermined portions and thus, increasing the pressure with which any electrode (e.g., electrodes 500, 600, 700, 800, 900 of FIGS. 5, 6, 7A, 7B, 8, 9A, and 9B) contacts the user's skin. According to some non-limiting aspects, the fluid-fillable circuits can be similar to those described in U.S. Provisional Application No. 63/272,487, titled DEVICES, SYSTEMS, AND METHODS FOR MAKING AND USING A FLUID-FILLABLE CIRCUIT, filed Oct. 27, 2021, the disclosure of which is hereby incorporated by reference in its entirety.

The electrodes 700, 800, 900 of FIGS. 7A, 7B, 8, 9A, and 9B can enhance reliability and improve signal quality generated by electrodes 500, 600 of FIGS. 5 and 6. Since, according to some non-limiting aspects, a wearable article (e.g., a brace, a sleeve, etc.) can include a tubular configuration, radial pressure may be applied to the back side of conventional electrodes. This can result in an associated deflection of the user's skin at the surface contact between a contact surface of an electrode and the user's body. Instances where there is a mismatch or less than optimal pairing between the selected brace or sleeve size and the wearer's body member size, a reliable contact interface between the sensor and the wearer's skin may not be achieved. This may be particularly problematic when the selected brace or sleeve size provides a preferred level of fit or comfort to the wearer, but suboptimal reliability or consistency in the interface between the wearer's skin and the electrode. This may be due to a variety of factors, some of which are related. For example, insufficient deflection of the user's skin may not produce adequate or reliable contact with the sensor, and/or the brace or sleeve may not produce sufficient radial force to enable adequate or reliable contact with the sensor.

The various protruding (e.g., concave, convex, etc.) features depicted via the electrodes 700, 800, 900 of FIGS. 7A, 7B, 8, 9A, and 9B can provide skin-contacting surfaces 702, 802, 902 that are larger relative to the skin-contacting surfaces 502, 602 of the more planar or flat electrodes 500, 600 of FIGS. 5 and 6. This can result in relatively larger skin-contacting surface areas that, according to some non-limiting aspects, can range between approximately 100 millimeters and 200 square millimeters. For example, according to some preferred non-limiting aspects of the present disclosure, the skin-contacting surface 702, 802, 902 areas of FIGS. 7A, 7B, 8, and 9 can be approximately 145 square millimeters, as opposed to a planar electrode (e.g., electrode 500 of FIG. 5) with a skin-contacting surface that defines a similar outer diameter but only has a surface area of only approximately 133 square millimeters. Thus, it shall be appreciated that an additional advantage of providing the curved skin-contacting surfaces 702, 802, 902 of FIGS. 7A, 7B, 8, and 9 is the ability to provide a larger area for a given form factor or "footprint" of the electrode 700, 800, 900, further improving the accuracy of signals produced by the electrodes 700, 800, 900.

In further reference to FIGS. 7A, 7B, 8, and 9, a protrusion provided by curved skin-contacting surfaces 702, 802, 902 relative to the surrounding surfaces of a wearable article (e.g., sleeve, brace, etc.) may subtly concentrate the radial compressive forces of the brace on the wearer's skin at a preferred electrode 700, 800 location. According to some non-limiting aspect, the resulting compressive forces can cause increased deflection and improved contact between the sensor and the wearer. As previously noted, various electrodes 500, 600, 700, 800, 900 can be integrated with one or more sensors, such as the sensors 102, 402 of FIGS. 1-4, into a wearable article. According to some non-limiting aspects, electrodes and sensors can be integrated into a wearable article via the means disclosed in U.S. Provisional Patent application Ser. No. 63/235,937, titled BIASING ELECTRODES SLEEVES, filed Aug. 23, 2021, U.S. Provisional Patent Application No. 63/241,806, titled BRACE WITH INERTIAL MEASUREMENT UNITS, filed Sep. 8, 2021, and/or International Patent Application Publication NO. WO2021253050, titled MULTI-AXIS DIFFERENTIAL STRAIN SENSOR, filed Jun. 11, 2021, the disclosures of which are hereby incorporated by reference in their entirety. A few non-limiting examples of wearable articles 1000, 1100, 1200 configured to accommodate electrodes, such as the electrodes 500, 600, 700, 800, 900 of FIGS. 5, 6, 7A, 7B, 8, 9A, and 9B, and sensors, such as the sensors 102, 402 of FIGS. 1-4, are depicted in FIGS. 10-12. Thus, the electrodes 500, 600, 700, 800, 900 can be used to monitor and even diagnose conditions affecting muscles in an applied region, because they can generate electrical outputs during a use (e.g., physical therapy, virtual reality implementation, etc.).

The electrodes 500, 600, 700, 800, 900 of FIGS. 5, 6, 7A, 7B, 8, 9A, and 9B can include sophisticated active amplifiers and/or filters. According to some non-limiting aspects, the amplifiers and/or filters in the electrodes 500, 600, 700, 800, 900 can be formed using a "soft solder" process in a highly-pliable TPU film of a flexible circuit. Thus, a wearable article can pull voltages from skeletal muscle tissue via the electrodes 500, 600, 700, 800, 900 (e.g., dry electrodes), which can be directly adhered to the TPU film of the flexible circuit, resulting in a flexible, stretchable, filly conformable, active circuit. According to some non-limiting aspects, wherein the wearable article is an active prosthetic, it shall be appreciated that the electrodes 500, 600, 700, 800, 900 can be configured to control the prosthetic. As such, the electrodes 500, 600, 700, 800, 900 can detect pulses within a user's muscle and thus, monitor the user's attempts to move their muscles, joints, and/or appendages. The flexible circuits and other components disclosed herein can thus compare that data to sensed positional data (e.g., data generated by an IMU, data generated by a strain gauge, etc.) to assess an effort of the user and the results being generated by the user's effort.

According to some non-limiting aspects, it shall be appreciated that the electrodes 500, 600, 700, 800, 900 (FIGS. 5, 6, 7A, 7B, 8, 9A, and 9B) along with the other components disclosed herein—can be used to control a robotic device. For example, the electrodes can monitor a user's efforts, which can be used in conjunction with sensed positional data (e.g., data generated by an IMU, data generated by a strain gauge, etc.) not only simulate the user's motions while wearing the joint monitoring sleeve 1500, but replicate those motions via a connected robotic device that serves as an artificial reproduction of the user's joint and/or appendage within the joint monitoring sleeve 1500.

Any of the electrodes 500, 600, 700, 800, 900 (FIGS. 5, 6, 7A, 7B, 8, 9A, and 9B) can be formed using a variety of operations, including injection molding, casting, or any other suitable technique, depending on the materials used to form the electrode and the desired characteristics or biasing effect necessary for a resulting sensor integration into a wearable apparatus, such as the wearable articles 1000, 1100, 1200 of FIGS. 10-12.

Moreover, it shall be appreciated that any of the electrodes 500, 600, 700, 800, 900 (FIGS. 5, 6, 7A, 7B, 8, 9A, and 9B) disclosed herein can be of a dry, wet, and/or passive-type configuration. According to some non-limiting aspects, the electrodes 500, 600, 700, 800, 900 can employ a conductive gel, similar to the aforementioned deformable conductors, as described in reference to the sensors 102, 402 and flexible circuits of FIGS. 1-4. According to some non-limiting aspects, a wet configuration may be preferable to provide the most reliable signal, although wet electrodes can be less convenient and/or comfortable for a user over an extended period of use due to the use of conductive gels. As such, other non-limiting aspects, dry electrodes can be integrated into the wearable article. According to other non-limiting aspects, the electrodes 500, 600, 700, 800, 900 can include a flexible, dry silver nanowire configuration embedded in a polymer (e.g., polydimethylsiloxane ("PDMS"), etc.), as those described in U.S. patent application Ser. No. 15/127, 455, titled ELECTRODES AND SENSORS HAVING NANOWIRES, filed on Apr. 7, 2015, the disclosure of which is hereby incorporated by reference in its entirety. However, according to other non-limiting aspects, the electrodes 500, 600, 700, 800, 900 can include silver and/or silver chloride pellet-type electrodes (e.g., J&J Engineering's SE-12 and SE-13, etc.). Of course, according to still other non-limiting aspects, a variety of other electrode types can be formed into the configurations of FIGS. 5-9. The foregoing examples are merely provided for illustrative purposes.

Regardless, it shall be appreciated the aforementioned electrodes 500, 600, 700, 800, 900 of FIGS. 5, 6, 7A, 7B, 8, 9A, and 9B, though different in configuration, can be used to gather similar biometric data and signals when integrated into the wearable articles contemplated herein. For example, according to some non-limiting aspects, the electrodes can have a circular contact area having a diameter of approximately 8 millimeters (e.g., J&J Engineering's SE-12, etc.). According to other non-limiting aspects, the electrodes can include a larger diameter of approximately 17 millimeters (e.g., J&J Engineering's SE-13, etc.).

According to non-limiting aspects where the electrodes 500, 600, 700, 800, 900 (FIGS. 5, 6, 7A, 7B, 8, 9A, and 9B) include a silver nanowire type configuration, a variety of geometric shapes and sizes can be selected, as the present disclosure is not dimensionally limited. For example, according to some preferable aspects, the electrodes 500, 600, 700, 800, 900 include a silver nanowire type configuration and define a surface contact area of at least about 20 square millimeters. For example, according to such aspects, the electrode 500, 600, 700, 800, 900 can include a circular contact area having a diameter of approximately 5 millimeters, or a rectangular contact area having a width and length of approximately 4.5 millimeters. According to other preferable aspects, the electrode 500, 600, 700, 800, 900 can define a contact area of approximately 130 square millimeters. For example, according to such aspects, the electrode 500, 600, 700, 800, 900 can include a circular contact area having a diameter of approximately 13 millimeters, or a rectangular contact area having a width and length of approximately 11.5 millimeters. According to still other non-limiting aspects, the electrodes 500, 600, 700, 800, 900 can define a surface area as large as 900 square millimeters.

For example, according to such aspects, the electrode 500, 600, 700, 800, 900 can include a circular contact area having a diameter of approximately 34 millimeters, or a rectangular contact area having a width and length of approximately 30 millimeters.

According to some non-limiting aspects, a wearable article (e.g., wearable articles 1000, 1100, 1200 of FIGS. 10-12) can be configured to monitor and/or measure activity of a particular muscle group that requires a larger contact area. In such non-limiting aspects, the contact area for the electrode 500, 600, 700, 800, 900 (FIGS. 5, 6, 7A, 7B, 8, 9A, and 9B) can be limited by the available area of the wearable article, which must also account for any sensors, flexible circuitry, and/or additional electronics to generate and process signals associated with electrical parameters that can be correlated to physical parameters and thus, motion of the wearable article (e.g., pliability, flexibility, stretchability, etc.). Accordingly, it shall be appreciated that the sensor 102, 402 (FIGS. 1-4), electrode 500, 600, 700, 800, 900 (FIGS. 5, 6, 7A, 7B, 8, 9A, and 9B), and wearable article 1000, 1100, 1200 (FIGS. 10-12) configurations disclosed herein are merely illustrative and not intended to be limiting. In other words, the wearable article 1000, 1100, 1200 (FIGS. 10-12) and its respective electronic components can be specifically tailored for a particular joint or body part of interest.

Referring now to FIG. 10, one such wearable article 1000 is depicted in accordance with at least one non-limiting aspect of the present disclosure. According to the non-limiting aspect of FIG. 10, the wearable article 1000 can be configured as a joint monitoring sleeve of a tubular configuration defined by a predetermined diameter D. It shall be appreciated that, as used herein, the term "joint monitoring sleeve" includes a wearable article configured to monitor the movements of any joint (e.g., knee, elbow, shoulder, wrist, ankle, hip, etc.) and/or appendage (e.g., arm, leg, finger, toe, neck, back, etc.). The diameter D can be particularly configured such that the joint monitoring sleeve 1000 can be worn around the desired joint and/or appendage. Although the joint monitoring sleeve 1000 of FIG. 10 is depicted with a plurality of electrodes 1004, 1006, it shall be appreciated that, according to some non-limiting aspects, the joint monitoring sleeve 1000 can further include sensors (e.g., the sensors 102, 402 of FIGS. 1-4) and/or other electronic components (e.g., force sensors, inductive coil sensors, temperature sensors, etc.). The electronic components, including electrodes 1004, 1006 can be electrically coupled using flexible circuits composed of deformable conductors, as previously disclosed.

In further reference to the non-limiting aspect of FIG. 10, any number of electrodes 1004, 1006 integrated onto the joint monitoring sleeve 1000 can include any of the configurations discussed in reference to FIGS. 5, 6, 7A, 7B, 8, and 9. For example, some electrodes 1004 can include a rectangular configuration, such as the electrodes 600, 800 of FIGS. 6 and 8, and some electrodes 1006 can include a circular configuration, such as the electrodes 500, 700, 900 of FIGS. 5, 7A, 7B, 9A, and 9B. Additionally, any of the electrodes 1004, 1006 can include a protruding skin-contacting surface, such as the electrodes of FIGS. 7A, 7B, 8, 9A, and 9B, thereby imbuing the electrodes 1004, 1006 with the previously discussed biasing effects. For example, referring now to FIG. 11, wearable article 1100 is depicted in accordance with at least one non-limiting aspect of the present disclosure. According to the non-limiting aspect of FIG. 11, the wearable article can be configured as a joint monitoring sleeve 1100 can include at least one electrode 1102 with a configuration similar to the electrode 900 of FIGS. 9A and 9B. Likewise FIG. 12 depicts another wearable article 1200 configured as a joint monitoring sleeve that includes at least one electrode 1202 with a configuration similar to electrode 800 of FIG. 8. Accordingly, the joint monitoring sleeves 1000, 1100, 1200 of FIGS. 10-12 can include various electrode 1004, 1006, 1102, 1202 configurations that—in conjunction with the aforementioned flexible circuits, deformable conductors, sensors 102, 402 (FIGS. 1-4), and other electronics (e.g., ohm meter 112 and/or processor 114 of FIG. 1, etc.)—can generate electrical parameters, which can be correlated to physical parameters associated with a user's physical movements while wearing the joint monitoring sleeves 1000, 1100, 1200.

For example, range of motion during flexion of a joint or appendage can be a key indicator of health, especially as a patient is rehabilitating. The joint monitoring sleeves 1000, 1100, 1200 of FIGS. 10-12 utilize electrodes 1004, 1006, 1102, 1202 and/or additional electronics, which can actively monitor the patient's flexibility and motion with enhanced accuracy. For example, the electrodes 1004, 1006, 1102, 1202 and/or sensors 102, 402 (FIGS. 1-4) can be implemented via flexible conductors featuring deformable conductors (e.g., fluid metal gel traces, etc.), which is uniquely configured to move with the joint. Additionally, due to the deformable nature of the conductors employed by such flexible circuits, the joint monitoring sleeves 1000, 1100, 1200 will experience limited and, according to some non-limiting aspects, zero degradation over thousands of strain cycles. Accordingly, no calibration is necessary to ensure accurate results via the joint monitoring sleeves 1000, 1100, 1200 of FIGS. 10-12.

According to some non-limiting aspects, the joint monitoring sleeves 1000, 1100, 1200 can further include a pressure sensor positioned at a location of interest (e.g., the front of a patient's shin, etc.), such that the joint monitoring sleeves 1000, 1100, 1200 can measure swelling at the location of interest. According to some non-limiting aspects, the pressure sensor can be configured similar to the strain sensors 102, 402 of FIG. 1-4. According to other non-limiting aspects, the pressure sensor can include any of those described in International Patent application Ser. No. PCT/US2021/071374, titled WEARABLE ARTICLE WITH FLEXIBLE INDUCTIVE PRESSURE SENSOR, filed Sep. 3, 2021, U.S. Provisional Application No. 63/270,589, titled FLEXIBLE THREE-DIMENSIONAL ELECTRONIC COMPONENT, filed Oct. 22, 2021, and U.S. Provisional Application No. 63/272,487, titled DEVICES, SYSTEMS, AND METHODS FOR MAKING AND USING A FLUID-FILLABLE CIRCUIT, filed Oct. 27, 2021, the disclosures of which are hereby incorporated by reference in its entirety. Accordingly, as an inductive coil in the sensor is depressed or extended, an electrical parameter (e.g., an electromagnetic inductance, etc.) generated by the sensor will vary and corresponding signals can be transmitted via the circuits to the processor 114 (FIG. 1) for characterization of swelling at the location of interest, as detected by the pressure sensor. Of course, according to other non-limiting aspects, alternative pressure sensors (e.g., strain gauges, thin film pressure sensors, variable capacitance pressure sensors, etc.) can be implemented to achieve a similar effect.

In still other non-limiting aspects, the joint monitoring sleeves 1000, 1100, 1200 can include a temperature sensor constructed from the aforementioned deformable conductors. Such conductors can undergo deformations when exposed to temperature gradients, which can result in a differential between electrical parameters generated across the circuit. For example, as temperature at a monitored location changes, the deformable conductor or the encapsulation structure can either expand or contract and a change in the measured resistance across the deformable conductor can be correlated to a change in temperature. Such differentials can be processed by a connected processor 114 (FIG. 1) and correlated to temperature changes in the joint or appendage at the location of the temperature sensor, which can be indicative of a change in blood flow.

Figure 13:
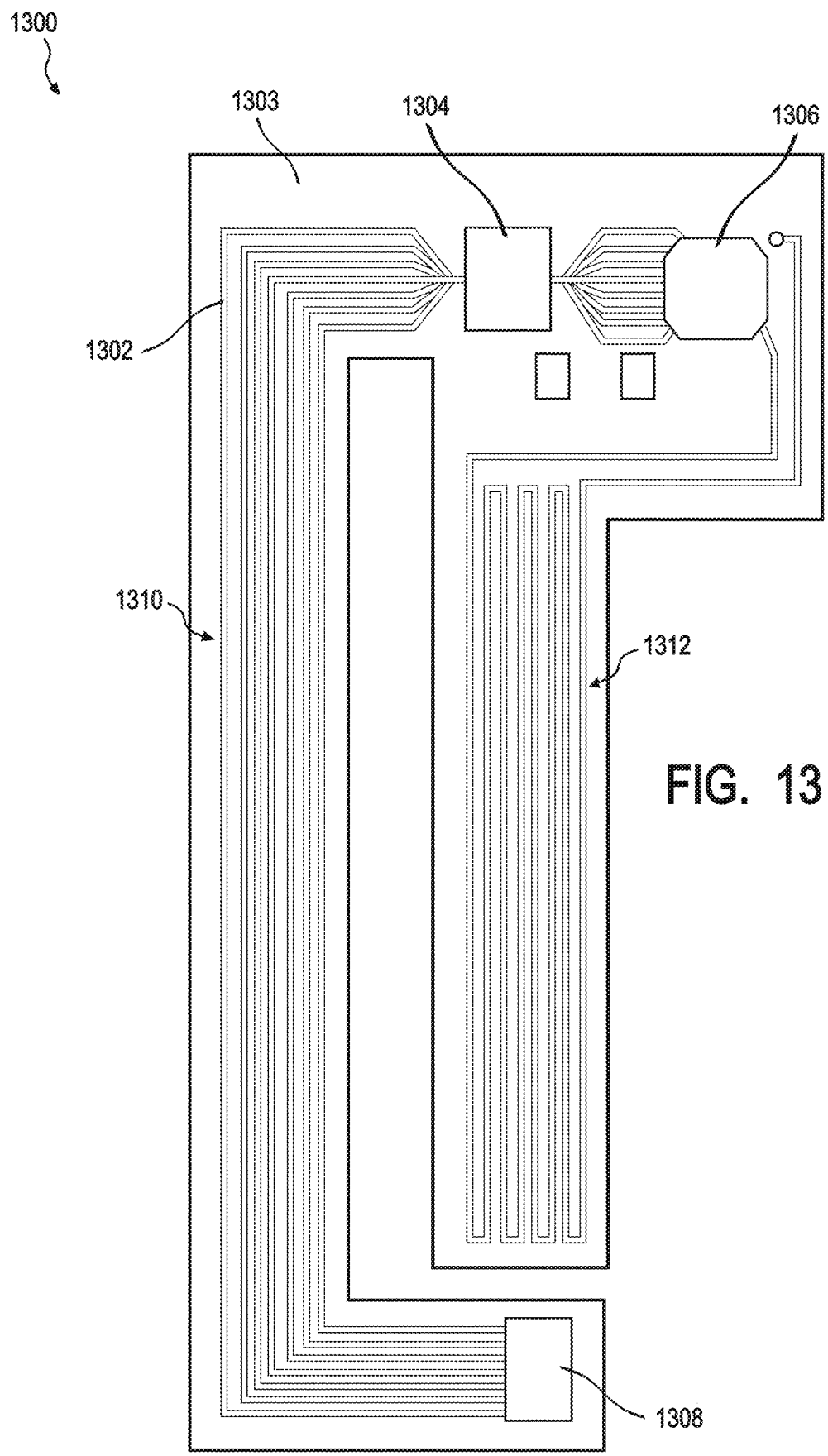
FIG. 13 illustrates a flexible circuit configured to be integrated into a wearable article, in accordance with at least one non-limiting aspect of the present disclosure.

Referring now to FIG. 13, a flexible circuit 1300 configured to be integrated into a wearable article is depicted in accordance with at least one non-limiting aspect of the present disclosure. According to the non-limiting aspect of FIG. 13, the flexible circuit 1300 can include one or more traces 1302 formed from a deformable conductor, such as those disclosed in International Patent application Ser. No. PCT/US2017/019762 titled LIQUID WIRE, which was filed on Feb. 27, 2017 and published on Sep. 8, 2017 as International Patent Publication No. WO2017/151523A1, the disclosure of which is hereby incorporated by reference in its entirety. The traces 1302 can be deposited on a medium 1303, such as those disclosed in U.S. Patent Application Publication No. 2020/0381349, titled "CONTINUOUS INTERCONNECTS BETWEEN HETEROGENEOUS MATERIALS," and filed May 28, 2019, the disclosure of which is hereby incorporated by reference in its entirety. According to some non-limiting aspects, the flexible circuit 1300 can be constructed in accordance with the techniques disclosed in U.S. Patent Application Publication No. 2020/0066628, titled "STRUCTURES WITH DEFORMABLE CONDUCTORS," and filed Aug. 22, 2018, the disclosure of which is hereby incorporated by reference in its entirety. For example, according to some non-limiting aspects, traces 1302 of the strain gauges disclosed herein can be constructed from the previously discussed fluid-phase conductors, which may produce predictable, measurable changes in the electrical characteristics of the trace with little to no hysteresis upon returning to a relaxed state. However, according to other non-limiting aspects, alternate conductors (e.g., silver ink, etc.) can be used, but may experience no hysteresis (or measurable changes in electrical characteristics) upon returning to a relaxed state after undergoing a number of deformation cycles. As will be discussed, the methods of calibration (e.g., method 2200) disclosed herein can enhance the accuracy and reliability of flexible circuits that utilize alternate conductors.

Still referring to FIG. 13, the flexible circuit 1300 can further include a processor 1304 electrically coupled to at least one IMU 1308 via a serial communication bus 1310 (e.g., an I2C protocol, etc.). One or more of the traces 1302 can be specifically configured to form a strain gauge 1312 portion of the flexible circuit 1300 electrically coupled to a multi-gauge, low-power, sensor 1306. According to some non-limiting aspects, the strain gauge 1312 and sensor 1306 can be configured to measure strain throughout the flexible circuit 1300 similar to the sensors 102, 402 of FIGS. 1-4. Moreover, the strain gauge 1312 and sensor 1306. According to some non-limiting aspects, electrical parameters generated by the strain gauge 1312 can be correlated to IMU data generated by the IMU 1308 as the flexible circuit 1300 moves and thus, used to calibrate the IMU 1308. Although the flexible circuit 1300 of FIG. 13 lacks some of the functionality discussed in reference to the joint monitoring sleeves 1500, 1600 of FIGS. 15-17, the flexible circuit 1300 of FIG. 13 presents an integrated and streamlined circuit that combines at least some functionality onto the medium 1303, which functions as a single, laminate structure. This can further promote efficiency, affordability, ease of manufacture, and a more simplistic integration into a wearable article. According to other non-limiting aspects a single, laminate structure can be used to integrate any of the components and/or functionality disclosed herein, including those discussed in reference to FIGS. 15-17. As such, according to some non-limiting aspects, a circuit 1300 construction similar to that of FIG. 13 can provide the aforementioned benefits in conjunction with the enhanced functionality of the joint monitoring sleeves 1500, 1600 of FIGS. 15-17.

For example, according to the non-limiting aspect wherein a wearable article is configured as a joint monitoring sleeve to be worn about a user's knee, at least two or more IMUs 1308 can be positioned on either side of the patella and the strain gauge 1312 can be configured to traverse the patella of the knee, across a portion of the joint monitoring sleeve between each IMU 1308. Accordingly, as the user bends their leg while wearing the joint monitoring sleeve on their knee, the strain gauge 1312 can measure strain across the patella of the user's knee, as the flexible circuit 1300 expands and contracts from the motion of the user's leg across a variety of angles. This data can be correlated to the angular relationship between calibration points, by assuming linear strain, which can be measured by the traces 1302 formed of the deformable conductor and accurately correlated to the motion of the body part adorning the joint monitoring sleeve. Additionally, the IMUs 1308 can add a symbiotic measure of angle and can supplement strain data by monitoring the rotation of a joint and/or hyper expansion beyond set points of the strain gauge 1312. According to some non-limiting aspects the IMUs 1308, themselves, can include flexible circuitry interconnects that are configured to supplement and/or act in lieu of the strain gauge 1312 and thus, fluid-phase conductors can imbue the IMUs 1308 with enhanced accuracy relative to conventional IMUs.

Referring now to FIGS. 14A-D, several other flexible circuits 1400, 1420, 1430 are depicted in accordance with at least one aspect of the present disclosure. Similar to the flexible circuit 1300 of FIG. 13, the flexible circuits 1400, 1420, 1430 of FIGS. 14A-D can include one or more traces 1402 formed from a deformable conductor deposited on a medium 1403 and can be constructed in accordance with the techniques disclosed in U.S. Patent Application Publication No. 2020/0066628, titled "STRUCTURES WITH DEFORMABLE CONDUCTORS," and filed Aug. 22, 2018, the disclosure of which is hereby incorporated by reference in its entirety. Additionally, the flexible circuit 1400 of FIGS. 14A and 14B can further include one or more sensors (e.g., sensors 102, 402 of FIGS. 1-4) and/or other electronic components (e.g., IMU's, processors, force sensors, inductive coil sensors, temperature sensors, etc.). The electronic components, including electrodes 1004, 1006 can be electrically coupled using flexible circuits composed of deformable conductors, as previously disclosed. According to some non-limiting aspects, the deformable conductors can be configured as a bus (e.g., bus 1310 of FIG. 13) portion of the flexible circuit 1400 and/or a strain gauge (e.g., strain gauge 1312 of FIG. 13) portion of the flexible circuit 1400.

Figure 14A:
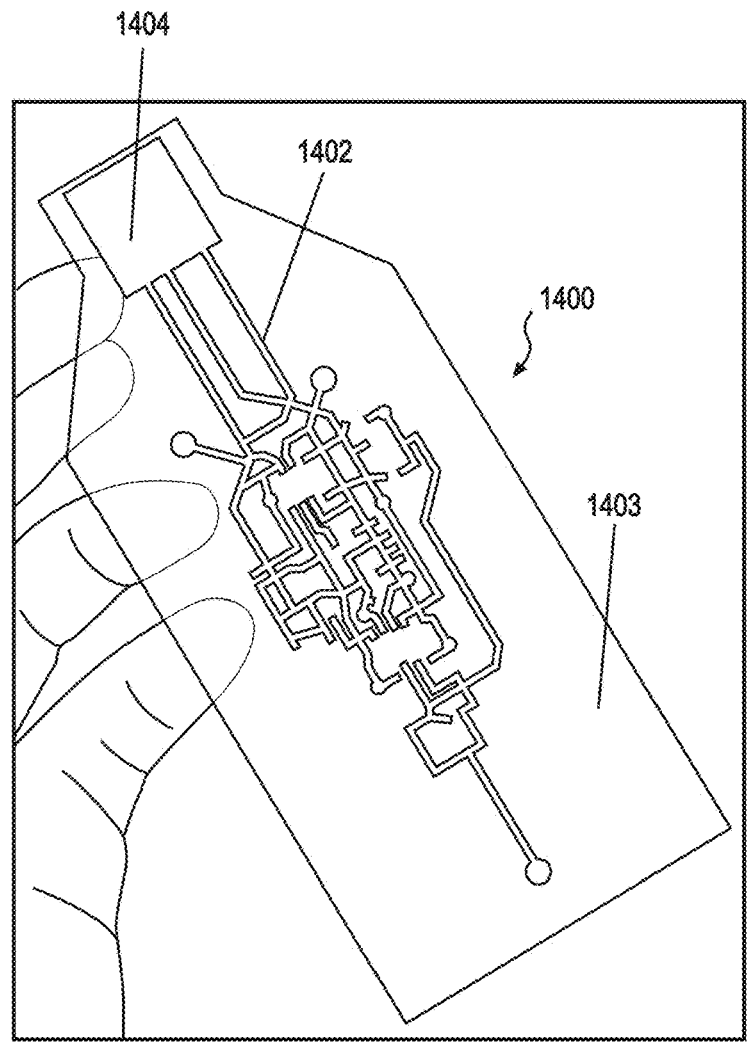
FIGS. 14A-D illustrate several other flexible circuits, in accordance with at least one aspect of the present disclosure.

According to some non-limiting aspects, the flexible circuit 1400 of FIG. 14A can be configured to interface with various electrodes integrated within the wearable article and electrically couple them to other portions of the circuits 1400, 1420, 1430 disposed throughout the wearable article.

Figure 14B:
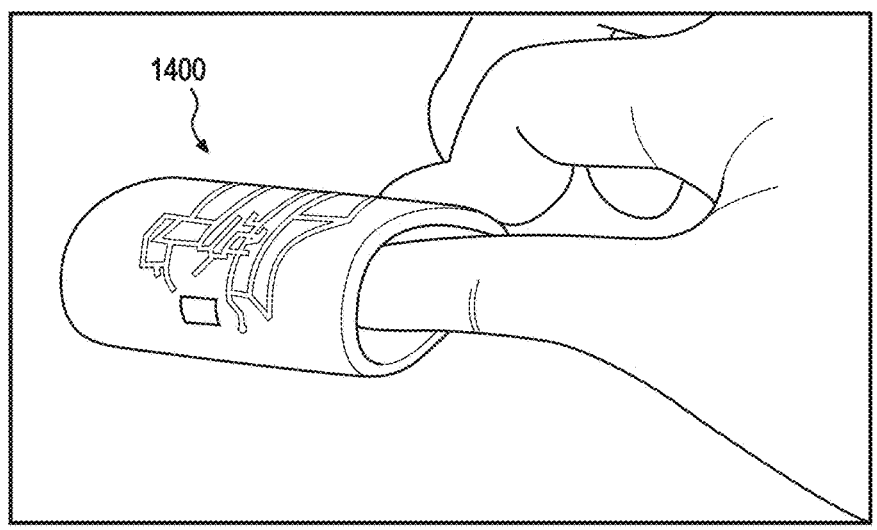
Figure 14C:
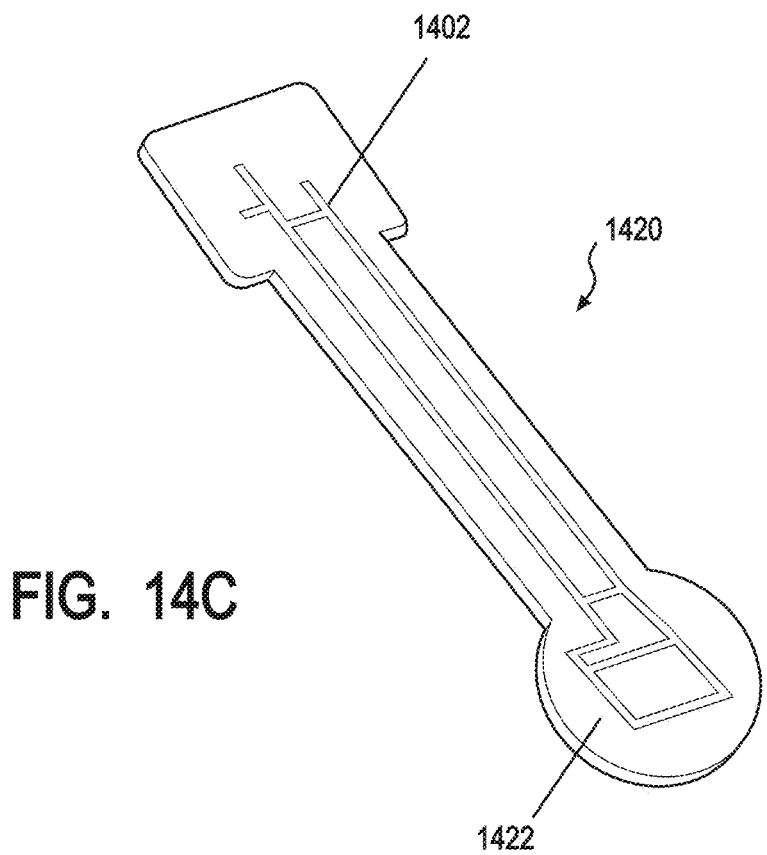

In reference of FIG. 14C, according to other non-limiting aspects, one or more portions 1422 of a flexible circuit 1420 can be configured as a pressure sensor, including any of those described in International Patent application Ser. No. PCT/US2021/071374, titled WEARABLE ARTICLE WITH FLEXIBLE INDUCTIVE PRESSURE SENSOR, filed Sep. 3, 2021, U.S. Provisional Application No. 63/270,589, titled FLEXIBLE THREE-DIMENSIONAL ELECTRONIC COMPONENT, filed Oct. 22, 2021, and U.S. Provisional Application No. 63/272,487, titled DEVICES, SYSTEMS, AND METHODS FOR MAKING AND USING A FLUID-FILLABLE CIRCUIT, filed Oct. 27, 2021, the disclosures of which are hereby incorporated by reference in its entirety. For example, according to the non-limiting aspect of FIG. 14C, the one or more portions 1422 of the flexible circuit 1420 can be configured as a coil that can be biased relative to a conductive plane integrated within a wearable article (e.g., mounting the conductive plane on foam or within a bladder filled with compressible fluid, etc.). As a distance between the conductive plane and the coil of the one or more portions 1422 of the flexible circuit 1420 changes, a difference in an electrical parameter (e.g., electromagnetic inductance) can be detected, for example, via a capacitor of a resistor, inductor, capacitor ("RLC") circuit, as disclosed in International Patent Application No. PCT/US2021/071374, titled WEARABLE ARTICLE WITH FLEXIBLE INDUCTIVE PRESSURE SENSOR, filed Sep. 3, 2021, U.S. Provisional Application No. 63/270,589. Accordingly, as the inductive coil of the one or more portions 1422 of the flexible circuit 1420 is depressed and/or extended, an electrical parameter (e.g., an electromagnetic inductance, etc.) generated by that portion 1422 of the flexible circuit 1420 will vary and corresponding signals can be transmitted via the circuits to the processor 114 (FIG. 1) for characterization of swelling at the location at which the portion 1422 is positioned. As such, the one or more portion 1422 of the flexible circuit 1420 configured as an inductive pressure sensor can be configured to monitor swelling in a specific portion of the joint and/or appendage, as previously disclosed.

Figure 14D:
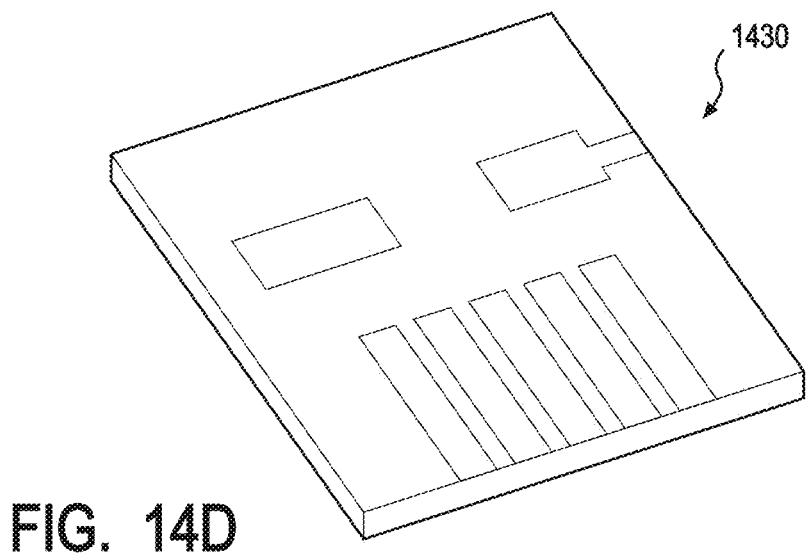

According to the non-limiting aspect of FIG. 14D, a flexible circuit 1430 can be configured for "spot" monitoring in a particular location of the wearable article. For example, the flexible circuit 1430 of FIG. 14D can be configured to function as a temperature sensor and/or a pressure sensor to monitor, for example, blood flow and/or swelling, as previously disclosed.

It shall be appreciated that, due to the flexible nature of the deformable conductors 1402 and medium 1403, the flexible circuits 1400, 1420, 1430 can be imbued with a tremendous amount of flexibility relative to conventional circuits. For example, according to the non-limiting aspect of FIG. 14A, a flexible circuit 1400 is at rest and unstrained. As such, when a current is introduced through the traces formed by the deformable conductors 1402, the flexible circuit will generate a plurality of electrical parameters at rest (e.g., an inductance, a resistance, a voltage drop, a capacitance, and/or an electromagnetic field, etc.). However, according to the non-limiting aspect of FIG. 14B, the flexible circuit 1400 can essentially be folded in half—and, according to other non-limiting aspects, coiled and/or twisted—without introducing discontinuities between traces and/or electronic components. Of course, as the flexible circuit 1400 undergoes such deformations, it will the plurality of electrical parameters generated by the flexible circuit 1400 under varying degrees of stress will differ from those the flexible circuit 1400 generates at rest. According to some non-limiting aspects, the flexible circuit 1400, including the fluid-phase conductors can experience deformations between 20% and 40% relative to an "at rest" condition, thus varying electrical parameters generated by the circuit 1400.

According to the non-limiting aspects where alternate conductors (e.g., silver ink, etc.) are used to form strain-sensing, flexible circuits, such circuits may experience no hysteresis and thus, may experience measurable changes in electrical characteristics upon returning to a relaxed state after undergoing a number of deformation cycles. This is known as "strain creep," or a degradation in performance as the number of deformation cycles increases. According to such aspects, the performance of a strain sensing flexible circuit 1300 that utilizes such alternate conductors can be enhanced via the calibration methods 2200 (FIG. 22) disclosed herein.

According to the non-limiting aspect of FIGS. 14A and 14B, the processor 1404 can receive signals from the various sensors and/or components dispositioned on the flexible circuit 1400 and thus, the processor 1404 can discern differences in generated electrical parameters and correlate them to various physical parameters associated with the deformation of the flexible circuit 1400, as disclosed in U.S. Provisional Patent Application No. 63/272,487, titled DEVICES, SYSTEMS, AND METHODS FOR MAKING AND USING A FLUID-FILLABLE CIRCUIT, and filed Oct. 27, 2021, the disclosure of which is hereby incorporated by reference in its entirety. As such, the flexible circuit 1400 of FIGS. 14A and 14B can be integrated into a wearable article to accurately monitor and characterize motions of a user's joint and/or appendage. According to some non-limiting aspects, the flexible circuit 1400 and/or wearable article can further include one or more IMUs. As such, differences in generated electrical parameters can be correlated to calibrate IMU data and used to supplement and/or calibrate IMU data, as previously described.

Figure 15:
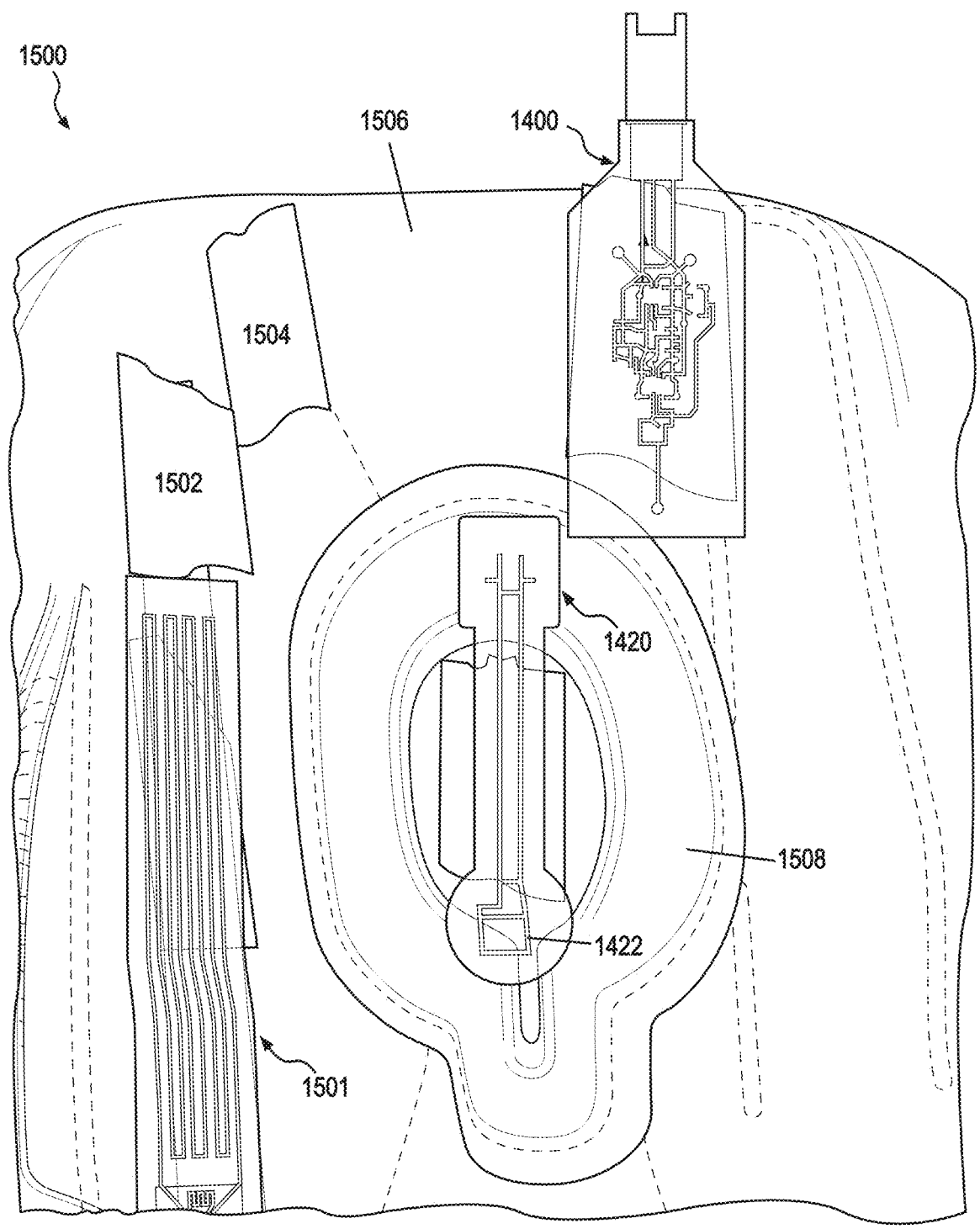
FIG. 15 illustrates another wearable article, in accordance with at least one non-limiting aspect of the present disclosure.

Referring now to FIG. 15, a wearable article 1500 configured to monitor and characterize motions of a user is depicted in accordance with at least one non-limiting aspect of the present disclosure. According to the non-limiting aspect of FIG. 15, the wearable article 1500 can be configured as a joint monitoring sleeve particularly designed to be worn about a user's knee. However, it shall be appreciated that, according to other non-limiting aspects, the joint monitoring sleeve 1500 can be alternately designed to be worn about any joint (e.g., knee, elbow, shoulder, wrist, ankle, hip, etc.) and/or appendage (e.g., arm, leg, finger, toe, neck, back, etc.) of a user. As depicted in FIG. 15, the joint monitoring sleeve 1500 of FIG. 15 can include the flexible circuit 1400 of FIG. 14A, configured to interface with various electrodes (e.g., electrodes 500, 600, 700, 800, 900 of FIGS. 5, 6, 7A, 7B, 8, 9A, and 9B) integrated within the wearable article and electrically couple those electrodes to other portions of circuits 1420, 1501, 1502, 1504 disposed throughout a flexible medium 1506 (e.g., elastic, spandex, cotton, and/or other natural and synthetic fabrics, etc.) from which the joint monitoring sleeve 1500 is formed. According to some non-limiting aspects, the flexible circuit 1400 can be similarly configured to the flexible circuit 1300 of FIG. 13 and, at a minimum, may include an IMU similar to the IMU island 1308 of the flexible circuit 1300 of FIG. 13.

Still referring to FIG. 15, the joint monitoring sleeve 1500 can further include a pressure-sensing flexible circuit 1420 because, as previously disclosed, the pressure-sensing flexible circuit 1420 can be particularly advantageous for monitoring swelling at a joint, or any other portion of the joint monitoring sleeve 1500 where swelling is of particular interest. According to some non-limiting aspects, the pressure-sensing flexible circuit 1420 can be mounted to a joint portion 1508 of the joint monitoring sleeve 1500, such that the flexible circuit 1420 is generally located at the patella. Instead of using pressure-sensing flexible circuit 1420 at the patella, according to some non-limiting aspects, strain gauge sensor 1501 can be positioned at the patella for strain-specific monitoring. Alternately, the flexible circuit 1420 can be configured to monitor single-axis strain across a joint. For example, the flexible circuit 1420 can generate electrical parameters (e.g., an inductance, a resistance, a voltage drop, a capacitance, and an electromagnetic field, etc.) from a point above the knee on the user's thigh, across the knee cap, to point below the knee on the user's shin. The electrical parameters generated by the flexible circuit 1420 can then be correlated to physical parameters (e.g., a strain, a stress, a pressure, a dimension, etc.) across that joint and used to characterize the user's motion while wearing the joint monitoring sleeve 1500.

In further reference to FIG. 15, one or more portions of the strain sensing flexible circuit 1501 can include an alternate trace configuration such that the traces are longer or otherwise different relative to other portions of the flexible circuit 1501. As such, electrical parameters generated at those portions can be exaggerated relative to electrical portions generated at other portions of the circuit 1501 and thus, particular areas of interest can be more responsive and monitored with increased accuracy.

As mentioned in reference to FIG. 14C, the flexible circuit 1420 can include one or more portions 1422 of a flexible circuit 1420 configured as a pressure sensor, such as an inductive pressure sensor. According, to the non-limiting aspect of FIG. 15, the one or more portions 1422 can be positioned just below the patella to monitor swelling at that portion of the knee. Additionally, the one or more portions 1422 of the flexible circuit 1420 can be positioned and/or biased relative to certain features of the joint monitoring sleeve 1500 to facilitate pressure measurements. For example, according to some non-limiting aspects, the joint portion 1508 of the joint monitoring sleeve 1500 may include a conductive layer and/or a woven layer that includes conductive fibers integrated distanced from the one or more portions 1422 of the flexible circuit 1420 configured as an inductive pressure sensor, by a biasing medium (e.g., foam) of a known spring constant. According to some non-limiting aspects, the coil portion 1422 can be adhered to a first layer (e.g., skin-facing layer) of the brace and the conductive layer can be integrated (e.g., sewn, adhered, woven, etc.) onto a second layer (e.g., external layer) of the brace, or vice versa. The biasing material of known spring constant (e.g., foam) can either be integral to the brace or dispersed between the first and second layer. As such, pressure can be determined based on the calculated distance between the coil and the conductive layer by correlating the measured electrical parameter (e.g., electromagnetic inductance) to a distance between the coil and the conductive layer.

Additionally and/or alternatively, according to some non-limiting aspects, the joint portion 1508 of the joint monitoring sleeve 1500 can be reinforced, as described below, such that the one or more portions 1422 of the flexible circuit 1420 configured as an inductive pressure sensor is not adversely affected by flexions of the knee and more exclusively responsive to swelling of the joint itself. As such, according to some preferable aspects, it might be advantageous to reinforce the one or more portions 1422 of the flexible circuit at the center of the joint portion 1508 of the joint monitoring sleeve 1500 such that the one or more portions 1422 of the flexible circuit 1420 is "locked out," or reinforced from flexions of the joint that could effect the distance between the coil and conductive layer and adversely (and inaccurately) affect the monitored pressure. Of course, the one or more portions 1422 can be positioned anywhere on the joint monitoring sleeve 1500 in accordance with anatomic need, user preference, and/or intended application.

In other words, the joint monitoring sleeve 1500 can have a different structural construction and or features (e.g., joint portion 1508) that can either mitigate or facilitate deformation of the flexible circuits at certain locations on the joint monitoring sleeve 1500. For example, textile properties can be attenuated (e.g., thicker, thinner, less flexible, more pliable, more cushioned, etc.) at certain locations of the joint monitoring sleeve 1500 relative to the position of certain flexible circuits 1400, 1420, 1501, 1502, 1504, which can affect deformation and thus, attenuate electrical parameters generated by those circuits 1400, 1420, 1501, 1502, 1504. Accordingly, such features can de-activate strain sensing capabilities in some regions where a strain sensor is present (e.g., could "lock out" regions of a strain sensor at either side of a joint, leaving only the portion extending over the joint free to stretch).

According to some non-limiting aspects, similar features can be utilized to promote comfort in portions of the joint monitoring sleeve 1500 where flexible circuit structures are mounted. For example, flexible circuits can be mounted to more rigid or flexible portions 1506, 1508 of the joint monitoring sleeve 1500, such that the structural features of the flexible circuits will not be as noticeable to the user while the joint monitoring sleeve 1500 is in use, thereby reducing user discomfort. For example, such features can be introduced via the methods described in U.S. Pat. No. 8,898,932, titled ARTICLE OF FOOTWEAR INCORPORATING A KNITTED COMPONENT, and filed May 9, 2019, the disclosure of which is hereby incorporated by reference in its entirety. Specifically, U.S. Pat. No. 8,898,932 provides an exemplary of knitting an article and re-enforcing portions of the textile. However, according to the present disclosure, in conjunction with promoting user comfort, one could use similar techniques to reinforce and/or enhance the deformation of certain portions 1506, 1508 of the joint monitoring sleeve 1500 to promote desired electrical responses from the flexible circuits 1400, 1420, 1501, 1502, 1504.

According to the non-limiting aspect of FIG. 15, the joint monitoring sleeve 1500 can include another flexible circuit and/or sensor 1504 configured for "spot" monitoring in a particular location of the wearable article. For example, the flexible circuit 1504 can be include a temperature sensor and/or can be configured to function as a pressure sensor to monitor, for example, blood flow and/or swelling at a particular portion of the joint monitoring sleeve 1500, as previously discussed. According to some non-limiting aspects, the other flexible circuit and/or sensor 1504 can include a temperature sensor. Of course, according to other non-limiting aspects, the flexible circuit and/or sensor 1504 can include alternative pressure sensors (e.g., strain gauges, thin film pressure sensors, variable capacitance pressure sensors, etc.), implemented to achieve a similar effect.

In further reference to FIG. 15, the joint monitoring sleeve 1500 can further include a third flexible circuit 1501 configured as a strain sensor and electrically coupled to an on-board indicator 1502 that includes one or more light emitting diodes ("LEDs") configured to illuminate in response to signals that correspond to electrical parameters generated by the third flexible circuit 1501. As will be described in further detail herein, specifically in reference to FIGS. 21A-C or the one or more LEDs and/or plurality of buttons 1910 of FIG. 19, the on-board indicator 1502 can be configured to provide real-time feedback regarding the user's motion while using the joint monitoring sleeve 1500. However, the one or more LEDs of indicator 1502 can allow a user to easily monitor flexion range in real time. According to some non-limiting aspects, the on-board indicator 1502 can also be used to guide the patient through range of motion exercises during rehabilitation. Additionally and/or alternatively, the indicator 1502 can include a more sophisticated display, a haptic sensor, and/or a transducer configured to provide more sophisticated visual indicia, haptic feedback, and/or audible alerts associated with the user's motions while wearing the joint monitoring sleeve 1500, according to some non-limiting aspects.

Although it is not visibly apparent in FIG. 15, it shall be appreciated that the flexible circuits 1400, 1420, 1501, 1502, 1504 of the joint monitoring sleeve 1500 can be electrically coupled to a bus architecture, similar to the serial communication bus 1310 of FIG. 13, integrated within the joint monitoring sleeve 1500. According to some non-limiting aspects, the integrated architecture of the flexible circuit 1300 of FIG. 13 can be implemented to incorporate the components and functionality of the joint monitoring sleeve 1500 of FIG. 15, thereby enabling the aforementioned efficiency and economic advantages. According to still other non-limiting aspects, the joint monitoring sleeve 1500 can include one or more vias configured to vertically stack circuitry on multiple planes, which can reduce required materials and thus, increase the stretch of the fluid-phase conductors, circuits, and throughput.

Additionally and/or alternatively, any and/or all of the flexible circuits 1400, 1420, 1502, 1504 of the joint monitoring sleeve 1500 of FIG. 15 can be electrically coupled to an on-board processor (e.g., processor 114 of FIG. 1, etc.) configured to receive and process signals generated across the joint monitoring sleeve 1500 and characterize the motions of the user based on those signals and subsequent aggregations and correlations, as disclosed herein. According to other non-limiting aspects, the flexible circuits 1400, 1420, 1502, 1504 of the joint monitoring sleeve 1500 can be electrically coupled to a remote processor. According to still other non-limiting aspects, the joint monitoring sleeve 1500 can further include a wireless transceiver configured to wirelessly transmit signals to and from a remote processor.

In still other non-limiting aspects, the joint monitoring sleeve 1500 can wirelessly communicate with a mobile computing device (e.g., a laptop, a smart phone, a smart watch, smart glasses, etc.) including a transceiver and one such remote processor configured to provide real-time feedback to the user (e.g., visual indicia, audible alerts, haptic feedback, etc.). According to such aspects, the mobile computing device can further include a memory configured to store an application that, when executed by the remote processor, causes the remote processor to generate a simulation of the users motions based on signals received from the joint monitoring sleeve 1500 and display the simulation via display of the mobile computing device. According to still other non-limiting aspects, the application can be configured to guide the user through predefined exercises and provide real-time feedback associated with those exercises, either via alerts (e.g., audible, visual, haptic, etc.) provided via components (e.g., speakers, displays, haptic activators, etc.) on board the sleeve 1500 or remotely on the mobile computing device. According to other non-limiting aspects, the application, when executed by the remote processor, can further cause the remote processor of the mobile computing device to transmit, via the transceiver of the mobile computing device, real-time feedback via the onboard indicator (e.g., indicator 1608 of FIG. 16) of the joint monitoring sleeve 1500. According to still other non-limiting aspects, the joint monitoring sleeve 1500 and/or the mobile computing device can be communicably coupled to a remote server configured to store medical data associated with the user of the joint monitoring sleeve 1500. In such aspects, the joint monitoring sleeve 1500 and/or the mobile computing device can be configured for secure communications (e.g., symmetric encryption, asymmetric encryption, hashing, etc.) to ensure compliance with regional healthcare regulations (e.g., the Health Insurance Portability and Accountability Act of 1996 (HIPAA)).

Figure 16:
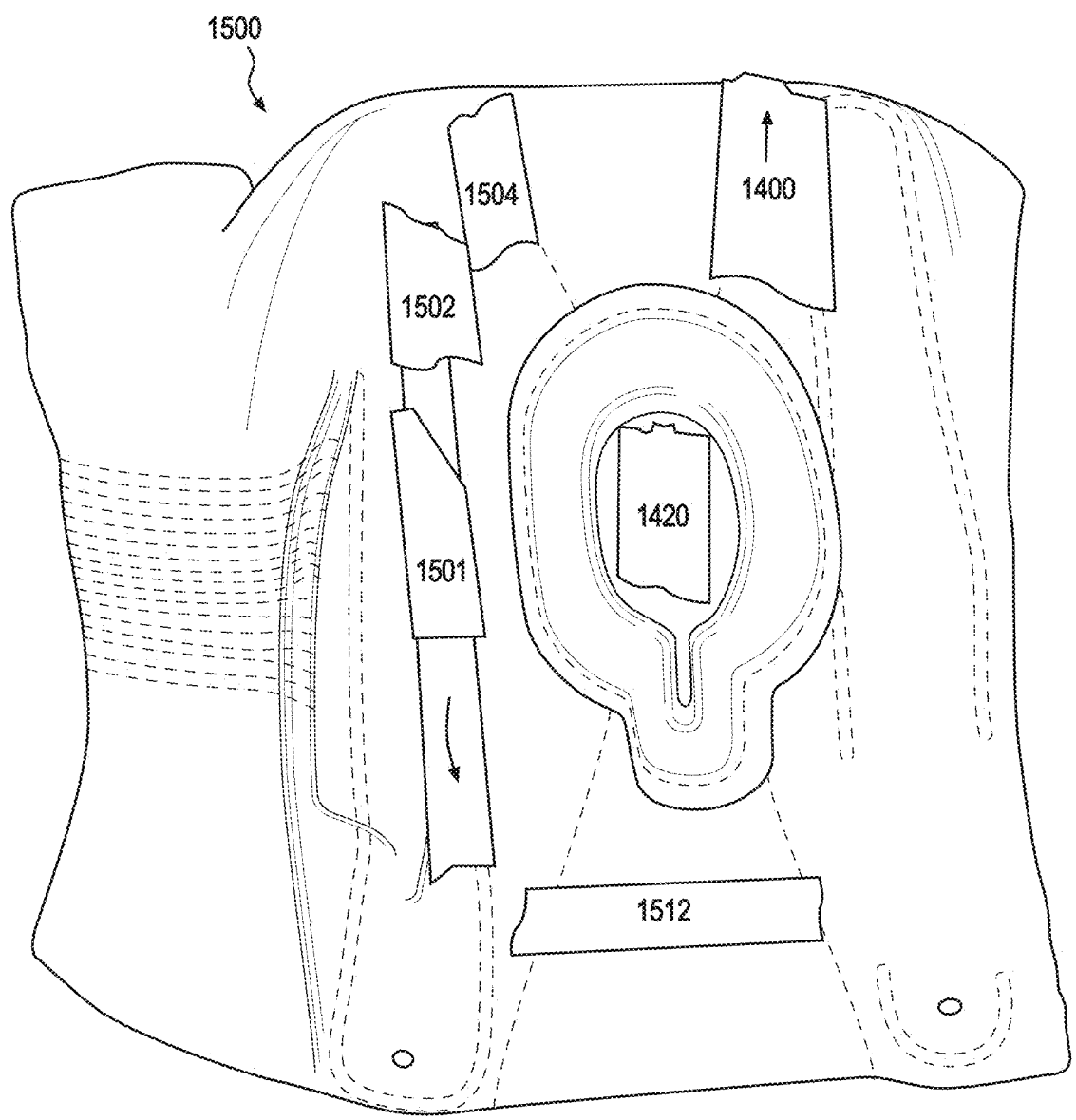
FIG. 16 illustrates the wearable article of FIG. 15, in accordance with at least one non-limiting aspect of the present disclosure.

Referring now to FIG. 16, the wearable article 1500 of FIG. 15 is depicted in accordance with at least one non-limiting aspect of the present disclosure. According to the non-limiting aspect of FIG. 16, the flexible circuits 1400, 1420, 1501, 1502, 1504 of the joint monitoring sleeve 1500 have been integrated within the joint monitoring sleeve 1500. However, as depicted in FIG. 16, the joint monitoring sleeve 1500 can further include a separate strain monitoring circuit 1612 positioned below the patella monitoring circuit 1604. The separate strain monitoring circuit 1612 can be included to the joint monitoring sleeve 1500 to provide additional monitoring, such as transverse strain in the joint monitoring sleeve 1500. This can also be helpful in monitoring the fit of the joint monitoring sleeve 1500 and/or monitor swelling.

Figure 17:
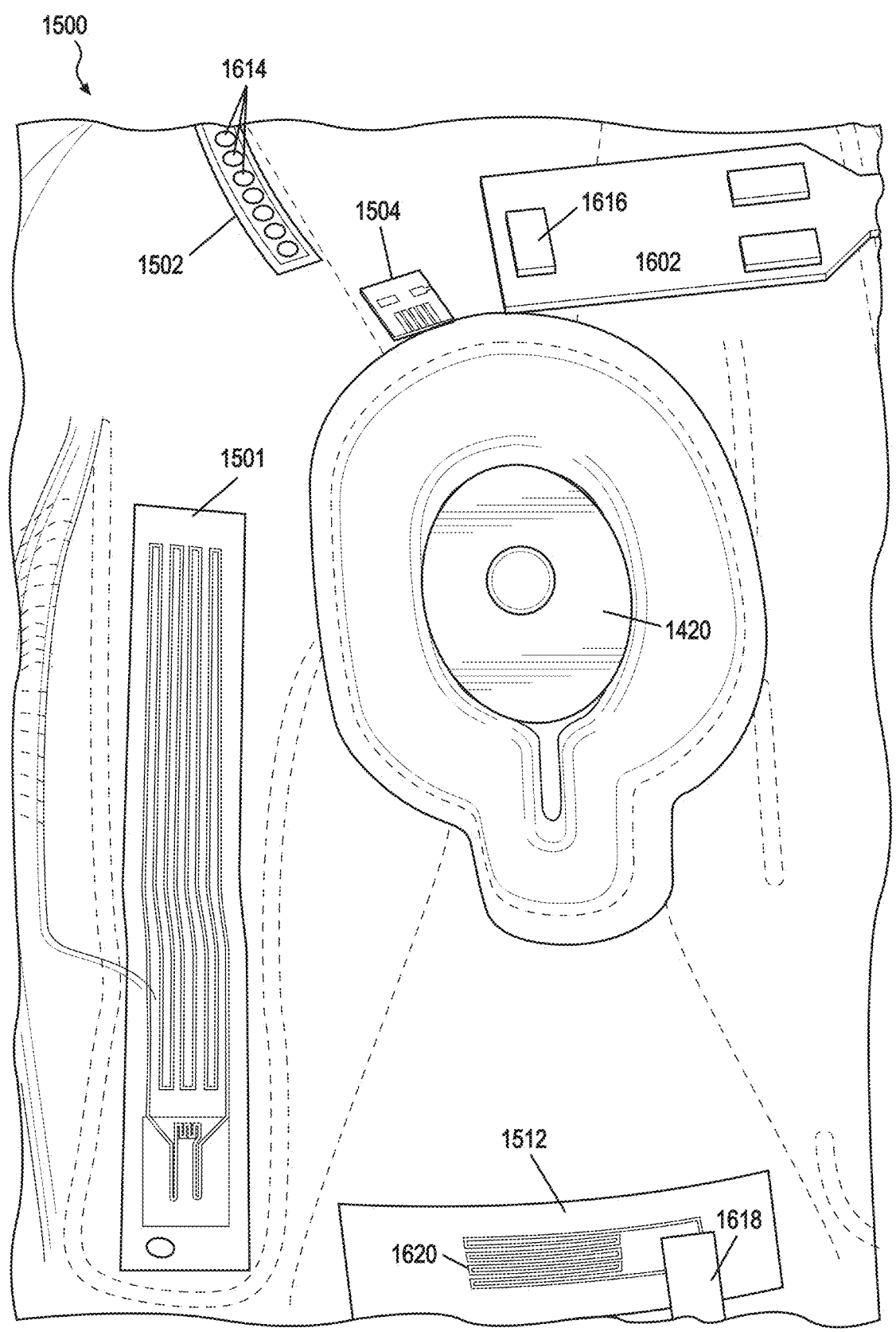
FIG. 17 illustrates the wearable article of FIGS. 15 and 16, in accordance with at least one non-limiting aspect of the present disclosure.

Referring now to FIG. 17, the joint monitoring sleeve 1500 of FIGS. 15 and 16 is depicted in accordance with at least one non-limiting aspect of the present disclosure. According to the non-limiting aspect of FIG. 17, the joint monitoring sleeve 1500 can include another circuit 1602 configured to be positioned above the knee joint on the thigh of the user in conjunction with the flexible circuit 1512 configured to be positioned below the knee joint on the shin of the user. At a minimum, a first circuit 1602 configured to be positioned above the knee joint on the thigh of the user and a second circuit 1612 configured to be positioned below the knee joint on the shin of the user may include an IMU similar to the IMU island 1308 of the flexible circuit 1300 of FIG. 13. Accordingly, the first circuit 1602 and the second circuit 1512 can include, at least, a first IMU 1616 and a second IMU 1618 configured to generate IMU data, respectively. As such, the pressure monitoring circuit 1420 can generate electrical parameters (e.g., strain data, for example) that can be correlated to IMU data generated by the IMUs 1616, 1618 and thus, can calibrate the IMUs 1616, 1618, thereby mitigating drift and enhancing the overall accuracy of the joint monitoring sleeve 1500. Of course, depending on the particular joint and/or appendage being monitored, the quantity of components (e.g., electrodes, sensors, flexible circuits, IMUs, etc.) can be varied. A two IMU configuration makes sense for a non-limiting aspect where a knee is being monitored because a knee has only two planes of motion. However, the specific configuration can be varied depending on the joint and/or appendage being monitored. For example, a shoulder includes five planes of motion and may require more IMUs with accompanying flexible circuits disposed between each to accurately monitor the full range of motion.

Figure 22:
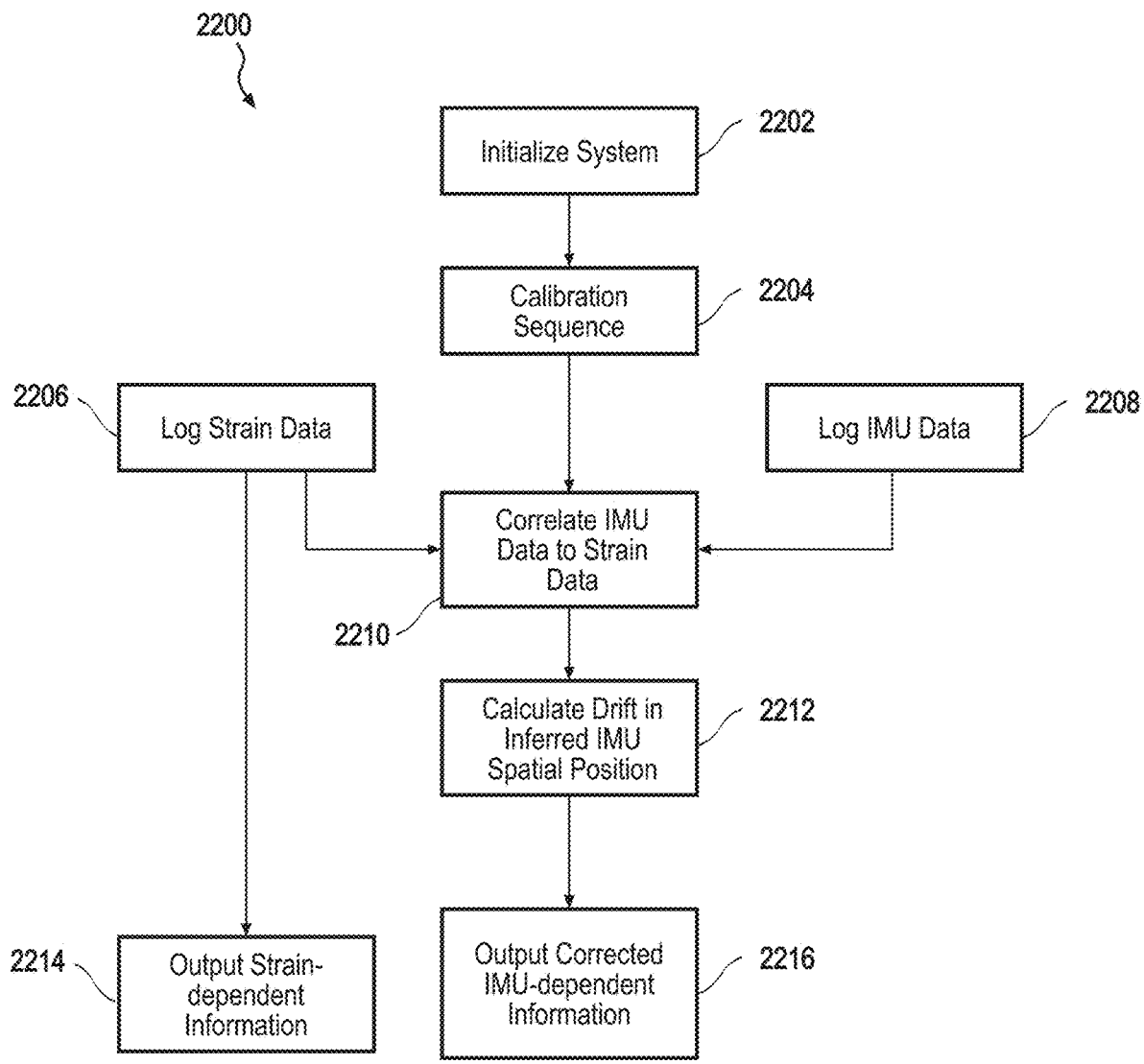
FIG. 22 illustrates a method of calibrating strain gauge data and IMU data, in accordance with at least one non-limiting aspect of the present disclosure.

According to some non-limiting aspects, calibration of data generated by any combination of electrodes, sensors, flexible circuits, and/or IMUs can be performed in accordance with the method 2200 of FIG. 22, as discussed in further detail herein. Additionally and/or alternatively, image capture data can be used and correlated to data generated by any combination of electrodes, sensors, flexible circuits, and/or IMUs in accordance with the method 2400 of FIG. 23, as discussed in further detail herein. It shall be appreciated that the method 2400 of FIG. 23 can be particularly useful in using data from the electrodes, sensors, flexible circuits, and/or IMUs disclosed herein to generate a simulation of the user's motions while wearing the joint monitoring sleeve 1600 of FIG. 16 in a virtual environment.

Figure 18:
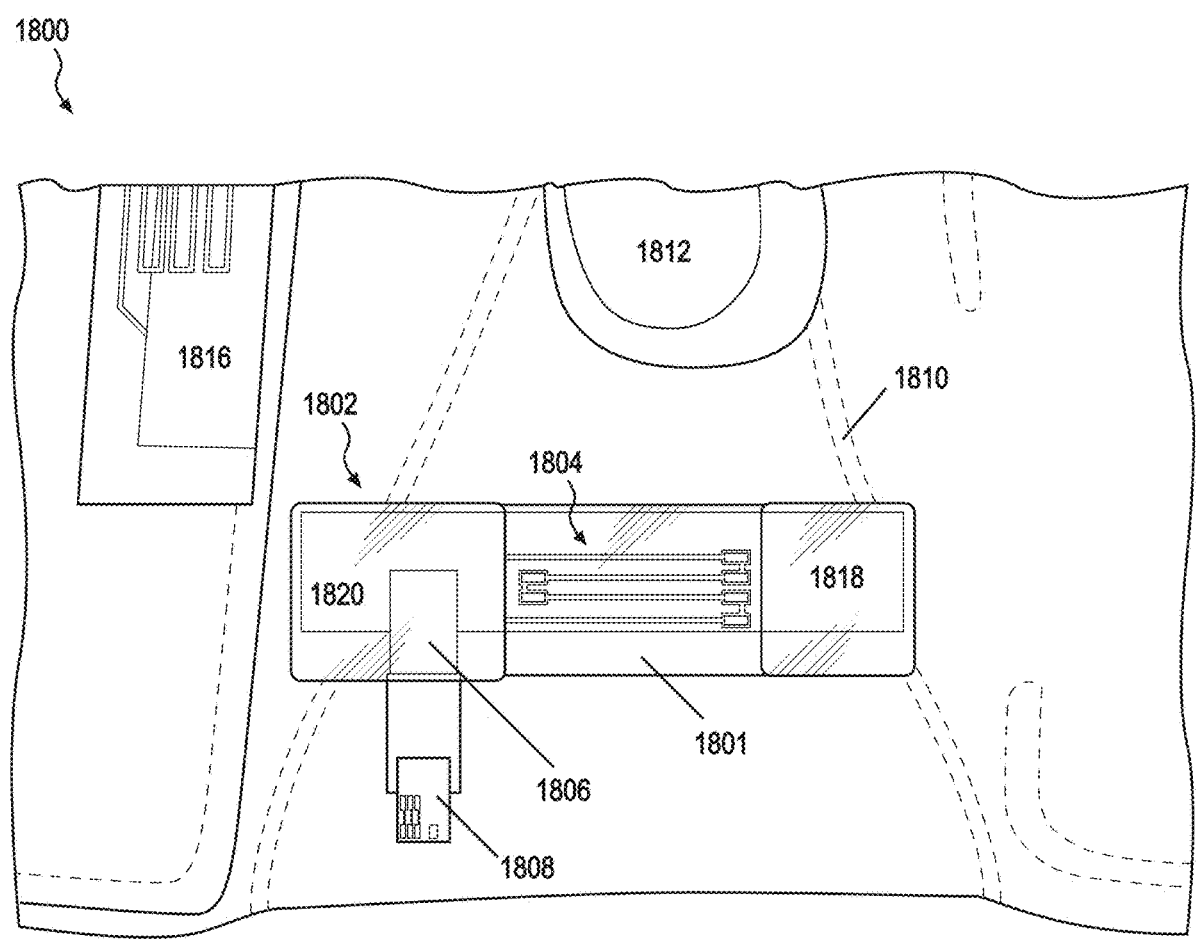
FIG. 18 illustrates another wearable article, in accordance with at least one non-limiting aspect of the present disclosure.

Referring now to FIG. 18, another wearable article 1800 configured to monitor and characterize motions of a user is depicted in accordance with at least one non-limiting aspect of the present disclosure. Similar to the wearable articles 1500, 1600 of FIGS. 15-17, the wearable article 1800 of FIG. 18 can be configured as a joint monitoring sleeve particularly designed to be worn about a user's knee. However, it shall be appreciated that, according to other non-limiting aspects, the joint monitoring sleeve 1800 can be alternately designed to be worn about any joint (e.g., knee, elbow, shoulder, wrist, ankle, hip, etc.) and/or appendage (e.g., arm, leg, finger, toe, neck, back, etc.) of a user.

According to the non-limiting aspect of FIG. 18, the wearable article 1800 can include another flexible circuit 1802 positioned below a patella portion 1812 of the wearable article 1800. According to the non-limiting aspect of FIG. 18, the flexible circuit 1802 can include a more integrated architecture, similar to the flexible circuit 1300 of FIG. 13. For example, the flexible circuit 1802 of FIG. 18 can include plurality of traces 1804 formed from deformable conductors and configured to function as a strain sensor, a pressure sensor 1820, a temperature sensor 1818, and an IMU 1806 all mounted to the same flexible medium 1801 or substrate. According to the non-limiting aspect of FIG. 18, the integrated, flexible circuit 1802 can be electrically coupled to a processor 1808, although according to other non-limiting aspects, the processor 1808 can be integrated onto the flexible medium 1801 as well, similar to the processor 1306 of FIG. 13.

In further reference to the non-limiting aspect of FIG. 18, the joint monitoring sleeve 1800 can further include a bus architecture 1810 similar to the serial communication bus 1310 (e.g., an I2C protocol, etc.) of FIG. 13 can be formed from deformable conductors and integrated within the joint monitoring sleeve 1800 and can electrically couple the integrated, flexible circuit 1802 to other sensors, circuits, and/or electrodes positioned elsewhere on the joint monitoring sleeve 1800, such as strain sensing circuit 1816.

Figure 19:
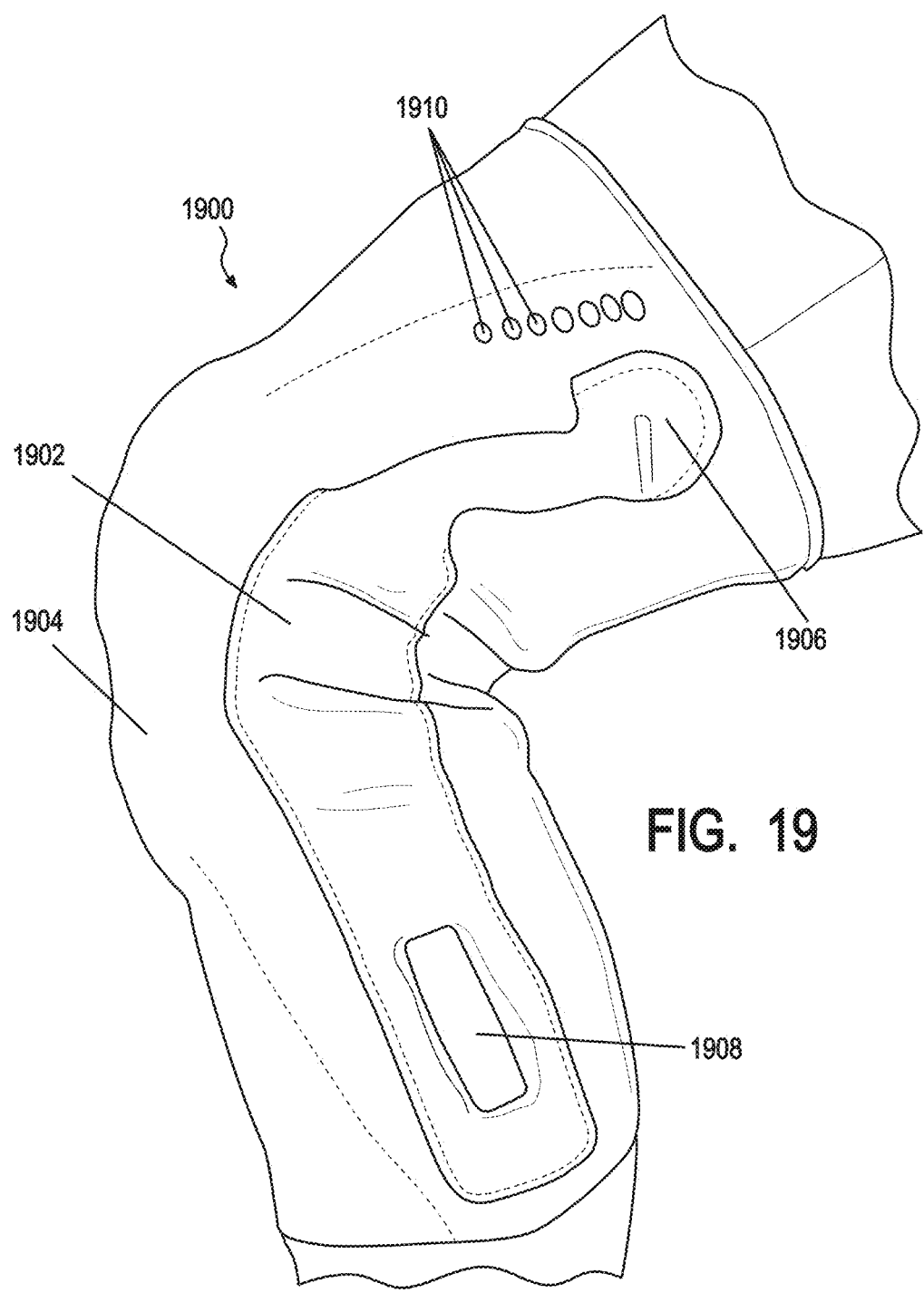
FIG. 19 illustrates another wearable article, in accordance with at least one non-limiting aspect of the present disclosure.

Referring now to FIG. 19, another wearable article 1900 configured to monitor and characterize motions of a user is depicted in accordance with at least one non-limiting aspect of the present disclosure. Similar to the wearable articles 1500, 1600, 1800 of FIGS. 15-18 the wearable article 1800 of FIG. 18 can be configured as a joint monitoring sleeve particularly designed to be worn about a user's knee. However, it shall be appreciated that, according to other non-limiting aspects, the joint monitoring sleeve 1900 can be alternately designed to be worn about any joint (e.g., knee, elbow, shoulder, wrist, ankle, hip, etc.) and/or appendage (e.g., arm, leg, finger, toe, neck, back, etc.) of a user.

According to the non-limiting aspect of FIG. 19, the joint monitoring sleeve 1900 can include a first portion 1902 and a second portion 1904, which can have different material properties to either promote or inhibit flexibility of integrated circuits 1906, 1908 and/or enhance the user's comfort, as previously discussed. For example, according to some non-limiting aspects, a portion 1902 housing the sensors and/or circuits 1906, 1908 may be more flexible than a surrounding portion 1904, which may house a variety of ancillary, non-sensing circuitry. As previously discussed, the sensors and/or circuits 1906, 1908 can be particularly configured to generate electrical parameters that can be correlated to the user's motions and thus, it might be more desirable to promote flexibility of those components. Therefore, the surrounding portion 1904 may be reinforced to inhibit flexions of the ancillary circuitry within.

Still referring to FIG. 19, the joint monitoring sleeve 1900 can include a first circuit 1906 configured to be positioned above the knee joint on the thigh of the user and a second circuit 1908 configured to be positioned below the knee joint on the shin or calf of the user. Both the first circuit 1906 and the second circuit 1908 can include an IMU similar to the IMU island 1308 of the flexible circuit 1300 of FIG. 13. A patella monitoring circuit (not shown) can be integrated within the first portion 1902 of the joint monitoring sleeve 1900 and can generate electrical parameters (e.g., strain data, for example) that can be correlated to IMU data generated by the IMUs of the first circuit 1906 and the second circuit 1908. Accordingly, the patella monitoring circuit (not shown) can calibrate the IMUs 1616, 1618, thereby mitigating drift and enhancing the overall accuracy of the joint monitoring sleeve 1600. According to some non-limiting aspects, calibration of data generated by any combination of electrodes, sensors, flexible circuits, and/or IMUs can be performed in accordance with the method 2200 of FIG. 22, as discussed in further detail herein.

Additionally, the joint monitoring sleeve can include an indicator including one or more LEDs and/or a plurality of buttons 1910, which can be coupled to an internal, flexible, strain-sensing circuit integrated within the joint monitoring sleeve 1900. As such, the LEDs 1910 can be illuminated in response to electrical parameters generated by the electrically coupled internal, flexible, strain-sensing circuit. As will be discussed in further detail in reference to FIGS. 21A-C, the LEDs (and other indicia generated by the indicator, via other means) can provide the user with real-time feedback regarding their motions while wearing the joint monitoring sleeve 1900. According to some non-limiting aspects, the deformable conductor can be used to make capacitive user input buttons 1910 which are integrated to the material of the joint monitoring sleeve 1900 such that touching the exterior surface of the brace in designated areas could cycle the functions of the brace to display different sensor outputs on the LCD array 1910. Further, the capacitive input elements can be used to zero the feedback shown on the display or logged into memory for later retrieval. The buttons can be used by the end user to log a position in which the user feels discomfort, or an activity that results in pain, such as by adding a flag or tag to data being logged by onboard memory integrated into the control circuitry of the joint monitoring sleeve 1900.

In further reference to FIG. 19, the flexible and/or stretchable nature of the joint monitoring sleeve 1900 and specifically, the flexibility provided by the deformable conductor that forms the traces can enable the generation of electrical parameters that can be correlated to physical parameters associated with physical movements of the user. For example, as the user dons the joint monitoring sleeve 1900 and moves their leg, the resulting physical disturbance to the traces, sensors, flexible circuits, electrodes, and/or other components mounted to and/or integrated within portions 1902, 1904 of the joint monitoring sleeve 1900, can subsequently vary the electrical parameters (e.g., an inductance, a resistance, a voltage drop, a capacitance, and an electromagnetic field, etc.) generated by the traces and/or other electrical components. Generated electrical parameters can be correlated to each other and/or baseline data to monitor and/or characterize the motion of the user's leg while wearing the joint monitoring sleeve 1900. The electrical parameters (e.g., an inductance, a resistance, a voltage drop, a capacitance, and an electromagnetic field, etc.) generated by the joint monitoring sleeve 1900 can be correlated to physical parameters (e.g., a strain, a stress, a pressure, a dimension, etc.) associated with the joint monitoring sleeve 1900 and thus, can be used to monitor and/or model the motion of the user's leg. Specifically, differences in correlated physical parameters of can be used to model the user's leg in a virtual environment.

Referring now to FIGS. 20A-D, a wearable article 2000 configured to monitor and motions of a user, including a corresponding characterization 2004 of the monitored motions, is depicted in accordance with at least one non-limiting aspect of the present disclosure. For example, a wearable article 2000 configured as a joint monitoring sleeve is depicted in an actual environment 2002. According to the non-limiting aspect of FIGS. 20A-D, the joint monitoring sleeve 2000 can include a flexible circuit 2001 configured as a strain sensor dispositioned across a user's knee. However, according to other non-limiting aspects, the joint monitoring sleeve 2000 can further include any number of electrodes, IMUs, pressure sensors, and/or temperature sensors, as described herein.

Additionally, FIGS. 20A-D further depict a generated model 2006 of the joint monitoring sleeve 2000 in a virtual environment 2004. As previously described, the flexible circuit 2001 can generate electrical parameters and it is deformed while the user is moving their leg, and the electrical parameters can be used to generate a highly accurate model 2006 of the joint monitoring sleeve 2000 based on correlations, as described in the methods 2200, 2400 of FIGS. 22 and 24. The model 2006 can be presented on a display communicably coupled to a processor (e.g., processor 114 of FIG. 1, processor 1306 of FIG. 13, processor 1808 of FIG. 18, a remote processor, etc.), along with various widgets 2008, 2010, 2012. For example, a first widget 2012 can present real-time motion data associated with the current condition of the user's joint and/or appendage. For example, according to the non-limiting aspect of FIG. 20A, the user's leg is bent within the joint monitoring sleeve 2000. Accordingly, the first widget 2012 displays a current hip angle of 29.9 degrees and a current knee angle of 67.3 degrees. The second widget 2008 and the third widget 2010 are historical motion data charts and thus, exclusively reflect the current hip angle and knee angle since the monitoring and characterization has just begun. Additionally, the generated model 2006 of the user's leg reflects the real-time position of the user's leg with a hip angle of 29.9 degrees and a knee angle of 67.3 degrees, within the joint monitoring sleeve 2000.

Figure 20A:
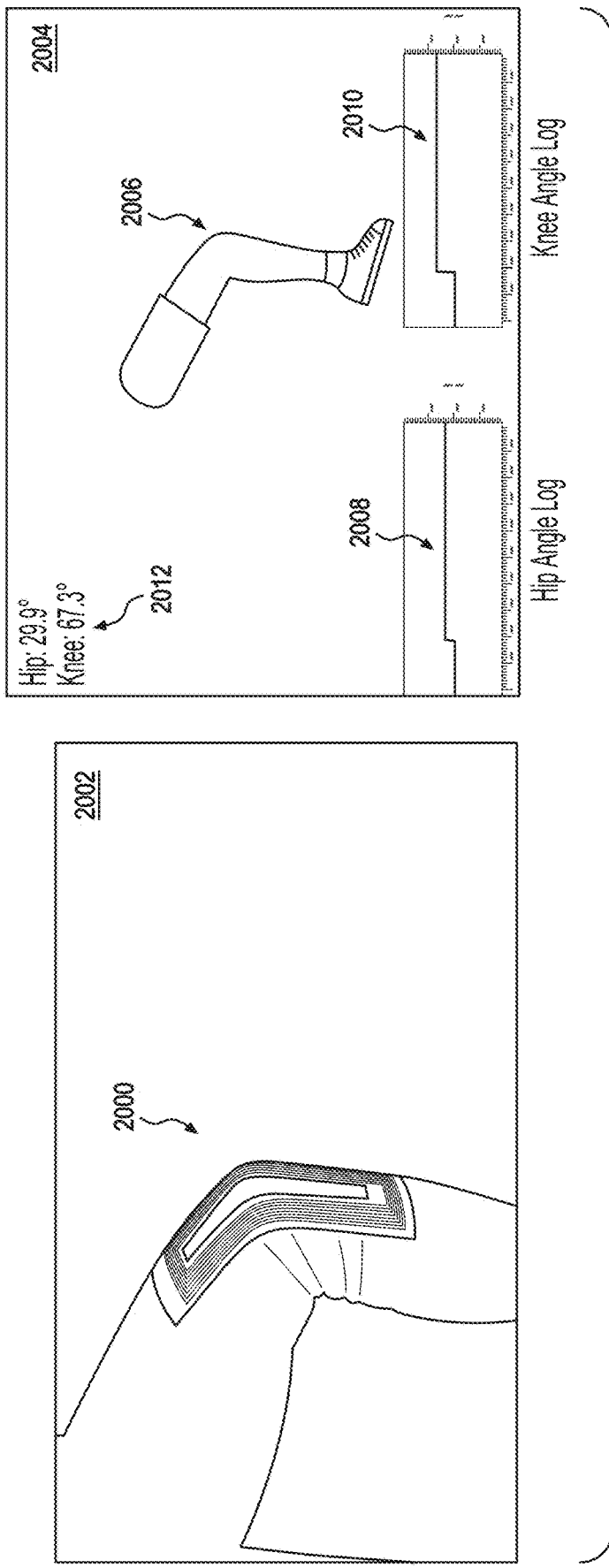
FIGS. 20A-D illustrate a wearable article configured to monitor and motions of a user, including a corresponding characterization of the monitored motions, in accordance with at least one non-limiting aspect of the present disclosure.
Figure 20B:
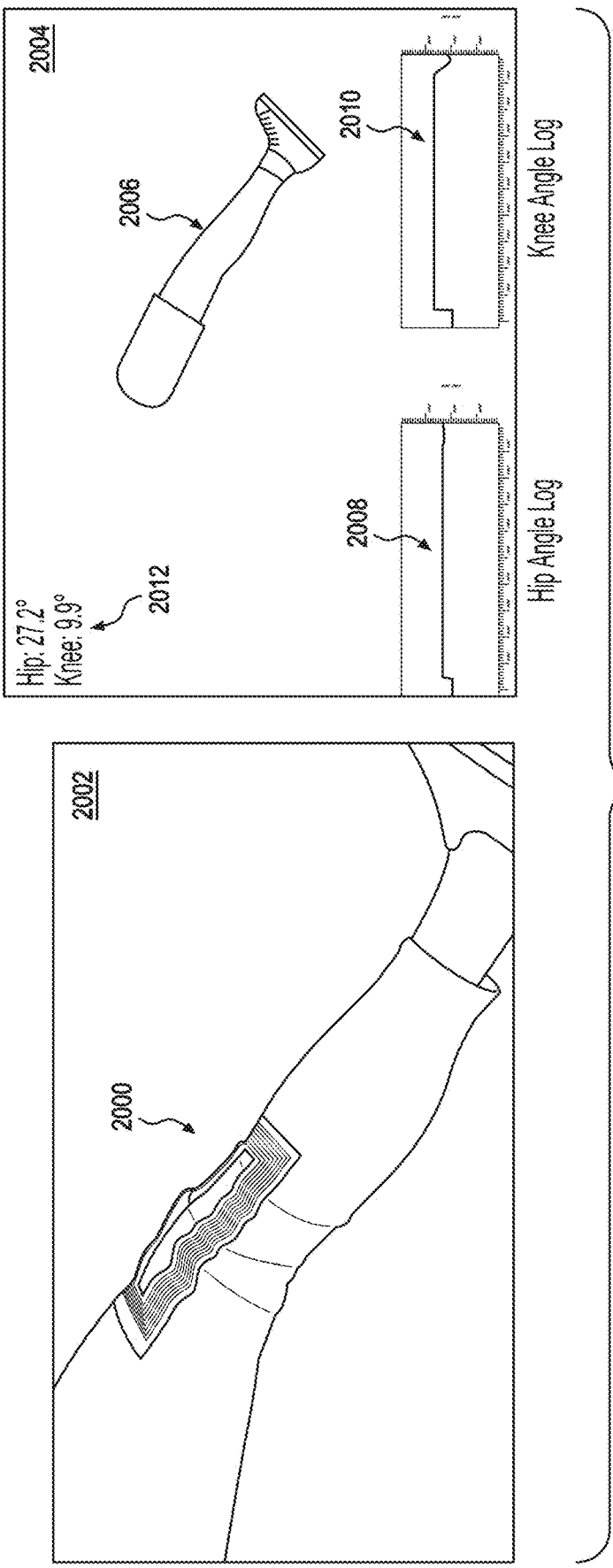
Figure 20C:
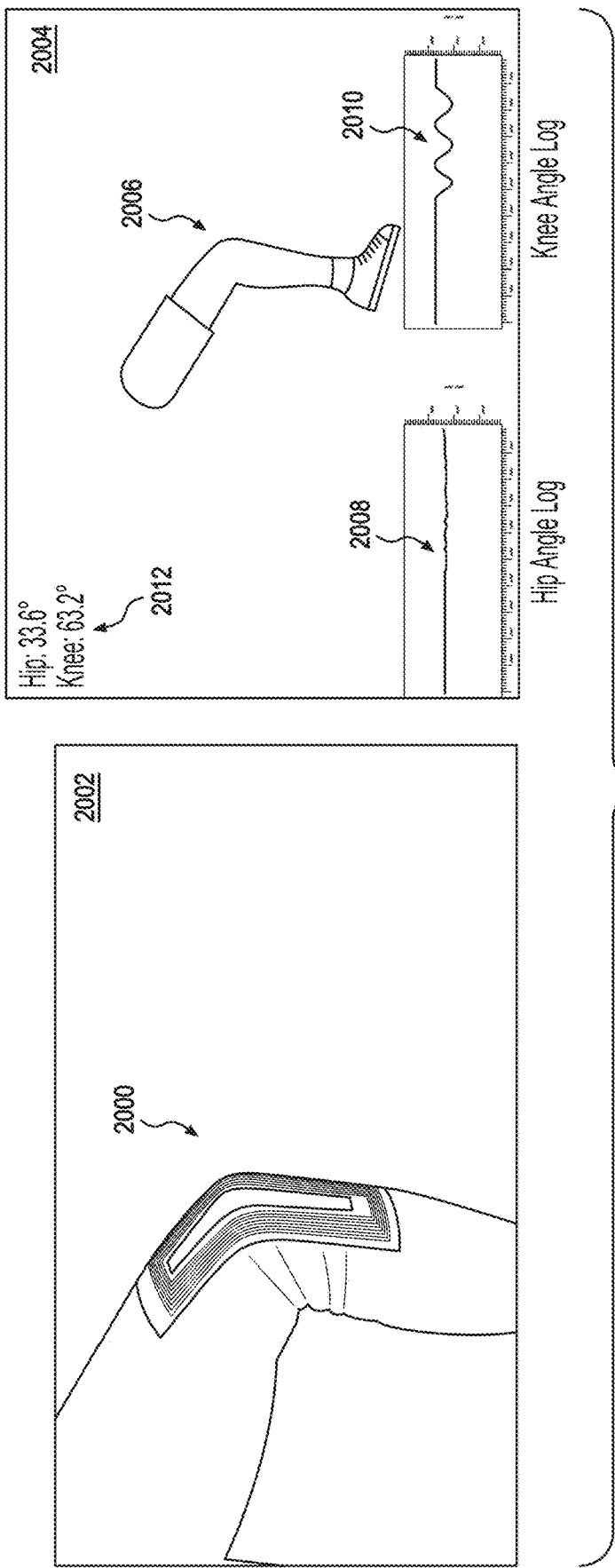

Referring now to FIG. 20B, the user has extended their leg within the joint monitoring sleeve 2000 in the actual environment. Accordingly, the first widget 2012 indicates that the user's current hip angle is 27.2 degrees and current knee angle is 9.9 degrees, and the model 2006 has been updated to accurately reflect the real-time position of the user's leg within the joint monitoring sleeve 2000 in the virtual environment 2004. Moreover, the second widget 2008 and third widget 2010 have been updated to reflect the change in the historical motion data monitored and characterized by the joint monitoring sleeve 2000. In FIG. 20C, the user has once again bent their knee to a hip angle of 33.6 degrees and a knee angle of 63.2 degrees. In the virtual environment, the model 2006 and first widget 2012 have been updated accordingly to reflect the real-time position of the user's leg within the joint monitoring sleeve 2000. Additionally, the second widget 2008 and third widget 2010 have been updated to log the real-time position data on the historical chart.

Figure 20D:
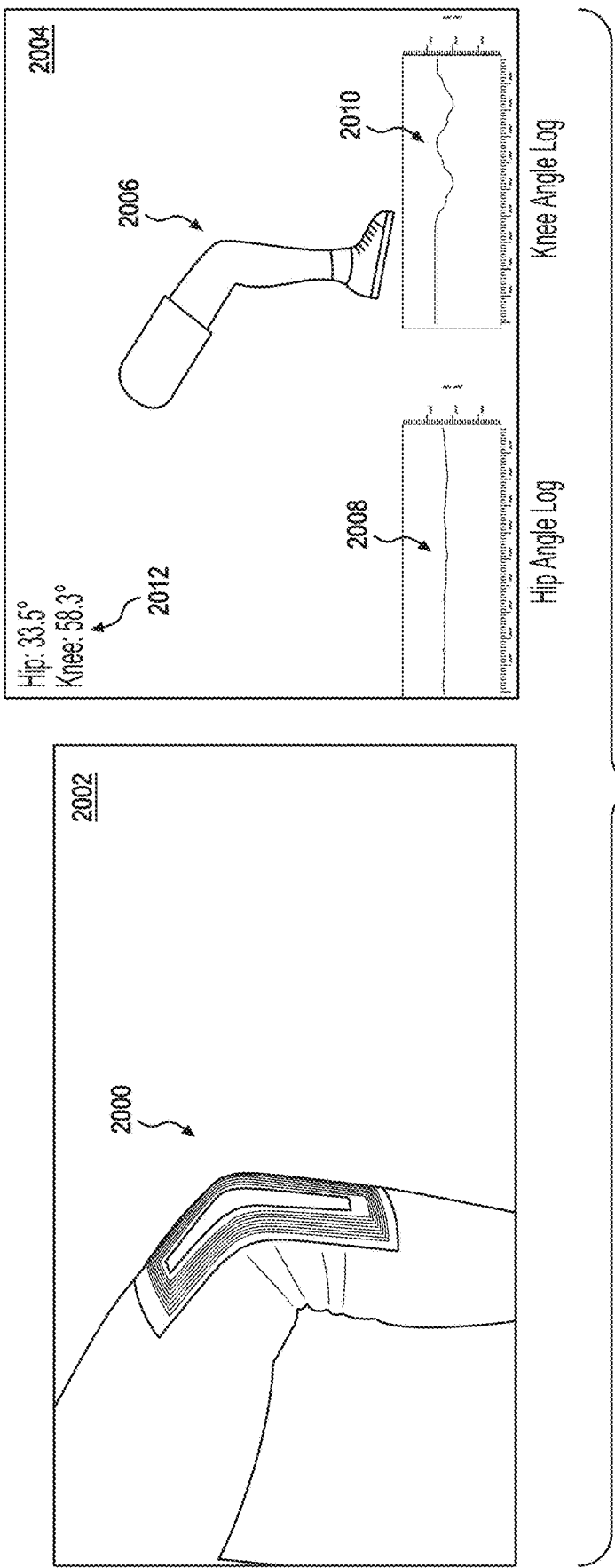

According to FIG. 20D, the user has continued the hip flexions of FIGS. 20A-C a few times, as is illustrated via the second widget 2008 and third widget 2010. Aside from the generated model 2006 characterizing the real-time position of the user's leg within the joint monitoring sleeve 2000 in the actual environment, the second widget 2008 and third widget 2010 have been updated to reflect a sinusoidal-type curve of significantly high resolution, which illustrates the accuracy with which the user's motion within the joint monitoring sleeve 2000 can be monitored. As such, it shall be appreciated how the integration of various combinations of flexible circuits, sensors, and/or electronic components into a wearable article, as disclosed herein, can be implemented to generate highly accurate models of a user's motions. This can produce numerous benefits. For example, according to some non-limiting aspects, a doctor can monitor a patient's rehabilitation from a remote location, increasing access to high-quality health care. According to other non-limiting aspects, the model 2006 of FIGS. 20A-D can be used for virtual reality games and/or other applications, including improved metaverse applications. According to some non-limiting aspects, the model 2006 and/or widgets 2008, 2010, 2012 can be displayed on a mobile computing device.

Figure 21A:
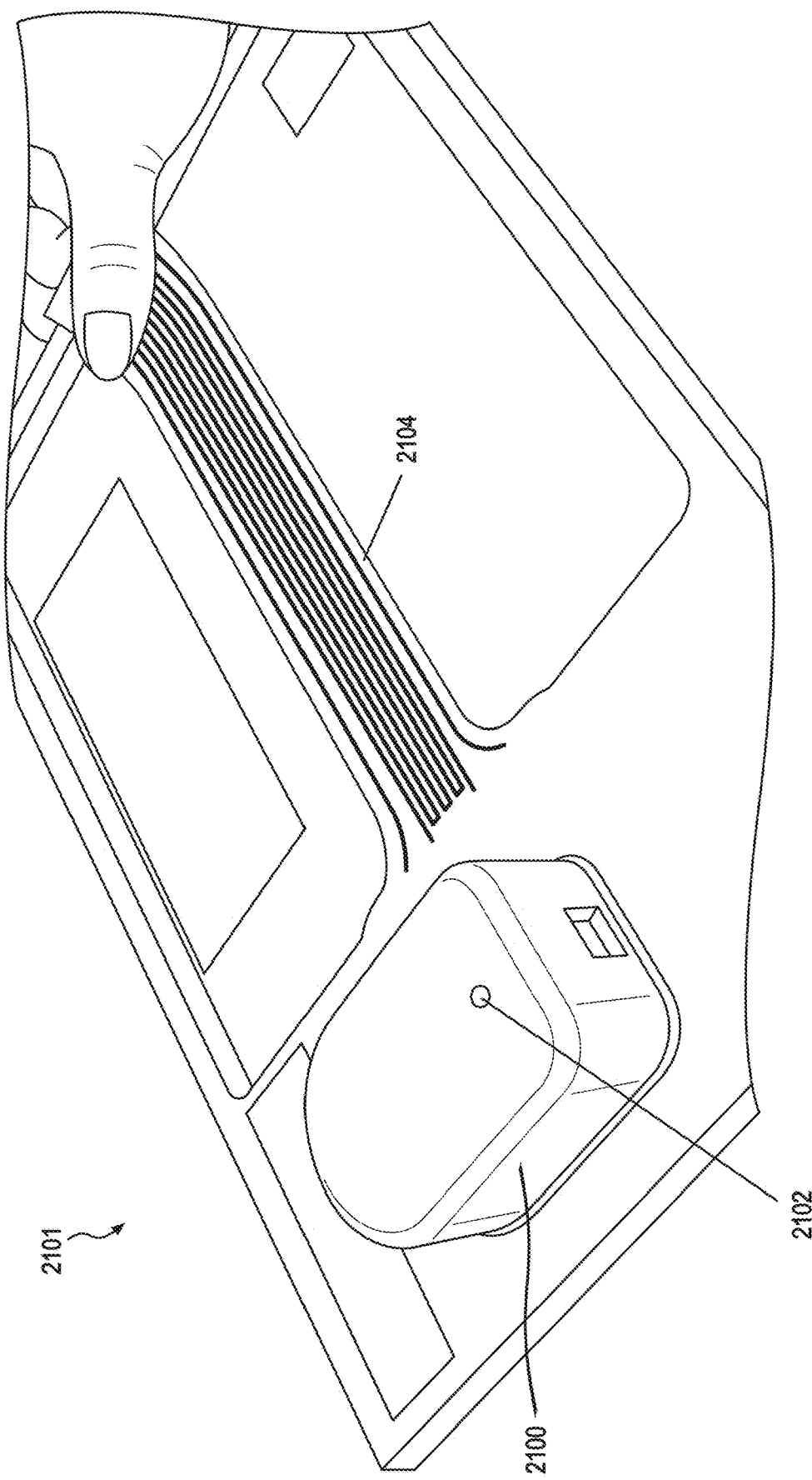
FIGS. 21A-C illustrate a use of an indicator on a wearable article, in accordance with at least one non-limiting aspect of the present disclosure.
Figure 21B:
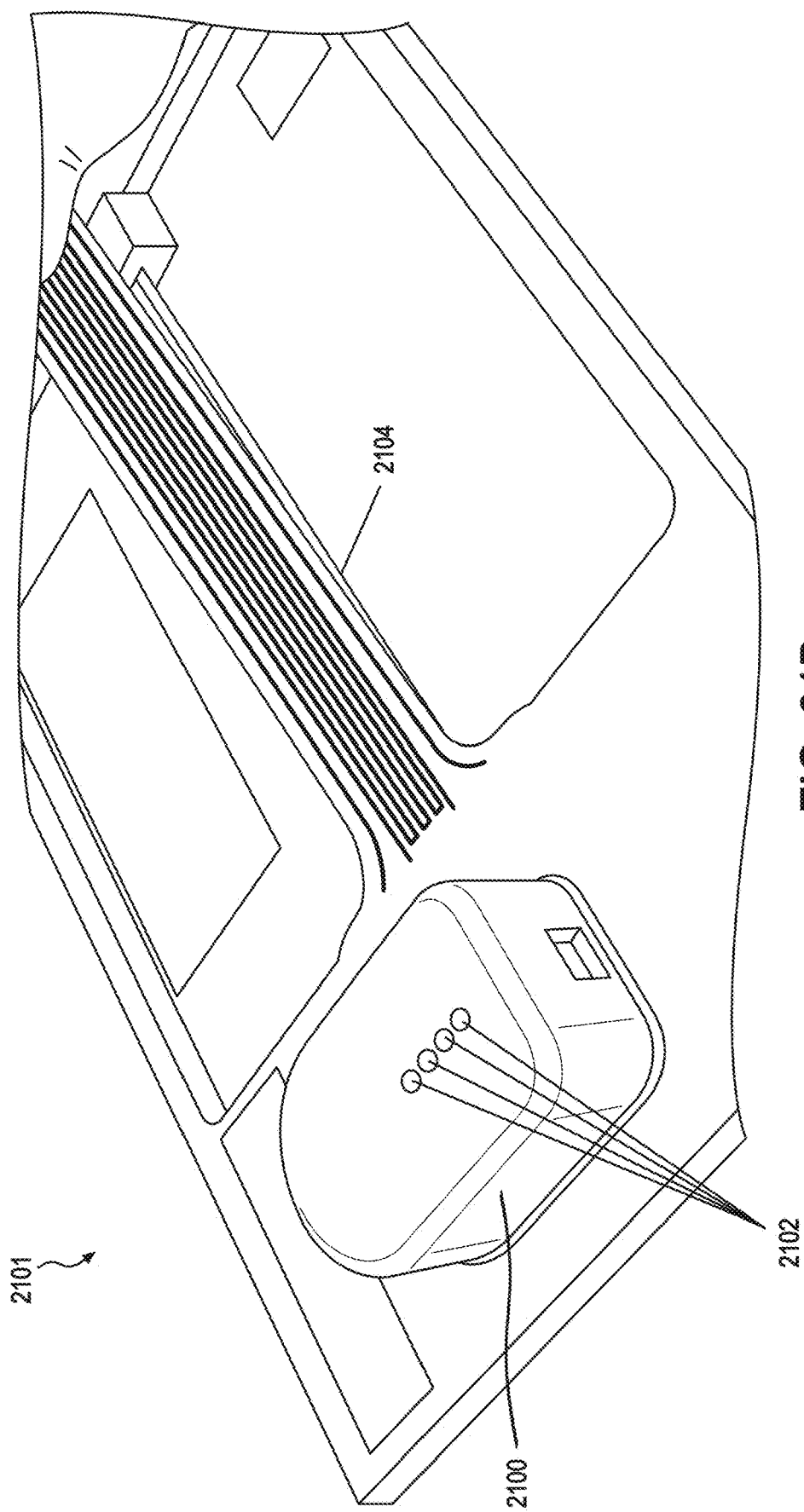
Figure 21C:
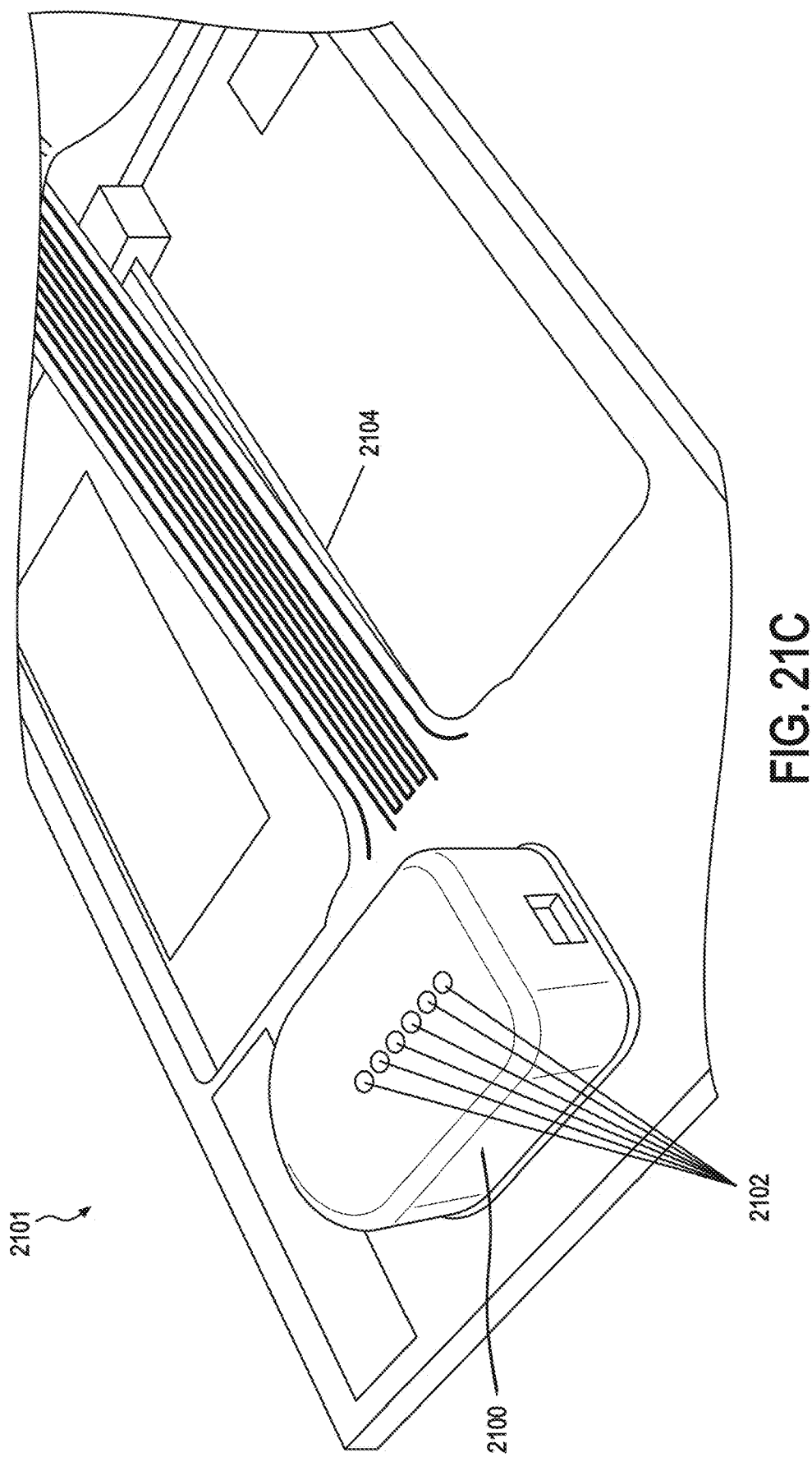

Referring now to FIGS. 21A-C, use of an indicator 2100 on a wearable article 2101 is depicted in accordance with at least one non-limiting aspect of the present disclosure. According to the non-limiting aspect of FIGS. 21A-C, the indicator 2100 can include a plurality of LEDs 2102 and can be electrically coupled to a flexible circuit 2104 configured as a strain gauge. A particular number of LEDs 2102 can be illuminated in response to electrical parameters (e.g., an inductance, a resistance, a voltage drop, a capacitance, and an electromagnetic field, etc.) generated by the flexible circuit 2104, wherein the electrical parameters are correlated to a physical parameter of the flexible circuit 2104 (e.g., strain applied due to flexion of the circuit). According to some non-limiting aspects, the indicator 2100 can include a processor (internal) programmed to illuminate a specific number of LEDs 2102 from the plurality in response to particular electrical parameters generated by the flexible circuit 2104 as a result of its physical condition (e.g., strain applied via a user's flexion).

For example, according to the non-limiting aspect of FIG. 21A, the flexible circuit 2104 is not under a significant amount of strain and therefore, only a single LED 2102 of the plurality is illuminated. However, in FIG. 21B, slightly more strain is being applied to the flexible circuit 2104 and therefore, four LEDs 2102 of the plurality are illuminated. According to FIG. 21C, a maximum number of LEDs 2102 of the plurality are illuminated in response to electrical parameters generated by the flexible circuit 2104 that are correlated to a maximum amount of strain applied to the flexible circuit 2104. According to some non-limiting aspects, the indicator 2100 can further include a more sophisticated display, a haptic sensor, and/or a transducer configured to provide more sophisticated visual indicia, haptic feedback, and/or audible alerts associated with the user's motions while wearing the joint monitoring sleeve 2101. Accordingly, the indicator 2100 can provide feedback to the user regarding their progress and range of motion. In other words, according to some non-limiting aspects, the on-board indicator 2100 can also be used to guide the patient through range of motion exercises during rehabilitation.

Referring now to FIG. 22, a method 2200 of calibrating strain gauge (e.g., strain gauge 1312 of FIG. 13) data and IMU (e.g., IMU 1308 of FIG. 13) data is depicted in accordance with at least one non-limiting aspect of the present disclosure. According to the non-limiting aspect of FIG. 22, the method 2200 can include initializing 2202 a system that includes a flexible circuit (e.g., flexible circuits 1300, 1400 of FIGS. 13, 14A, and 14B) and an IMU (e.g., IMU 1308 of FIG. 13), and then commencing 2204 a calibration sequence for the IMU. Subsequently, the method 2200 entails logging 2206 strain data from the flexible circuit and logging 2208 IMU data from the IMU.

It shall be appreciated that the steps of logging 2206 strain data and logging 2208 IMU data can be interchangeable and that, according to some non-limiting aspects, the method 2200 can be used to calibrate strain data to IMU data as opposed to IMU data being calibrated to strain data. In other words, the method 2200 of calibration is bidirectional. This can be particularly useful in non-limiting aspects where alternate conductors (e.g., silver ink, etc.) are used to form strain-sensing, flexible circuits. Since circuits that use alternate conductors may experience hysteresis and thus, may experience measurable changes in electrical characteristics upon returning to a relaxed state after undergoing a number of deformation cycles, strain data may need to be calibrated to IMU data to account for "strain creep."

Once the desired sample sizes are logged, the method 2200 includes correlating 2210 the logged strain data to the logged IMU data and calculating 2212 a drift based on a spatial position of the IMU inferred based, at least in part, on the correlation. Accordingly, the method 2200 includes outputting 2216 corrected IMU-dependent information based, at least in part, on the calculated drift. However, according to some non-limiting aspects, the method 2200 can further include outputting 2214 strain-dependent information based on strain data logged from the flexible circuit, alone.

In other words, the measured strain may have a calibration for a plurality of angles and may infer the angles between the calibration points (e.g., by assuming linear strain), which may be generally accurate for both metal gel conductor-based strain sensors and the bio-mechanics of the motion of body members covered by a wearable article. The addition of IMUs adds a symbiotic measure of angle. The strain sensor can be used via the method 2200 of FIG. 22 to calibrate or "re-home" data from the IMUs. Also, the IMUs can inform of motions that would act to add to the strain sensor, like that of rotation at the joint or hyper extension beyond the set points of the strain sensor.

Additionally, as previously discussed, the use of two IMUs positioned on different limbs opposite a joint can be implemented for inferencing joint movement and angular position of the limbs, but has been found to lack reliability over extended periods of use due to "drift" in the data provided by the IMU's. Over extended periods of time, the drift can result in datasets that are not trustworthy, since the inferred position and spatial relationship between the IMUs is no longer within an acceptable tolerance of their actual position on the wearer's body. Attempting to understand limb and joint movements or rely on the data being provided by the IMU pair, for example, to remotely monitor the health of the joint or remotely perform physical therapy and training to rehabilitate the joint, is therefore not possible.

However via the addition of the strain sensor and the method 2200 of FIG. 2, the wearable articles disclosed herein can provide not just data that is relatable to joint position and motion, but also serves to re-home the IMU's spatial position to generate more reliable data or extended periods of use, it may be necessary to benchmark associated strain and IMU-inferred spatial position data utilizing a calibration procedure for each wearer of a sleeve provided with this sensor configuration. This may be performed by the wearer moving their limb or body members contained in the sleeve to a variety of different positions and logging IMU inferred spatial location data vs measured strain. Thus, strain measurements may be used to anchor and correct the inferred spatial location of the IMU's as calculated by a processor (e.g., a micro-control unit ("MCU"), etc.) integrated in some aspects to the sleeve.

Typically calibration of an IMU would not be possible with a strain sensor since strain sensors are traditionally capable of measuring very small strains only, in the order of micrometers. Strains of such a small magnitude may be less than the drift in the spatial coordinates inferred by an IMU. However, a strain sensor made from a deformable conductor (e.g., metal gel) can Measure strains in the order of centimeters and decimeters, and even greater magnitudes depending on the size of the sensor and the resilience of the substrate used to make the sensor. Thus, the use of a strain sensor to determine a correction factor to the drift in spatial position inferred by an IMU has considerable value to wearable electronics where translations of the IMU's as a result of relative motion of body parts results in substantial stretching of the wearable device by the user's body. Substantial stretching may be defined as linear stretch of 3 or more millimeters. In some applications, it may be defined as little as about 1 millimeter. In other examples, it may be defined as 5 or 10 millimeters, or even more, depending on the use case of the sleeve.

The principles disclosed above may be applied to a sleeve fitted with a single IMU, which may provide substantially similar motion information for one limb, digit, or other body member on either side of a joint of the wearer. The position of the other limb may be inferred from strain data. It may be useful to pair the brace with a smartphone that may run a dedicated app to provide additionally functionality such as the ability to record a voice memo, e.g., when logging a discomfort position or painful activity which may be reviewed at a later time by a physiotherapist or other medical professional. Further, the data may be streamed wirelessly to cloud storage or monitored in real time by an individual in a remote location, for example, for providing therapeutic instructions or advice, exercises, training, or diagnosis of an injury.

Figure 23:
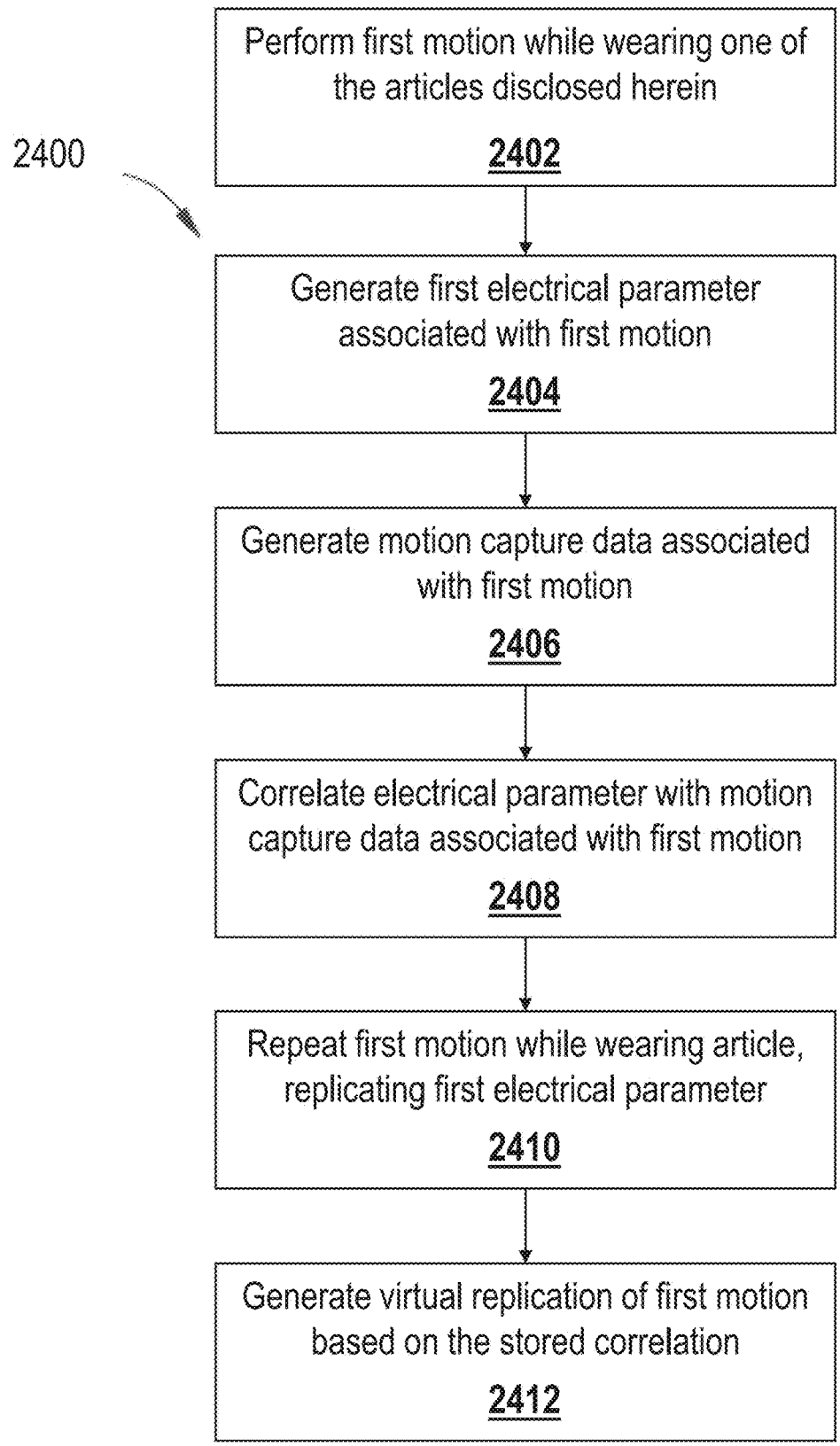
FIG. 23 illustrates a method of generating signals associated with electrical parameters and correlating those electrical parameters to the physical motions of a user of the wearable articles disclosed herein, in accordance with at least one non-limiting aspect of the present disclosure.

Referring now to FIG. 23, a method 2400 of generating signals associated with electrical parameters and correlating those electrical parameters to the physical motions of a user of the wearable articles disclosed herein is depicted in accordance with at least one non-limiting aspect of the present disclosure. According to the non-limiting aspect of FIG. 23, the method 2400 can include performing 2402 a first motion while wearing one of the articles disclosed herein. Upon performing 2402 the first motion, one of the flexible circuits can generate a first electrical parameter (e.g., an inductance, a resistance, a voltage drop, a capacitance, and an electromagnetic field, etc.) associated with the first motion, via any of the trace configurations and/or electrical features disclosed herein. The first motion can be monitored via a camera, or any other device capable of generating 2406 motion capture data associated with the first motion. Once the electrical parameter and motion capture data associated with the first motion are generated, the electrical parameter associated with the first motion can be correlated 2408 to the motion capture data associated with the first motion. The correlation can be stored such that, when the first motion is repeated 2410, a processor communicably coupled to the articles disclosed will receive one or more signals that it can determine are associated with the first electrical parameter. Accordingly, the processor can generate 2412 a virtual replication of the first motion based on the stored correlation.

However, the steps illustrated in FIG. 23 are not the exclusive steps of the method 2400 contemplated by the present disclosure. For example, according to some non-limiting aspects, the method 2400 can further include generating baseline electrical parameters and replicating the steps for a plurality of motions, such that an entire range of motions can be virtually replicated using the articles disclosed herein. According to some non-limiting aspects, the method can include the interim step of correlating the electrical parameter to a physical parameter (e.g., a strain, a stress, a pressure, a dimension, etc.) of the article and its circuits. In some non-limiting aspects, correlating the electrical parameter to the physical parameter can occur in lieu of correlating the electrical parameter to the motion capture data. Moreover, the method can include receiving and processing input from one or more pressure sensors coupled to the article, and virtually recreating an interaction between a user of the article and an object in the real environment, based on signals received from the one or more pressure sensors.

Since the inventive principles of this patent disclosure can be modified in arrangement and detail without departing from the inventive concepts, such changes and modifications are considered to fall within the scope of the following claims. The use of terms such as first and second are for purposes of differentiating different components and do not necessarily imply the presence of more than one component.

The electrically conductive compositions, such as conductive gels, comprised in the articles described herein can, for example, have a paste like or gel consistency that can be created by taking advantage of, among other things, the structure that gallium oxide can impart on the compositions when gallium oxide is mixed into a eutectic gallium alloy. When mixed into a eutectic gallium alloy, gallium oxide can form micro or nanostructures that are further described herein, which structures are capable of altering the bulk material properties of the eutectic gallium alloy.

As used herein, the term "eutectic" generally refers to a mixture of two or more phases of a composition that has the lowest melting point, and where the phases simultaneously crystallize from molten solution at this temperature. The ratio of phases to obtain a eutectic is identified by the eutectic point on a phase diagram. One of the features of eutectic alloys is their sharp melting point.

In some non-limiting aspects, the properties of the deformable conductive material and/or the properties of the layers surrounding the patterns of the deformable conductive material may be adjusted and/or optimized to ensure that the patterns of deformable conductive material heal upon unitization of the surrounding layers. For example, the deformable conductive material may be optimized to have a viscosity such that the deformable conductive material is able to heal upon unitization of the layers but not such that the deformable conductive material overly deforms and does not achieve the intended pattern. As another example, and adhesive characteristics and/or viscosity of the deformable conductive material may be optimized such that it remains on the substrate layer upon removal of the removable stencil 50 and but does not adhere to the channels 504, 506 of the stencil thereby lifting the deformable conductive material off of the substrate layer. In some aspects, a viscosity of the deformable conductive material may, when under high shear (e.g., in motion), be in a range of about 10 Pascal seconds (Pa*s) and 500 Pa*s, such as a range of 50 Pa*s and 300 Pa*s, and/or may be about 50 Pa*s, about 60 Pa*s, about 70 Pa*s, about 80 Pa*s, about 90 Pa*s, about 100 Pa*s, about 110 Pa*s, about 120 Pa*s, about 130 Pa*s, about 140 Pa*s, about 150 Pa*s, about 160 Pa*s, about 170 Pa*s, about 180 Pa*s, about 190 Pa*s, or about 200 Pa*s. In some aspects, a viscosity of the deformable conductive material may, when under low shear (e.g., at rest), be in a range of 1,000,000 Pa*s and 40,000,000 Pa*s and/or may be about 10,000,000 Pa*s, about 20,000,000 Pa*s, about 30,000,000 Pa*s, or about 40,000,000 Pa*s. According to some non-limiting aspects, the micro/nanostructure can include oxide sheets that form a cross-linked structure, which may be achieved by mixing in a way that entrains air into the mixture or by sonication that induces cavitation at the surface drawing in air to the mixture such that oxide formation in the cross-linked structures.

The electrically conductive compositions described herein can have any suitable conductivity, such as a conductivity of from about $2\times10^5$ S/m to about $8\times10^5$ S/m.

The electrically conductive compositions described herein can have ay suitable melting point, such as a melting point of from about $-20°$ C. to about $10°$ C., about $-10°$ C. to about $5°$ C., about $-5°$ C. to about $5°$ C. or about $-5°$ C. to about $0°$ C.

The electrically conductive compositions can comprise a mixture of a eutectic gallium alloy and gallium oxide, wherein the mixture of eutectic gallium alloy and gallium oxide has a weight percentage (wt %) of between about 59.9% and about 99.9% eutectic gallium alloy, such as between about 67% and about 90%, and a wt % of between about 0.1% and about 2.0% gallium oxide such as between about 0.2 and about 1%. For example, the electrically conductive compositions can have about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater, such as about 99.9% eutectic gallium alloy, and about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, and about 2.0% gallium oxide.

The eutectic gallium alloy can include gallium-indium or gallium-indium-tin in any ratio of elements. For example, a eutectic gallium alloy includes gallium and indium. The electrically conductive compositions can have any suitable percentage of gallium by weight in the gallium-indium alloy that is between about 40% and about 95%, such as about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

The electrically conductive compositions can have a percentage of indium by weight in the gallium-indium alloy that is between about 5% and about 60%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

The eutectic gallium alloy can include gallium and tin. For example, the electrically conductive compositions can have a percentage of tin by weight in the alloy that is between about 0.001% and about 50%, such as about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

The electrically conductive compositions can comprise one or more micro-particles or sub-micron scale particles blended with the eutectic gallium alloy and gallium oxide. The particles can be suspended, either coated in eutectic gallium alloy or gallium and encapsulated in gallium oxide or not coated in the previous manner, within eutectic gallium alloy. The micro- or sub-micron scale particles can range in size from nanometer to micrometer and can be suspended in gallium, gallium-indium alloy, or gallium-indium-tin alloy. Particle to alloy ratio can vary and can change the flow properties of the electrically conductive compositions. The micro and nanostructures can be blended within the electrically conductive compositions through sonication or other suitable means. The electrically conductive compositions can include a colloidal suspension of micro and nanostructures within the eutectic gallium alloy/gallium oxide mixture.

The electrically conductive compositions can further include one or more micro-particles or sub-micron scale particles dispersed within the compositions. This can be achieved in any suitable way, including by suspending particles, either coated in eutectic gallium alloy or gallium and encapsulated in gallium oxide or not coated in the previous manner, within the electrically conductive compositions or, specifically, within the eutectic gallium alloy fluid. These particles can range in size from nanometer to micrometer and can be suspended in gallium, gallium-indium alloy, or gallium-indium-tin alloy. Particle to alloy ratio can vary, in order to, among other things, change fluid properties of at least one of the alloys and the electrically conductive compositions. In addition, the addition of any ancillary material to colloidal suspension or eutectic gallium alloy in order to, among other things, enhance or modify its physical, electrical or thermal properties. The distribution of micro and nanostructures within the at least one of the eutectic gallium alloy and the electrically conductive compositions can be achieved through any suitable means, including sonication or other mechanical means without the addition of particles. In certain aspects, the one or more micro-particles or sub-micron particles are blended with the at least one of the eutectic gallium alloy and the electrically conductive compositions with wt % of between about 0.001% and about 40.0% of micro-particles, for example about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40.

The one or more micro- or sub-micron particles can be made of any suitable material including soda glass, silica, borosilicate glass, quartz, oxidized copper, silver coated copper, non-oxidized copper, tungsten, super saturated tin granules, glass, graphite, silver coated copper, such as silver coated copper spheres, and silver coated copper flakes, copper flakes, or copper spheres, or a combination thereof, or any other material that can be wetted by the at least one of the eutectic gallium alloy and the electrically conductive compositions. The one or more micro-particles or sub-micron scale particles can have any suitable shape, including the shape of spheroids, rods, tubes, a flakes, plates, cubes, prismatic, pyramidal, cages, and dendrimers. The one or more micro-particles or sub-micron scale particles can have any suitable size, including a size range of about 0.5 microns to about 60 microns, as about 0.5 microns, about 0.6 microns, about 0.7 microns, about 0.8 microns, about 0.9 microns, about 1 microns, about 1.5 microns, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 26 microns, about 27 microns, about 28 microns, about 29 microns, about 30 microns, about 31 microns, about 32 microns, about 33 microns, about 34 microns, about 35 microns, about 36 microns, about 37 microns, about 38 microns, about 39 microns, about 40 microns, about 41 microns, about 42 microns, about 43 microns, about 44 microns, about 45 microns, about 46 microns, about 47 microns, about 48 microns, about 49 microns, about 50 microns, about 51 microns, about 52 microns, about 53 microns, about 54 microns, about 55 microns, about 56 microns, about 57 microns, about 58 microns, about 59 microns, or about 60 microns.

The electrically conductive compositions described herein can be made by any suitable method, including a method comprising blending surface oxides formed on a surface of a eutectic gallium alloy into the bulk of the eutectic gallium alloy by shear mixing of the surface oxide/alloy interface. Shear mixing of such compositions can induce a cross linked microstructure in the surface oxides;

thereby forming a conducting shear thinning gel composition. A colloidal suspension of micro-structures can be formed within the eutectic gallium alloy/gallium oxide mixture, for example as, gallium oxide particles and/or sheets.

The surface oxides can be blended in any suitable ratio, such as at a ratio of between about 59.9% (by weight) and about 99.9% eutectic gallium alloy, to about 0.1% (by weight) and about 2.0% gallium oxide. For example percentage by weight of gallium alloy blended with gallium oxide is about 60%, 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater, such as about 99.9% eutectic gallium alloy while the weight percentage of gallium oxide is about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, and about 2.0% gallium oxide. In aspects, the eutectic gallium alloy can include gallium-indium or gallium-indium-tin in any ratio of the recited elements. For example, a eutectic gallium alloy can include gallium and indium.

The weight percentage of gallium in the gallium-indium alloy can be between about 40% and about 95%, such as about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Alternatively or in addition, the weight percentage of indium in the gallium-indium alloy can be between about 5% and about 60%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

A eutectic gallium alloy can include gallium, indium, and tin. The weight percentage of tin in the gallium-indium-tin alloy can be between about 0.001% and about 50%, such as about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.4%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

The weight percentage of gallium in the gallium-indium-tin alloy can be between about 40% and about 95%, such as about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Alternatively or in addition, the weight percentage of indium in the gallium-indium-tin alloy can be between about 5% and about 60%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

One or more micro-particles or sub-micron scale particles can be blended with the eutectic gallium alloy and gallium oxide. For example, the one or more micro-particles or sub-micron particles can be blended with the mixture with wt % of between about 0.001% and about 40.0% of microparticles in the composition, for example about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40. In aspects the particles can be soda glass, silica, borosilicate glass, quartz, oxidized copper, silver coated copper, non-oxidized copper, tungsten, super saturated tin granules, glass, graphite, silver coated copper, such as silver coated copper spheres, and silver coated copper flakes, copper flakes or copper spheres or a combination thereof, or any other material that can be wetted by gallium. In some aspects the one or more micro-particles or sub-micron scale particles are in the shape of spheroids, rods, tubes, a flakes, plates, cubes, prismatic, pyramidal, cages, and dendrimers. In certain aspects, the one or more micro-particles or sub-micron scale particles are in the size range of about 0.5 microns to about 60 microns, as about 0.5 microns, about 0.6 microns, about 0.7 microns, about 0.8 microns, about 0.9 microns, about 1 microns, about 1.5 microns, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 26 microns, about 27 microns, about 28 microns, about 29 microns, about 30 microns, about 31 microns, about 32 microns, about 33 microns, about 34 microns, about 35 microns, about 36 microns, about 37 microns, about 38 microns, about 39 microns, about 40 microns, about 41 microns, about 42 microns, about 43 microns, about 44 microns, about 45 microns, about 46 microns, about 47 microns, about 48 microns, about 49 microns, about 50 microns, about 51 microns, about 52 microns, about 53 microns, about 54 microns, about 55 microns, about 56 microns, about 57 microns, about 58 microns, about 59 microns, or about 60 microns.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

Various aspects of the subject matter described herein are set out in the following numbered clauses:

Clause 1: A system configured to monitor and characterize motions of a user, the system including: a wearable article including: a tubular body including a resilient material; a flexible circuit including a fluid-phase conductor configured to generate a first signal; and an inertial measurement unit ("IMU") coupled to the resilient material, wherein the IMU is configured to generate a second signal; and a processor communicably coupled to the flexible circuit and the IMU.

Clause 2: The system according to clause 1, wherein the processor is configured to: receive the first signal from the flexible circuit and the second signal from the IMU; determine a first electrical parameter associated with the flexible circuit based on the first signal; determine a second electrical parameter associated with the IMU based on the second signal; correlate the first electrical parameter to a first physical parameter associated with the flexible circuit and the second electrical parameter to a second physical parameter associated with the IMU; and generate a model of the wearable article based on the correlation.

Clause 3: The system according to either of clauses 1 or 2, wherein the processor is further configured to: receive the first signal from the flexible circuit and the second signal from the IMU; determine a first electrical parameter associated with the flexible circuit based on the first signal; determine a second electrical parameter associated with the IMU based on the second signal; correlate the first electrical parameter associated with the flexible circuit to the second electrical parameter associated with the IMU; modify the second physical parameter associated with the IMU based on the correlation of the first electrical parameter associated with the flexible circuit to the second electrical parameter associated with the IMU; and update the model of the wearable article based on the modification.

Clause 4: The system according to any of clauses 1-3, wherein the processor is communicably coupled to the flexible circuit and the IMU via a plurality of conductive traces including the fluid-phase conductor.

Clause 5: The system according to any of clauses 1-4, wherein the wearable article further includes a wireless transmitter, and wherein the processor is communicably coupled to the flexible circuit and the IMU via the wireless transmitter Clause 6: The system according to any of clauses 1-5, wherein the wearable article further includes a pressure sensor including a fluid-phase conductor.

Clause 7: The system according to any of clauses 1-6, wherein the fluid-phase conductor of the pressure sensor is configured as an inductive pressure sensor.

Clause 8. The system according to any of clauses 1-7, wherein the wearable article further includes a temperature sensor.

Clause 9: The system according to any of clauses 1-8, further including a second IMU coupled to the resilient material, and wherein the flexible circuit is dispositioned between the IMU and the second IMU.

Clause 10: The system according to any of clauses 1-9, wherein the wearable article is configured as a joint monitoring sleeve configured to be worn on a knee of the user.

Clause 11: The system according to any of clauses 1-10, wherein, when the joint monitoring sleeve is worn by the user, the IMU is positioned about the knee of the user, the second IMU is positioned below the knee of the user, and the flexible circuit is configured to traverse the knee of the user.

Clause 12: The system according to any of clauses 1-11, further including an indicator electrically coupled to the flexible circuit via a plurality of conductive traces including the fluid-phase conductor, wherein the indicator includes a plurality of light emitting diodes ("LEDs"), and wherein the indicator is configured to illuminate a number of LEDs of the plurality in response to a flexion of the flexible circuit.

Clause 13: A wearable article configured to monitor motions of a user, the wearable article including: a tubular body including a resilient material; a flexible circuit including a fluid-phase conductor configured to generate a first signal; and an inertial measurement unit ("IMU") coupled to the resilient material, wherein the IMU is configured to generate a second signal; and wherein the flexible circuit and the IMU are communicably coupled to a processor via a plurality of conductive traces including the fluid-phase conductor.

Clause 14: The wearable article according to clause 13, wherein the processor is coupled to resilient material, and wherein the flexible circuit and the IMU are communicably coupled to the processor via a plurality of conductive traces including the fluid-phase conductor.

Clause 15: The wearable article according to either of clauses 13 or 14, wherein the processor is configured to: receive the first signal from the flexible circuit and the second signal from the IMU; determine a first electrical parameter associated with the flexible circuit based on the first signal; determine a second electrical parameter associated with the IMU based on the second signal; correlate the first electrical parameter to a first physical parameter associated with the flexible circuit and the second electrical parameter to a second physical parameter associated with the IMU; and generate a model of the wearable article based on the correlation.

Clause 16: The wearable article according to any of clauses 13-15, wherein the wearable article further includes a pressure sensor including a fluid-phase conductor.

Clause 17: The wearable article according to any of clauses 13-16, wherein the fluid-phase conductor of the pressure sensor is configured as an inductive pressure sensor.

Clause 18: The wearable article according to any of clauses 13-17, wherein the wearable article further includes a temperature sensor including a fluid-phase conductor.

Clause 19: The wearable article according to any of clauses 13-18, further including an indicator electrically coupled to the flexible circuit via a plurality of conductive traces including the fluid-phase conductor, wherein the indicator includes a plurality of light emitting diodes ("LEDs"), and wherein the indicator is configured to illuminate a number of LEDs of the plurality in response to a flexion of the flexible circuit.

Clause 20: A method of generating a virtual representation of a physical motion performed by a user of a wearable article including a plurality of flexible circuits, the method including: performing a first motion while wearing the wearable article; generating, via a first flexible circuit of the plurality of flexible circuits, a first electrical parameter associated with the first motion; generating via a camera, motion capture data associated with the performance of the first motion; correlating, via a processor communicably coupled to the wearable article, the generated motion capture data to the generated first electrical parameter; storing, via a memory communicably coupled to the processor, the correlation; repeating the first motion while wearing the wearable article; and generating, via the processor, a virtual replication of the first motion based on exclusively on the stored correlation of the generated motion capture data to the generated first electrical parameter.

All patents, patent applications, publications, or other disclosure material mentioned herein, are hereby incorporated by reference in their entirety as if each individual reference was expressly incorporated by reference respectively. All references, and any material, or portion thereof, that are said to be incorporated by reference herein are incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference and the disclosure expressly set forth in the present application controls.

The present invention has been described with reference to various exemplary and illustrative aspects. The aspects described herein are understood as providing illustrative features of varying detail of various aspects of the disclosed invention; and therefore, unless otherwise specified, it is to be understood that, to the extent possible, one or more features, elements, components, constituents, ingredients, structures, modules, and/or aspects of the disclosed aspects may be combined, separated, interchanged, and/or rearranged with or relative to one or more other features, elements, components, constituents, ingredients, structures, modules, and/or aspects of the disclosed aspects without departing from the scope of the disclosed invention. Accordingly, it will be recognized by persons having ordinary skill in the art that various substitutions, modifications or combinations of any of the exemplary aspects may be made without departing from the scope of the invention. In addition, persons skilled in the art will recognize, or be able to ascertain using no more than routine experimentation, many equivalents to the various aspects of the invention described herein upon review of this specification. Thus, the invention is not limited by the description of the various aspects, but rather by the claims.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although claim recitations are presented in a sequence(s), it should be understood that the various operations may be performed in other orders than those which are described, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

As used herein, the singular form of "a", "an", and "the" include the plural references unless the context clearly dictates otherwise.

Directional phrases used herein, such as, for example and without limitation, top, bottom, left, right, lower, upper, front, back, and variations thereof, shall relate to the orientation of the elements shown in the accompanying drawing and are not limiting upon the claims unless otherwise expressly stated.

The terms "about" or "approximately" as used in the present disclosure, unless otherwise specified, means an acceptable error for a particular value as determined by one of ordinary skill in the art, which depends in part on how the value is measured or determined. In certain aspects, the term "about" or "approximately" means within 1, 2, 3, or 4 standard deviations. In certain aspects, the term "about" or "approximately" means within 50%, 200%, 105%, 100%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 100" includes all sub-ranges between (and including) the recited minimum value of 1 and the recited maximum value of 100, that is, having a minimum value equal to or greater than 1 and a maximum value equal to or less than 100. Also, all ranges recited herein are inclusive of the end points of the recited ranges. For example, a range of "1 to 100" includes the end points 1 and 100. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, any reference to a processor or microprocessor can be substituted for any "control circuit," which may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

What is claimed is:

1. A system configured to monitor and characterize motions of a user, the system comprising:
   a wearable article configured to be worn by the user, the wearable article comprising:
      a tubular body comprising a resilient material;
      a flexible circuit coupled with the tubular body, the flexible circuit comprising a fluid-phase conductor configured to generate a first signal; and
      an inertial measurement unit ("IMU") coupled to the resilient material, wherein the IMU is configured to generate a second signal; and
   a processor communicably coupled to the flexible circuit and the IMU, wherein the processor is configured to:
      receive the first signal from the flexible circuit and the second signal from the IMU;
      determine a first electrical parameter associated with the flexible circuit based on the first signal;
      determine a second electrical parameter associated with the IMU based on the second signal;
      correlate the first electrical parameter to a first physical parameter associated with the flexible circuit and the second electrical parameter to a second physical parameter associated with the IMU; and
      generate a virtual model of a joint or appendage of the user wearing the wearable article;
      determine a real-time position of the joint of the user based on the correlation; and
      display, via a display, the virtual model of the joint or appendage in a virtual position that is representative of the real-time position.

2. The system of claim 1, wherein the processor is further configured to:
   receive the first signal from the flexible circuit and the second signal from the IMU;
   determine the first electrical parameter associated with the flexible circuit based on the first signal;
      determine the second electrical parameter associated with the IMU based on the second signal;
   correlate the first electrical parameter associated with the flexible circuit to the second electrical parameter associated with the IMU;
   modify the second physical parameter associated with the IMU based on the correlation of the first electrical parameter associated with the flexible circuit to the second electrical parameter associated with the IMU; and
   update the virtual model based on the modification.

3. The system of claim 2, wherein the processor is communicably coupled to the flexible circuit and the IMU via a plurality of conductive traces comprising the fluid-phase conductor.

4. The system of claim 2, wherein the wearable article further comprises a wireless transmitter, and wherein the processor is communicably coupled to the flexible circuit and the IMU via the wireless transmitter.

5. A wearable article configured to monitor motions of a user, the wearable article comprising:
- a tubular body comprising a resilient material, the tubular body configured to be worn by the user;
- a flexible circuit coupled with the tubular body, the flexible circuit comprising a fluid-phase conductor configured to generate a first signal; and
- an inertial measurement unit ("IMU") coupled to the resilient material, wherein the IMU is configured to generate a second signal; and
- wherein the flexible circuit and the IMU are communicably coupled to a processor via a plurality of conductive traces comprising the fluid-phase conductor, wherein the processor is coupled to the resilient material, wherein the processor is configured to:
  - receive the first signal from the flexible circuit and the second signal from the IMU;
  - determine a first electrical parameter associated with the flexible circuit based on the first signal;
  - determine a second electrical parameter associated with the IMU based on the second signal;
  - correlate the first electrical parameter to a first physical parameter associated with the flexible circuit and the second electrical parameter to a second physical parameter associated with the IMU; and
  - generate a virtual model of a joint or appendage of the user wearing the wearable article;
  - determine a real-time position of the joint of the user based on the correlation; and
  - display, via a display, the virtual model of the joint or appendage in a virtual position that is representative of the real-time position.

6. The wearable article of claim 5, wherein the wearable article further comprises a pressure sensor comprising the fluid-phase conductor.

7. The wearable article of claim 5, wherein the fluid-phase conductor of the force sensor is configured as an inductive force sensor.

8. The wearable article of claim 5, wherein the wearable article further comprises a temperature sensor.

9. The wearable article of claim 5, further comprising an indicator electrically coupled to the flexible circuit via the plurality of conductive traces comprising the fluid-phase conductor, wherein the indicator comprises a plurality of light emitting diodes ("LEDs"), and wherein the indicator is configured to illuminate a number of LEDs of the plurality of LEDs in response to a flexion of the flexible circuit.

* * * * *